(12) United States Patent
Jones et al.

(10) Patent No.: US 9,566,377 B2
(45) Date of Patent: Feb. 14, 2017

(54) MEDICAL FLUID SENSING AND CONCENTRATION DETERMINATION IN A FLUID CARTRIDGE WITH MULTIPLE PASSAGEWAYS, USING A RADIO FREQUENCY DEVICE SITUATED WITHIN A MAGNETIC FIELD

(71) Applicant: Fresenius Medical Care Holdings, Inc., Waltham, MA (US)

(72) Inventors: Ross Peter Jones, Cambridge (GB); Pranav Chopra, Cambridge, MA (US); Rupert Menzies, Milton (GB); Mark David Tuckwell, Hertfordshire (GB); Martin Joseph Crnkovich, Walnut Creek, CA (US); Lynn Jensen, Syracuse, UT (US); Shashikant Dattatraya Kalaskar, Ogden, UT (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 90 days.

(21) Appl. No.: 13/836,597

(22) Filed: Mar. 15, 2013

(65) Prior Publication Data
US 2014/0263064 A1 Sep. 18, 2014

(51) Int. Cl.
*A61M 1/36* (2006.01)
*A61B 5/055* (2006.01)
(Continued)

(52) U.S. Cl.
CPC ............ *A61M 1/3621* (2013.01); *A61B 5/055* (2013.01); *A61B 5/14546* (2013.01);
(Continued)

(58) Field of Classification Search
CPC .......... A61B 5/055; A61K 33/14; A61M 1/16; A61M 1/36; A61M 1/1656; A61M 1/3643; A61M 2001/165; A61M 2001/1609; A61M 2001/1666; A61M 2001/3437; B01D 11/00; B01D 61/00; B06B 1/06; B06B 1/0648; C02F 1/44; G01G 3/16; G01G 17/02; G01G 9/00; G01H 11/08; G01N 24/08; G01N 29/024
(Continued)

(56) References Cited

U.S. PATENT DOCUMENTS 1,406,372 A 12/1921 Grapp
1,689,432 A 12/1927 Hartwig
(Continued)

FOREIGN PATENT DOCUMENTS

EP 0311848 4/1989
EP 1277485 1/2003
(Continued)

OTHER PUBLICATIONS

Kim et al., "Multichannel transceiver dual-tuned RF coil for proton/sodium MR imaging of knee cartilage at 3 T", Magnetic Resonance Imaging, 30, 2012, pp. 562-571.
(Continued)

*Primary Examiner* — Dirk Bass
*Assistant Examiner* — Hayden Brewster
(74) *Attorney, Agent, or Firm* — Fish & Richardson P.C.

(57) ABSTRACT

This disclosure relates to medical fluid sensors and related systems and methods. In certain aspects, a method includes reading an indicia of a medical fluid cartridge to determine a volume of a fluid passageway of the medical fluid cartridge indicated by the indicia, receiving radio frequency energy generated by excited atoms in medical fluid in the fluid passageway of the medical fluid cartridge, and determining a concentration of a substance in the medical fluid based on
(Continued)

the determined volume of the fluid passageway of the medical fluid cartridge indicated by the indicia and the received radio frequency energy generated by the excited atoms in the medical fluid in the fluid passageway of the medical fluid cartridge.

15 Claims, 28 Drawing Sheets

(51) Int. Cl.
G01N 24/08 (2006.01)
A61M 1/16 (2006.01)
A61B 5/145 (2006.01)
G01R 33/30 (2006.01)
G01R 33/34 (2006.01)
G01R 33/383 (2006.01)

(52) U.S. Cl.
CPC ........ *A61M 1/1607* (2014.02); *A61M 1/1609* (2014.02); *A61M 1/3609* (2014.02); *G01N 24/08* (2013.01); *A61M 2205/12* (2013.01); *A61M 2205/3317* (2013.01); *A61M 2230/20* (2013.01); *G01R 33/302* (2013.01); *G01R 33/34053* (2013.01); *G01R 33/383* (2013.01)

(58) Field of Classification Search
USPC ................................. 73/61.41, 865
See application file for complete search history.

(56) References Cited

U.S. PATENT DOCUMENTS

| | | |
|---|---|---|
| 2,107,173 A | 2/1938 | William |
| 3,130,289 A | 4/1964 | Lawrence |
| 3,605,783 A | 9/1971 | Pecker |
| 3,694,625 A | 9/1972 | Cole |
| 3,808,401 A | 4/1974 | Wright |
| 3,867,688 A | 2/1975 | Koski |
| 4,136,708 A | 1/1979 | Cosentino |
| 4,262,177 A | 4/1981 | Paxton et al. |
| 4,508,622 A | 4/1985 | Polaschegg |
| 4,613,820 A | 9/1986 | Edelstein et al. |
| 4,676,467 A | 6/1987 | Palsulich |
| 4,778,451 A | 10/1988 | Kamen |
| 4,808,161 A | 2/1989 | Kamen |
| 4,826,482 A | 5/1989 | Kamen |
| 4,869,286 A | 9/1989 | Williams et al. |
| 4,902,282 A | 2/1990 | Bellotti et al. |
| 4,902,877 A | 2/1990 | Grasso et al. |
| 4,950,134 A | 8/1990 | Bailey et al. |
| 4,976,162 A | 12/1990 | Kamen |
| 5,002,471 A | 3/1991 | Perlov |
| 5,024,756 A | 6/1991 | Sternby |
| 5,088,515 A | 2/1992 | Kamen |
| 5,100,554 A | 3/1992 | Polaschegg |
| 5,116,021 A | 5/1992 | Faust et al. |
| 5,146,713 A | 9/1992 | Grafius |
| 5,178,182 A | 1/1993 | Kamen |
| 5,193,990 A | 3/1993 | Kamen et al. |
| 5,211,201 A | 5/1993 | Kamen et al. |
| 5,241,985 A | 9/1993 | Faust et al. |
| 5,243,289 A | 9/1993 | Blum et al. |
| 5,311,899 A | 5/1994 | Isayama et al. |
| 5,324,422 A | 6/1994 | Colleran et al. |
| 5,344,392 A | 9/1994 | Senninger et al. |
| 5,350,357 A | 9/1994 | Kamen et al. |
| D351,470 S | 10/1994 | Scherer et al. |
| 5,353,837 A | 10/1994 | Faust |
| 5,395,351 A | 3/1995 | Munsch |
| 5,421,208 A | 6/1995 | Packard et al. |
| 5,421,823 A | 6/1995 | Kamen et al. |
| 5,431,626 A | 7/1995 | Bryant et al. |
| 5,438,510 A | 8/1995 | Bryant et al. |
| 5,447,286 A | 9/1995 | Kamen et al. |
| 5,474,683 A | 12/1995 | Bryant et al. |
| 5,486,286 A | 1/1996 | Peterson et al. |
| 5,540,265 A | 7/1996 | Polaschegg et al. |
| 5,567,320 A | 10/1996 | Goux et al. |
| 5,570,716 A | 11/1996 | Kamen et al. |
| 5,572,992 A | 11/1996 | Kankkunen et al. |
| 5,583,948 A | 12/1996 | Shibayama |
| 5,628,908 A | 5/1997 | Kamen et al. |
| 5,634,896 A | 6/1997 | Bryant et al. |
| 5,640,995 A | 6/1997 | Packard et al. |
| 5,641,405 A | 6/1997 | Keshaviah et al. |
| 5,641,892 A | 6/1997 | Larkins et al. |
| 5,713,865 A | 2/1998 | Manning et al. |
| 5,741,125 A | 4/1998 | Neftel et al. |
| 5,755,683 A | 5/1998 | Houle et al. |
| 5,771,914 A | 6/1998 | Ling et al. |
| 5,772,637 A | 6/1998 | Heinzmann et al. |
| 5,788,099 A | 8/1998 | Treu et al. |
| 5,925,011 A | 7/1999 | Faict et al. |
| 5,925,014 A | 7/1999 | Teeple, Jr. |
| 5,938,634 A | 8/1999 | Packard |
| 5,986,455 A | 11/1999 | Magnuson |
| 5,989,423 A | 11/1999 | Kamen |
| 5,997,502 A | 12/1999 | Reilly et al. |
| 6,036,680 A | 3/2000 | Horne et al. |
| 6,041,801 A | 3/2000 | Gray et al. |
| 6,042,784 A | 3/2000 | Wamsiedler et al. |
| 6,065,941 A | 5/2000 | Gray et al. |
| 6,074,359 A | 6/2000 | Keshaviah et al. |
| 6,081,120 A | 6/2000 | Shen |
| 6,118,207 A | 9/2000 | Ormerod et al. |
| 6,126,831 A | 10/2000 | Goldau et al. |
| 6,164,621 A | 12/2000 | Bouchard et al. |
| 6,165,154 A | 12/2000 | Gray et al. |
| 6,187,199 B1 | 2/2001 | Goldau |
| 6,220,295 B1 | 4/2001 | Bouchard et al. |
| 6,223,130 B1 | 4/2001 | Gray et al. |
| 6,228,047 B1 | 5/2001 | Dadson |
| 6,316,864 B1 | 11/2001 | Ormerod |
| 6,343,614 B1 | 2/2002 | Gray et al. |
| 6,364,857 B1 | 4/2002 | Gray et al. |
| 6,382,923 B1 | 5/2002 | Gray |
| 6,404,197 B1 | 6/2002 | Anderson et al. |
| 6,406,276 B1 | 6/2002 | Normand et al. |
| 6,414,493 B1 | 7/2002 | Rezvani |
| 6,416,293 B1 | 7/2002 | Bouchard et al. |
| 6,459,175 B1 | 10/2002 | Potega et al. |
| 6,468,424 B1 | 10/2002 | Doenig et al. |
| 6,497,676 B1 | 12/2002 | Childers et al. |
| 6,503,062 B1 | 1/2003 | Gray et al. |
| 6,520,747 B2 | 2/2003 | Gray et al. |
| 6,558,343 B1 | 5/2003 | Neftel |
| 6,592,542 B2 | 7/2003 | Childers et al. |
| 6,595,944 B2 | 7/2003 | Balschat et al. |
| 6,604,908 B1 | 8/2003 | Bryant et al. |
| 6,614,008 B2 | 9/2003 | Tidrick |
| 6,648,845 B1 | 11/2003 | Gotch et al. |
| 6,653,841 B1 | 11/2003 | Koerdt et al. |
| 6,663,359 B2 | 12/2003 | Gray |
| 6,685,831 B2 | 2/2004 | Doenig et al. |
| 6,702,774 B1 | 3/2004 | Polaschegg |
| 6,709,417 B1 | 3/2004 | Houle et al. |
| 6,726,656 B2 | 4/2004 | Kamen et al. |
| 6,746,514 B2 | 6/2004 | Bedingfield et al. |
| 6,749,403 B2 | 6/2004 | Spencer et al. |
| 6,764,761 B2 | 7/2004 | Eu et al. |
| 6,799,883 B1 | 10/2004 | Urquhart et al. |
| 6,808,369 B2 | 10/2004 | Gray et al. |
| 6,814,547 B2 | 11/2004 | Childers et al. |
| 6,860,866 B1 | 3/2005 | Graf et al. |
| 6,869,538 B2 | 3/2005 | Yu et al. |
| 6,911,007 B2 | 6/2005 | Nier et al. |
| 6,995,563 B2 | 2/2006 | Talutis |
| 7,078,909 B2 | 7/2006 | Feng et al. |
| 7,279,903 B2 | 10/2007 | Quackenbush et al. |
| D556,909 S | 12/2007 | Reihanifam |
| D556,910 S | 12/2007 | Reihanifam |
| D576,281 S | 9/2008 | Reihanifam |

(56) References Cited

U.S. PATENT DOCUMENTS

| | | | |
|---|---|---|---|
| 7,463,129 | B1 | 12/2008 | Danby et al. |
| 7,661,293 | B2 | 2/2010 | Dam |
| 7,661,294 | B2 | 2/2010 | Dam |
| 7,788,047 | B2 | 8/2010 | Schick et al. |
| 8,182,692 | B2 | 5/2012 | Gotch |
| 8,324,900 | B2 | 12/2012 | Helvoort et al. |
| 8,353,870 | B2 | 1/2013 | Levin et al. |
| 8,409,864 | B2 | 4/2013 | Ash |
| 8,525,533 | B2 | 9/2013 | Sullivan |
| 2002/0000793 | A1 | 1/2002 | Hanaki |
| 2002/0045851 | A1* | 4/2002 | Suzuki .......... A61M 1/28 604/28 |
| 2002/0107474 | A1 | 8/2002 | Noack |
| 2002/0147423 | A1 | 10/2002 | Burbank et al. |
| 2003/0018395 | A1 | 1/2003 | Crnkovich et al. |
| 2003/0028094 | A1 | 2/2003 | Kumar et al. |
| 2003/0029451 | A1 | 2/2003 | Blair et al. |
| 2003/0040700 | A1 | 2/2003 | Hickle et al. |
| 2003/0042181 | A1 | 3/2003 | Metzner |
| 2003/0085621 | A1 | 5/2003 | Potega |
| 2003/0111457 | A1 | 6/2003 | Tidrick |
| 2003/0130606 | A1 | 7/2003 | Tuck |
| 2003/0136189 | A1 | 7/2003 | Lauman et al. |
| 2003/0195453 | A1 | 10/2003 | Han et al. |
| 2003/0200812 | A1 | 10/2003 | Kuhn et al. |
| 2003/0204162 | A1 | 10/2003 | Childers et al. |
| 2003/0217957 | A1 | 11/2003 | Bowman et al. |
| 2003/0217961 | A1 | 11/2003 | Hopping |
| 2003/0217975 | A1 | 11/2003 | Yu et al. |
| 2003/0218623 | A1 | 11/2003 | Krensky et al. |
| 2003/0220599 | A1 | 11/2003 | Lundtveit |
| 2003/0220605 | A1 | 11/2003 | Bowman et al. |
| 2003/0220607 | A1 | 11/2003 | Busby et al. |
| 2003/0220608 | A1 | 11/2003 | Huitt et al. |
| 2003/0220609 | A1 | 11/2003 | Childers et al. |
| 2003/0220627 | A1 | 11/2003 | Distler et al. |
| 2004/0010223 | A1 | 1/2004 | Busby et al. |
| 2004/0012391 | A1 | 1/2004 | Vaughan et al. |
| 2004/0019313 | A1 | 1/2004 | Childers et al. |
| 2004/0019320 | A1 | 1/2004 | Childers et al. |
| 2004/0024301 | A1 | 2/2004 | Hockett et al. |
| 2004/0031756 | A1 | 2/2004 | Suzuki et al. |
| 2004/0064080 | A1 | 4/2004 | Cruz et al. |
| 2004/0067161 | A1 | 4/2004 | Axelsson |
| 2004/0082903 | A1 | 4/2004 | Micheli |
| 2004/0085173 | A1 | 5/2004 | Decristofaro et al. |
| 2004/0122353 | A1 | 6/2004 | Shahmirian et al. |
| 2004/0135078 | A1 | 7/2004 | Mandro et al. |
| 2004/0193031 | A1* | 9/2004 | Fuller .......... A61B 5/05 600/365 |
| 2004/0195190 | A1 | 10/2004 | Min et al. |
| 2005/0025797 | A1 | 2/2005 | Wang et al. |
| 2005/0127919 | A1 | 6/2005 | Feng et al. |
| 2005/0151422 | A1 | 7/2005 | Gilmour |
| 2005/0230292 | A1 | 10/2005 | Beden et al. |
| 2005/0234381 | A1 | 10/2005 | Niemetz et al. |
| 2005/0242034 | A1 | 11/2005 | Connell et al. |
| 2006/0195064 | A1 | 8/2006 | Plahey et al. |
| 2007/0020701 | A1 | 1/2007 | Menon et al. |
| 2007/0244382 | A1 | 10/2007 | Robinson et al. |
| 2007/0278155 | A1 | 12/2007 | Lo et al. |
| 2008/0015493 | A1* | 1/2008 | Childers et al. ........ 604/29 |
| 2008/0077074 | A1 | 3/2008 | Keenan et al. |
| 2008/0136415 | A1 | 6/2008 | Rooij de et al. |
| 2009/0128155 | A1 | 5/2009 | Otake et al. |
| 2009/0167304 | A1 | 7/2009 | Prado et al. |
| 2009/0267617 | A1 | 10/2009 | Seyfi et al. |
| 2009/0278537 | A1 | 11/2009 | Harvey |
| 2010/0072994 | A1* | 3/2010 | Lee et al. .......... 324/307 |
| 2010/0164498 | A1 | 7/2010 | Helvoort et al. |
| 2011/0004143 | A1 | 1/2011 | Beiriger et al. |
| 2011/0009800 | A1 | 1/2011 | Dam |
| 2011/0043209 | A1 | 2/2011 | Zhu |
| 2011/0199097 | A1 | 8/2011 | Hartsough |
| 2011/0304416 | A1 | 12/2011 | Warner et al. |
| 2012/0068723 | A1 | 3/2012 | Sullivan |
| 2012/0100546 | A1* | 4/2012 | Lowery et al. .......... 435/6.12 |
| 2012/0164644 | A1 | 6/2012 | Neely et al. |
| 2012/0203476 | A1 | 8/2012 | Dam |
| 2012/0232471 | A1* | 9/2012 | Chen .......... G01F 23/26 604/29 |
| 2012/0258545 | A1 | 10/2012 | Ash |

FOREIGN PATENT DOCUMENTS

| | | |
|---|---|---|
| EP | 0887655 B1 | 3/2004 |
| WO | 9211046 | 7/1992 |
| WO | 9625214 | 8/1996 |
| WO | WO9961900 A1 | 12/1999 |
| WO | WO0147415 A1 | 7/2001 |
| WO | WO2008001326 A1 | 1/2008 |
| WO | WO2010114932 A1 | 10/2010 |
| WO | WO2012022304 A1 | 2/2012 |
| WO | 2012108984 | 8/2012 |

OTHER PUBLICATIONS

Price et al., "Development of tissue-targeted metabonomics—Part 1—Analytical considerations", Journal of Pharmaceutical and Biomedical Analysis, 46, 2008, pp. 737-747.

Communication Relating to the Results of the Partial International Search for corresponding PCT Application No. PCT/2014/020378, mailed Jul. 2, 2014, 5 pages.

Pykett, Ian L., "NMR Imaging in Medicine", Scientific American, 1982, pp. 78-88.

Notification of Transmittal of the International Search report and the Written Opinion of the International Searching Authority from corresponding PCT Application No. PCT/US2014/020378, mailed Oct. 27, 2014, 18 pages.

Buess et al., "Acoustic ringing effects in pulsed nuclear magnetic resonance probes", Rev. Sci. Instrum., vol. 48, No. 8, 1978, pp. 1151-1155.

Depaula et al., "Clinical consequences of an individualized dialysate sodium prescription in hemodialysis patients," Kidney International, vol. 66 (2004), pp. 1232-1238.

Gambro®, "Prismaflex™ anticipating care needs and taking our innovative response . . . to new heights", © 2004, Gambro, Inc., Lakewood, CO, 8 pages.

Gambro®, "DEHP-free cartridge blood sets," © Nov. 2004, Gambro, Inc., Lakewood, CO, 4 pages.

Gotch et al., "Mechanisms determining the ratio of conductivity clearance to urea clearance", Kidney International, vol. 66, Supplement 89 (2004), pp. S1-S24.

Sleep Safe™ Operating Instructions, Fresenius Medical Care, Aug. 2000.

Zhou et al., "Impact of sodium and ultrafiltration profiling on haemodialysis-related hypotension", NDT Advance Access published online on Sep. 5, 2006.

2008T Hemodialysis Machine Operator's Manual. P.N. 490122 Rev E, Fresenius Medical Care, 2008.

Pang et al., "Common-Mode Differential-Mode (CMDM) Method for Double-Nuclear MR Signal Excitation and Reception at Ultrahigh Fields", IEEE Trans Med Imaging, Jun. 20, 2011, pp. 1965-1973.

* cited by examiner

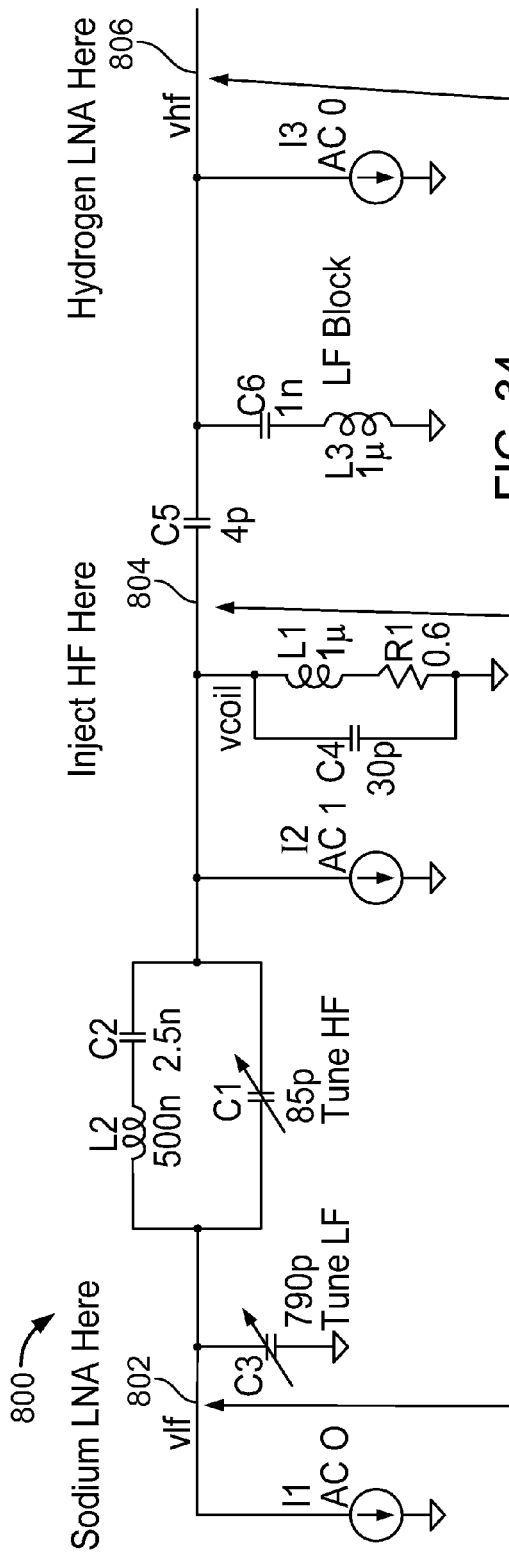
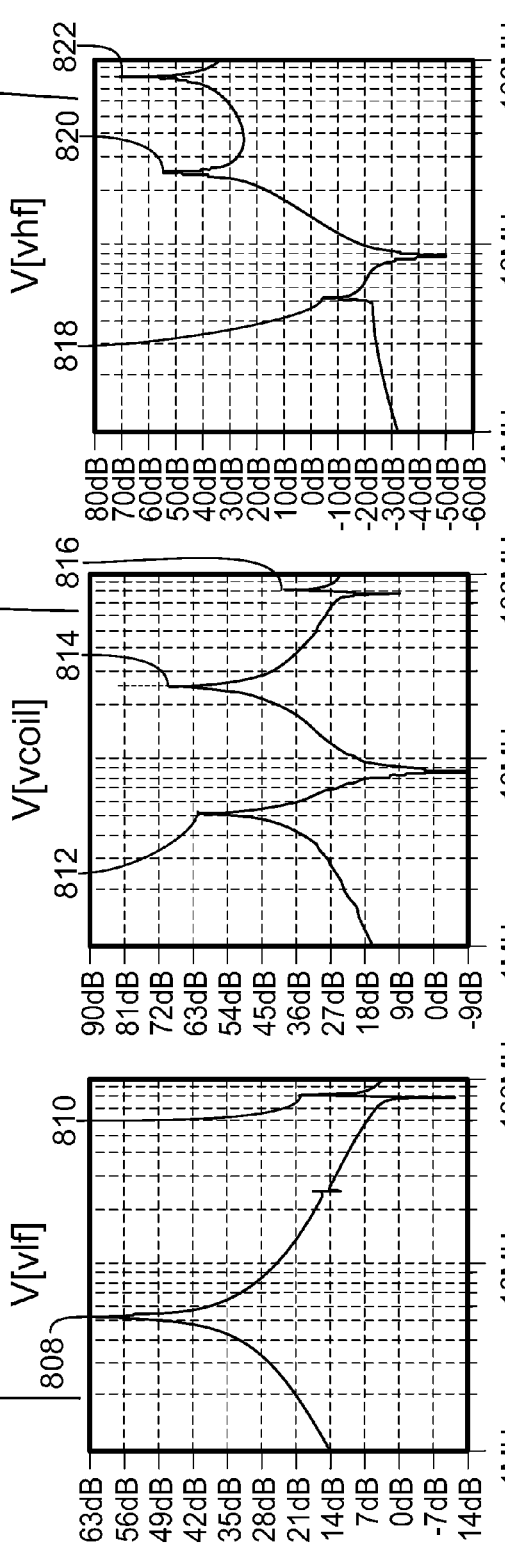
FIG. 34
FIG. 35
FIG. 36
FIG. 37

MEDICAL FLUID SENSING AND CONCENTRATION DETERMINATION IN A FLUID CARTRIDGE WITH MULTIPLE PASSAGEWAYS, USING A RADIO FREQUENCY DEVICE SITUATED WITHIN A MAGNETIC FIELD

TECHNICAL FIELD

This disclosure relates to medical fluid sensors and related systems and methods.

BACKGROUND

During hemodialysis, impurities and toxins are removed from the blood of a patient by drawing the blood out of the patient through a blood access site, typically via a catheter, and then passing the blood through an artificial kidney (often referred to as a "dialyzer"). The artificial kidney includes a semi-permeable membrane that separates a first conduit from a second conduit. Generally, a dialysis solution (often referred to as a "dialysate") flows through the first conduit of the dialyzer while the patient's blood flows through the second conduit of the dialyzer, causing impurities and toxins to be transferred from the blood to the dialysate through the semi-permeable membrane. The impurities and toxins can, for example, be removed from the blood by a diffusion process. After passing through the dialyzer, the purified blood is then returned to the patient.

Maintaining a substantially constant concentration of sodium in the patient's blood throughout the hemodialysis treatment can help to reduce or prevent discomfort experienced by the patient. Therefore, sodium concentrations in the patient's blood are often monitored during hemodialysis treatment. One way to detect the sodium concentration in a patient's blood is to connect a conductivity sensor to a blood line of the hemodialysis system and to determine the sodium concentration of the patient's blood flowing through that blood line based on the conductivity measured by the conductivity sensor. Sodium levels in the dialysate can then be adjusted to maintain the sodium concentration of the patient's blood within a desired range.

SUMMARY

In one aspect of the invention, a method includes using a dialysis fluid pump of a dialysis machine to deliver dialysis fluid to a first portion of a cartridge that is positioned within a magnetic field, exciting atoms in the dialysis fluid in the first portion of the cartridge by applying radio frequency energy to the dialysis fluid in the first portion of the cartridge, receiving radio frequency energy generated by the excited atoms in the dialysis fluid in the first portion of the cartridge, and determining a concentration of a substance in the dialysis fluid based on the received radio frequency energy generated by the excited atoms in the dialysis fluid in the first portion of the cartridge.

In another aspect of the invention, a dialysis system includes a magnet assembly that generates a magnetic field and defines a cavity configured to receive a first portion of a cartridge, a dialysis fluid pump that is operable to pump dialysis fluid to the first portion of the cartridge when the first portion of the cartridge is disposed in the cavity of the magnet assembly, and a radio frequency device configured to receive the first portion of the cartridge when the first portion of the cartridge is disposed in the cavity of the magnet assembly. The radio frequency device is operable to receive radio frequency energy generated by excited atoms in the dialysis fluid in the first portion of the cartridge when the first portion of the cartridge is disposed in the cavity of the magnet assembly and dialysis fluid has been pumped to the first portion of the cartridge.

In an additional aspect of the invention, a method includes using a medical fluid pump to deliver medical fluid to a first portion of a cartridge that is positioned within a magnetic field, exciting atoms in the medical fluid in the first portion of the cartridge by applying radio frequency energy to the medical fluid in the first portion of the cartridge, receiving radio frequency energy generated by the excited atoms in the medical fluid in the first portion of the cartridge, and determining a concentration of a substance in the medical fluid based on the received radio frequency energy generated by the excited atoms in the medical fluid in the first portion of the cartridge.

In a further aspect of the invention, a medical system includes a magnet assembly that generates a magnetic field and defines a cavity configured to receive a first portion of a cartridge, a medical fluid pump that is operable to pump medical fluid to the first portion of the cartridge when the first portion of the cartridge is disposed in the cavity of the magnet assembly, and a radio frequency device configured to receive the first portion of the cartridge when the first portion of the cartridge is disposed in the cavity of the magnet assembly. The radio frequency device is operable to receive radio frequency energy generated by excited atoms in the medical fluid in the first portion of the cartridge when the first portion of the cartridge is disposed in the cavity of the magnet assembly and medical fluid has been pumped to the first portion of the cartridge.

Implementations can include one or more of the following features.

In some implementations, the dialysis fluid is blood.

In certain implementations, the dialysis fluid is dialysate.

In some implementations, the dialysate is spent dialysate.

In certain implementations, the method further includes delivering fresh dialysate to the first portion of the cartridge, exciting atoms in the fresh dialysate in the first portion of the cartridge by applying radio frequency energy to the fresh dialysate in the first portion of the cartridge, receiving radio frequency energy generated by the excited atoms in the fresh dialysate in the first portion of the cartridge, and determining a concentration of the substance in the fresh dialysate based on the received radio frequency energy generated by the excited atoms in the fresh dialysate in the first portion of the cartridge.

In some implementations, the method further includes determining a concentration of the substance in blood of a dialysis patient based on the determined concentrations of the spent dialysate and the fresh dialysate.

In certain implementations, the method further includes adjusting a concentration of the substance in the fresh dialysate to match the determined concentration of the substance in the blood.

In some implementations, the substance is sodium.

In certain implementations, the dialysis fluid pump is a blood pump.

In some implementations, the dialysis fluid pump is a dialysate pump.

In certain implementations, the dialysis fluid is delivered to the first portion of the cartridge while dialysis treatment is being carried out by the dialysis machine.

In some implementations, the concentration of the substance in the dialysis fluid is determined while dialysis treatment is being carried out by the dialysis machine.

In certain implementations, the dialysis fluid is blood, and the method further includes adjusting a concentration of the substance in dialysate based on the determined concentration of the substance in the blood.

In some implementations, the concentration of the substance in the dialysate is adjusted to match the determined concentration of the substance in the blood.

In certain implementations, the method further includes adjusting the concentration of the substance in the dialysis fluid if the determined concentration of the substance in the dialysis fluid falls outside of a desired range.

In some implementations, adjusting the concentration of the substance in the dialysis fluid includes adding the substance to the dialysis fluid or adding a diluent to the dialysis fluid.

In certain implementations, the substance is sodium and adding the substance to the dialysis fluid includes adding a sodium chloride solution to the dialysis fluid.

In some implementations, the radio frequency energy generated by the excited atoms in the dialysis fluid in the first portion of the cartridge is received by a radio frequency device surrounding the first portion of the cartridge.

In certain implementations, applying the radio frequency energy to the dialysis fluid in the first portion of the cartridge includes activating the radio frequency device.

In some implementations, the radio frequency device is a radio frequency coil.

In certain implementations, the radio frequency coil is operated in a transmit mode while applying the radio frequency energy to the dialysis fluid in the first portion of the cartridge, and the radio frequency coil is operated in a receiving mode while receiving the radio frequency energy generated by the excited atoms in the dialysis fluid in the first portion of the cartridge.

In some implementations, operating the radio frequency coil in the transmit mode includes applying electrical energy to the radio frequency coil and operating the radio frequency coil in the receive mode includes ceasing the application of electrical energy to the radio frequency coil.

In certain implementations, the magnetic field is generated by a magnet assembly defining a cavity in which the radio frequency device and the first portion of the cartridge are disposed.

In some implementations, the magnet assembly includes a pair of magnets attached to a frame.

In certain implementations, the frame includes two U-shaped members that cooperate to form the cavity.

In some implementations, the method further includes passing the dialysis fluid through a first meandering fluid passageway defined by the cartridge prior to delivering the dialysis fluid to the first portion of the cartridge. The first meandering fluid passageway is positioned within the magnetic field.

In certain implementations, the first meandering fluid passageway is a U-shaped fluid passageway.

In some implementations, the dialysis fluid is in the first meandering fluid passageway for a sufficient period of time to polarize nuclei of the atoms.

In certain implementations, the dialysis fluid is in the first meandering fluid passageway for at least 150 milliseconds (e.g., 150 milliseconds to 300 milliseconds).

In some implementations, the first meandering fluid passageway is positioned outside a radio frequency device that applies the radio frequency energy to the dialysis fluid in the first portion of the cartridge.

In certain implementations, the first portion of the cartridge defines a second meandering fluid passageway.

In some implementations, the second meandering fluid passageway is a U-shaped fluid passageway.

In certain implementations, the dialysis fluid is in the second meandering fluid passageway for a sufficient period of time for the atoms in the dialysis fluid to be excited by the applied radio frequency energy and for the radio frequency energy generated by the excited atoms to be received.

In some implementations, the dialysis fluid is in the second meandering fluid passageway for at least 150 milliseconds (e.g., 150 milliseconds to 300 milliseconds).

In certain implementations, the dialysis fluid is delivered to the first portion of the cartridge at a rate of 50 milliliters per minute to 200 milliliters per minute.

In some implementations, the dialysis fluid flows through the first portion of the cartridge.

In certain implementations, the dialysis fluid flows through the first portion of the cartridge at a rate of 50 milliliters per minute to 200 milliliters per minute.

In some implementations, the method further includes passing the dialysis fluid through a first meandering fluid passageway defined by the cartridge before the dialysis fluid flows through the first portion of the cartridge. The first meandering fluid passageway is positioned within the magnetic field.

In certain implementations, the dialysis fluid flows through the first meandering fluid passageway at a first flow rate and passes through the first portion of the cartridge at a second flow rate that is less than the first flow rate.

In some implementations, the dialysis fluid flows through the first meandering fluid passageway at a rate of 50 milliliters per minute to 200 milliliters per minute.

In certain implementations, the dialysis fluid resides substantially stagnantly within the first portion of the cartridge for a period of time.

In some implementations, the dialysis fluid is dialysate.

In certain implementations, a first portion of the dialysis fluid is delivered to the first portion of the cartridge, and a second portion of the dialysis fluid passes through a second portion of the cartridge.

In some implementations, the second portion is positioned outside a radio frequency device that applies the radio frequency energy to the dialysis fluid in the first portion, and the second portion is at least partially positioned outside a magnet assembly that generates the magnetic field.

In certain implementations, the second portion of the cartridge defines a fluid passageway that bypasses the first portion of the cartridge.

In some implementations, the fluid passageway that bypasses the first portion of the cartridge is straight.

In certain implementations, the first portion of the dialysis fluid flows through the first portion of the cartridge at a slower rate than the second portion of the dialysis fluid passes through the second portion of the cartridge.

In some implementations, the first portion of the dialysis fluid flows through the first portion of the cartridge at a rate of 50 milliliters per minute to 200 milliliters per minute.

In certain implementations, the second portion of the dialysis fluid flows through the second portion of the cartridge at a rate of 400 milliliters per minute to 600 milliliters per minute.

In some implementations, the concentration of the substance in the dialysis fluid is determined as a function of (i) the radio frequency energy generated by the excited atoms in the dialysis fluid in the first portion of the cartridge and (ii) a volume of the first portion of the cartridge.

In certain implementations, the magnet assembly includes a pair of magnets attached to a frame.

In some implementations, the frame includes two U-shaped members that cooperate to form the cavity.

In certain implementations, the radio frequency device is further operable to apply radio frequency energy to dialysis fluid in the first portion of the cartridge to excite the atoms in the dialysis fluid in the first portion of the cartridge.

In some implementations, the radio frequency device is a radio frequency coil.

In certain implementations, the dialysis system further includes a controller in communication with the radio frequency device. The controller is configured to determine a concentration of a substance in the dialysis fluid based on the received radio frequency energy generated by the excited atoms in the dialysis fluid in the first portion of the cartridge.

In some implementations, the controller is configured to determine the concentration of the substance in the dialysis fluid as a function of (i) the radio frequency energy generated by the excited atoms in the dialysis fluid in the first portion of the cartridge and (ii) a volume of the first portion of the cartridge.

In certain implementations, the dialysis fluid pump is a blood pump.

In some implementations, the dialysis fluid pump is a dialysate pump.

In certain implementations, the dialysis system further includes the cartridge.

In some implementations, the cartridge defines a first meandering fluid passageway in fluid communication with the first portion of the cartridge, and the first portion of the cartridge and the first meandering fluid passageway of the cartridge are configured to be disposed within the cavity of the magnet assembly.

In certain implementations, the first meandering fluid passageway is a U-shaped fluid passageway.

In some implementations, the cartridge is configured such that the first meandering fluid passageway is disposed outside the radio frequency device when the first portion of the cartridge is disposed in the radio frequency device.

In certain implementations, the first portion of the cartridge defines a second meandering fluid passageway.

In some implementations, the second meandering fluid passageway is a U-shaped fluid passageway.

In certain implementations, the cartridge defines a fluid inlet port via which the dialysis fluid enters the cartridge. The fluid inlet port has a first flow area and the first meandering fluid passageway has a second flow area that is smaller than the first flow area.

In some implementations, the medical fluid is dialysis fluid.

In certain implementations, the medical fluid pump is a dialysis fluid pump of a dialysis machine.

In some implementations, the medical fluid pump is a dialysis fluid pump of a dialysis machine.

In certain implementations, the magnet assembly includes a pair of magnets attached to a frame.

In some implementations, the frame includes two U-shaped members that cooperate to form the cavity.

In one aspect of the invention, a method includes reading an indicia of a medical fluid cartridge to determine a volume of a fluid passageway of the medical fluid cartridge indicated by the indicia, receiving radio frequency energy generated by excited atoms in medical fluid in the fluid passageway of the medical fluid cartridge, and determining a concentration of a substance in the medical fluid based on the determined volume of the fluid passageway of the medical fluid cartridge indicated by the indicia and the received radio frequency energy generated by the excited atoms in the medical fluid in the fluid passageway of the medical fluid cartridge.

In another aspect of the invention, a method includes determining a volume of a fluid passageway of a medical fluid cartridge and applying an indicia to the cartridge. The indicia is indicative of the determined volume of the cartridge, and the indicia is machine readable.

In an additional aspect of the invention, a method includes measuring a quantity of a first substance in a reference fluid in a reference fluid cartridge, measuring a quantity of a second substance in the reference fluid in the reference fluid cartridge, measuring a quantity of the first substance in a medical fluid in a medical fluid cartridge, measuring a quantity of the second substance in the medical fluid in the medical fluid cartridge, and determining a concentration of the second substance in the medical fluid based on the measured quantities of the first and second substances in the reference fluid and the medical fluid.

Implementations can include one or more of the following features.

In certain implementations, the method further includes determining an actual volume of the fluid passageway of the medical fluid cartridge and applying the indicia to the medical fluid cartridge. The indicia is indicative of the determined actual volume of the fluid passageway of the medical fluid cartridge.

In some implementations, determining the actual volume of the fluid passageway of the medical fluid cartridge includes measuring the actual volume of the fluid passageway of the medical fluid cartridge.

In certain implementations, the actual volume of the fluid passageway of the medical fluid cartridge is measured using a contact probe.

In some implementations, the actual volume of the fluid passageway of the medical fluid cartridge is measured using a laser.

In certain implementations, the indicia of the medical fluid cartridge is read by a machine.

In some implementations, the machine is a barcode reader and the indicia is a barcode.

In certain implementations, the radio frequency energy generated by the excited atoms in the medical fluid in the fluid passageway of the medical fluid cartridge is received by a sensor assembly.

In some implementations, prior to determining the concentration of the substance in the medical fluid, the sensor assembly is used to determine a concentration of the substance in a reference fluid in a reference fluid cartridge and the sensor assembly is calibrated based on the determined concentration of the substance in the reference fluid in the reference fluid cartridge.

In certain implementations, calibrating the sensor assembly includes comparing the concentration of the substance in the reference fluid in the reference fluid cartridge as determined by the sensor assembly to a known concentration of the substance in the reference fluid in the reference fluid cartridge.

In some implementations, the sensor assembly includes a magnet assembly that defines a cavity and is configured to generate a magnetic field within the cavity, and the sensor assembly includes a radio frequency device that is disposed in the cavity of the magnet assembly and is configured to receive the radio frequency energy generated by the excited atoms in the medical fluid in the fluid passageway of the medical fluid cartridge.

In certain implementations, the method further includes exciting the atoms in the medical fluid in the fluid passageway of the medical fluid cartridge by applying radio frequency energy to the medical fluid in the fluid passageway of the medical fluid cartridge.

In some implementations, the radio frequency energy generated by the excited atoms in the medical fluid in the fluid passageway of the medical fluid cartridge is received by a radio frequency device surrounding the fluid passageway of the medical fluid cartridge.

In certain implementations, the method further includes applying radio frequency energy to the medical fluid in the fluid passageway of the medical fluid cartridge to excite the atoms in the medical fluid in the fluid passageway of the medical fluid cartridge. Applying the radio frequency energy to the medical fluid in the fluid passageway of the medical fluid cartridge includes activating the radio frequency device.

In some implementations, the radio frequency device is a radio frequency coil.

In certain implementations, the radio frequency coil is operated in a transmit mode while applying the radio frequency energy to the medical fluid in the fluid passageway of the medical fluid cartridge, and the radio frequency coil is operated in a receiving mode while receiving the radio frequency energy generated by the excited atoms in the medical fluid in the fluid passageway of the medical fluid cartridge.

In some implementations, operating the radio frequency coil in the transmit mode includes applying electrical energy to the radio frequency coil and operating the radio frequency coil in the receive mode includes ceasing the application of electrical energy to the radio frequency coil.

In certain implementations, the method further includes adjusting the concentration of the substance in the medical fluid if the determined concentration of the substance in the medical fluid falls outside of a desired range.

In some implementations, the medical fluid is dialysis fluid.

In certain implementations, the dialysis fluid is blood.

In some implementations, the dialysis fluid is dialysate.

In certain implementations, the substance is sodium.

In some implementations, determining the volume of the fluid passageway of the medical fluid cartridge includes measuring the volume of the fluid passageway of the medical fluid cartridge.

In certain implementations, the volume of the fluid passageway of the medical fluid cartridge is measured using a contact probe.

In some implementations, the volume of the fluid passageway of the medical fluid cartridge is measured using a laser.

In certain implementations, the indicia is a barcode.

In some implementations, the medical fluid cartridge is a dialysis fluid cartridge.

In certain implementations, the dialysis fluid cartridge is a blood cartridge.

In some implementations, the dialysis fluid cartridge is a dialysate cartridge.

In certain implementations, concentrations of the first and second substances in the reference fluid are known.

In some implementations, a concentration of the first substance in the medical fluid is known.

In certain implementations, measuring the quantities of the first and second substances in the reference fluid includes receiving radio frequency energy generated by excited atoms in the reference fluid in the reference fluid cartridge, and measuring the quantities of the first and second substances in the medical fluid includes receiving radio frequency energy generated by excited atoms in the medical fluid in the medical fluid cartridge.

In some implementations, the method further includes exciting the atoms in the reference fluid by applying radio frequency energy to the reference fluid in the reference fluid cartridge, and exciting the atoms in the medical fluid by applying radio frequency energy to the medical fluid in the medical fluid cartridge.

In certain implementations, the radio frequency energy generated by the excited atoms in the reference fluid in the reference fluid cartridge is received by a radio frequency device surrounding a portion of the reference fluid cartridge, and the radio frequency energy generated by the excited atoms in the medical fluid in the medical fluid cartridge is received by a radio frequency device surrounding a portion of the medical fluid cartridge.

In some implementations, a single radio frequency device receives the radio frequency energy generated by the excited atoms in the reference fluid in the reference fluid cartridge and the radio frequency energy generated by the excited atoms in the medical fluid in the medical fluid cartridge.

In certain implementations, the single radio frequency device is a radio frequency coil.

In some implementations, the radio frequency coil is operated at a first frequency to measure the quantities of the first substance in the reference fluid and the medical fluid and is operated at a second frequency to measure the quantities of the second substance in the reference fluid and the medical fluid.

In certain implementations, the method further includes exciting the atoms in the reference fluid by applying radio frequency energy to the reference fluid in the reference fluid cartridge by activating the radio frequency device that receives the radio frequency energy generated by the excited atoms in the reference fluid in the reference fluid cartridge, and exciting the atoms in the medical fluid by applying radio frequency energy to the medical fluid in the medical fluid cartridge by activating the radio frequency device that receives the radio frequency energy generated by the excited atoms in the medical fluid in the medical fluid cartridge.

In some implementations, a single radio frequency device receives the radio frequency energy generated by the excited atoms in the reference fluid in the reference fluid cartridge and the medical fluid in the medical fluid cartridge and applies the radio frequency energy to the reference fluid in the reference fluid cartridge and the medical fluid in the medical fluid cartridge.

In certain implementations, the single radio frequency device is a radio frequency coil.

In some implementations, the radio frequency coil is operated at a first frequency to measure the quantities of the first substance in the reference fluid and the medical fluid and is operated at a second frequency to measure the quantities of the second substance in the reference fluid and the medical fluid.

In certain implementations, the radio frequency energy generated by the excited atoms in the reference fluid in the reference fluid cartridge and the radio frequency energy generated by the excited atoms in the medical fluid in the medical fluid cartridge is received by a sensor assembly.

In some implementations, prior to determining the concentration of the second substance in the medical fluid, the sensor assembly is used to determine a concentration of one of the first and second substances in the reference fluid in the reference fluid cartridge and the sensor assembly is calibrated based on the determined concentration of the one of the first and second substances in the reference fluid in the reference fluid cartridge.

In certain implementations, calibrating the sensor assembly includes comparing the concentration of the one of the first and second substances in the reference fluid in the reference fluid cartridge as determined by the sensor assembly to a known concentration of the one of the first and second substances in the reference fluid in the reference fluid cartridge.

In some implementations, the sensor assembly includes a magnet assembly that defines a cavity and is configured to generate a magnetic field within the cavity, and the sensor assembly includes a radio frequency device that is disposed in the cavity of the magnet assembly and is configured to receive the radio frequency energy generated by the excited atoms in the medical fluid in the medical fluid cartridge.

In certain implementations, the radio frequency device is a dual tuned radio frequency coil.

In some implementations, the method further includes adjusting the concentration of the second substance in the medical fluid if the determined concentration of the second substance in the medical fluid falls outside of a desired range.

In certain implementations, the first substance is hydrogen and the second substance is sodium.

In some implementations, the medical fluid is dialysis fluid.

In certain implementations, the dialysis fluid is blood.

In some implementations, the dialysis fluid is dialysate.

In certain implementations, the reference fluid is a saline solution having a known concentration of hydrogen and sodium.

In some implementations, the second substance of the medical fluid is sodium.

In one aspect of the invention, a circuit includes a radio frequency coil tuned to at least one frequency and at least one switching circuit directly connected to the radio frequency coil. The radio frequency coil is characterized by a high impedance.

In another aspect of the invention, a dialysis machine includes a dialysis fluid pump, a radio frequency coil tuned to at least one frequency, and at least one switching circuit directly connected to the radio frequency coil. The radio frequency coil is characterized by a high impedance.

Implementations can include one or more of the following features.

In certain implementations, the high impedance is an impedance of greater than 10K ohms.

In some implementations, the at least one switching circuit isolates a first set of components for transmitting signals from a second set of components for receiving signals.

In certain implementations, the at least one switching circuit includes at least one high voltage transistor.

In some implementations, the at least one high voltage transistor includes a transistor which maintains a switching state when a voltage of at least 100 volts is applied to an input.

In certain implementations, a low noise amplifier is directly connected to the at least one switching circuit.

In some implementations, the circuit includes a low noise amplifier characterized by an impedance that is ten times the impedance of the radio frequency coil.

In certain implementations, the radio frequency coil is tuned to both a first frequency and a second frequency, where the first frequency is a frequency of sodium molecules and the second frequency is a frequency of hydrogen molecules.

In some implementations, the circuit includes a first set of components for receiving signals at the first frequency and a second set of components for receiving signals at the second frequency.

In certain implementations, the first frequency is 6.5 to 11 megahertz and the second frequency is 25 to 42 megahertz.

In some implementations, the dialysis fluid pump is a blood pump.

In certain implementations, the dialysis machine is a hemodialysis machine.

In one aspect of the invention, a nuclear magnetic resonance device includes a support frame, a first magnet connected to the support frame, a second magnet connected to the support frame in a manner such that the second magnet is disposed within the magnetic field of the first magnet and a magnetic attraction exists between the first magnet and the second magnet, and a spacer disposed between the first magnet and the second magnet. The spacer is configured to maintain a space between the first magnet and the second magnet. The spacer includes a first side that faces the first magnet and a second side that is opposed to the first side and faces the second magnet. The spacer has a shape that orients the first magnet relative to the second magnet in a manner such that a pole face of the first magnet is maintained substantially parallel to a pole face of the second magnet.

In another aspect of the invention, a dialysis system includes a dialysis fluid circuit and a device for measuring a concentration of a substance in a sample of dialysate fluid taken from the dialysis fluid circuit. The device includes a support frame, a first magnet connected to the support frame, a second magnet connected to the support frame in a manner such that the second magnet is disposed within the magnetic field of the first magnet and a magnetic attraction exists between the first magnet and the second magnet, and a spacer disposed between the first magnet and the second magnet. The spacer includes a first side that contacts the first magnet and a second side that is opposed to the first side and contacts the second magnet. The first side and the second side define therebetween an interior space configured to receive the sample. The device also includes a radio frequency coil supported on the spacer so as enclose a portion of the interior space. The radio frequency coil is configured to transmit a radio frequency signal to and receive a radio frequency signal from the sample. The spacer has a peripheral shape that orients the first magnet relative to the second magnet in a manner such that a pole face of the first magnet is maintained substantially parallel to a pole face of the second magnet.

In a further aspect of the invention, a device for measuring a concentration of a substance in a sample includes a magnet support structure including a first frame member and a second frame member, a first magnet supported on the first frame member, and a second magnet supported on the second frame member in such a way that a magnetic attraction exists between the first magnet and the second magnet. The magnet support structure supports the first magnet in a spaced apart relationship relative to the second magnet such that the first frame member the second frame member cooperate to substantially surround both the first magnet and the second magnet. A first air gap exists between the first magnet and the second magnet, a second air gap exists between the first frame member and the second frame member, and a third air gap exists between the first frame member and the second frame member at a location spaced apart from the first air gap and the second air gap.

In an additional aspect of the invention, a device for measuring a concentration of a substance in a sample includes a first frame portion having a U-shape including a first frame base, a first frame arm extending from one end of the first frame base in a direction perpendicular to the first frame base, and a second frame arm extending from another end of the first frame base in a direction perpendicular to the first frame base. The device also includes a second frame portion having a U-shape including a second frame base, a third frame arm extending from one end of the second frame base in a direction perpendicular to the second frame base, and a fourth frame arm extending from another end of the second frame base in a direction perpendicular to the second frame base. A first magnet is connected to the first frame base and resides between the first frame arm and the second frame arm. A second magnet is connected to the second frame base and resides between the third frame arm and the fourth frame arm. The second magnet disposed within the magnetic field of the first magnet in such a way that a magnetic attraction exists between the first magnet and the second magnet. The first frame portion is arranged relative to the second frame portion in a manner such that a free end of the first frame arm faces a free end of the third frame arm and is spaced apart from the third frame arm, and a free end of the second frame arm faces a free end of the fourth frame arm and is spaced apart from the fourth frame arm.

In yet another aspect of the invention, a dialysis system includes a dialysis fluid circuit, and a device for measuring a concentration of a substance in a sample. The device includes a magnet support structure including a first frame member and a second frame member. A first magnet is supported on the first frame member, and a second magnet is supported on the second frame member in such a way that a magnetic attraction exists between the first magnet and the second magnet. The magnet support structure supports the first magnet in a spaced apart relationship relative to the second magnet such that the first frame member and second frame member cooperate to substantially surround both the first magnet and the second magnet. A first air gap exists between the first magnet and the second magnet, a second air gap exists between the first frame member and the second frame member, and a third air gap exists between the first frame member and the second frame member at a location spaced apart from the first air gap and the second air gap.

In another aspect of the invention, a nuclear magnetic resonance device includes a first magnet, a second magnet disposed adjacent to the first magnet in such a way that a first space exists between the first magnet and the second magnet and an attractive magnetic field exists in the space, and a radio frequency coil assembly disposed in the space. The radio frequency coil assembly is configured to transmit a radio frequency signal to, and receive a radio frequency signal from, a sample disposed in the space. A first non-magnetic, electrically-conductive member is disposed between the radio frequency coil assembly and the first magnet, and a second non-magnetic, electrically-conductive member is disposed between the radio frequency coil assembly and the second magnet.

In a further aspect of the invention, a device for measuring a concentration of a substance in a sample includes a first magnet, a second magnet disposed within the magnetic field of the first magnet in such a way that a magnetic attraction exists between the first magnet and the second magnet, and a spacer disposed between the first magnet and the second magnet. The spacer is configured to maintain a space between the first magnet and the second magnet. The spacer includes a spacer first side that faces the first magnet and a spacer second side that is opposed to the spacer first side and faces the second magnet. The spacer first side and the spacer second side define therebetween a recess that is configured to receive the sample. A radio frequency coil is supported by the spacer so as to surround at least a portion of the recess. The radio frequency coil is configured to transmit a radio frequency signal to, and receive a radio frequency signal from, the sample. A first non-magnetic, electrically-conductive plate is disposed between the spacer first side and the first magnet, and a second non-magnetic, electrically-conductive plate is disposed between the spacer second side and the second magnet.

In another aspect of the invention, a dialysis system includes a dialysis fluid circuit and a device for measuring a concentration of a substance in a sample. The device includes a first magnet, a second magnet disposed within the magnetic field of the first magnet in such a way that a magnetic attraction exists between the first magnet and the second magnet, and a spacer disposed between the first magnet and the second magnet. The spacer is configured to maintain a space between the first magnet and the second magnet, and the spacer defines a recess configured to receive the sample. A radio frequency coil is supported by the spacer within the magnetic field and is configured to transmit a radio frequency signal to, and receive a radio frequency signal from, the sample. A first non-magnetic, electrically-conductive member is disposed between the radio frequency coil and the first magnet, and a second non-magnetic, electrically-conductive member is disposed between the radio frequency coil and the second magnet.

In some implementations, the first side contacts the first magnet, and the second side contacts the second magnet.

In certain implementations, the first side and the second side define therebetween an interior space configured to receive a test sample.

In some implementations, the first side of the spacer and the second side of the spacer are planar, and a plane defined by the first side of the spacer is substantially parallel to a plane defined by the second side of the spacer.

In certain implementations, the pole face of the first magnet is angled relative to the pole face of the second magnet by no more than 0.2 degrees.

In some implementations, the spacer is formed of a ceramic material.

In certain implementations, the spacer includes a pair of non-magnetic, electrically-conductive plates, and the spacer is sandwiched between the pair of plates such that a first surface of a first plate of the pair of plates contacts the first magnet, and a surface opposed to the first surface of the first plate contacts a first side of the spacer, and a first surface of a second plate of the pair of plates contacts the second magnet, and a surface opposed to the first surface of the second plate contacts a second side of the spacer.

In some implementations, the first side and the second side define therebetween an interior space, and the device further includes a radio frequency coil supported on the spacer so as enclose a portion of the interior space. The radio frequency coil is configured to transmit a radio frequency signal to and receive a radio frequency signal from the interior space.

In certain implementations, the radio frequency coil has an impedance that is at least 10 K ohms.

In some implementations, the radio frequency coil is a dual tuned radio frequency coil configured to be switchable between operation at a first frequency and operation at a second frequency.

In certain implementations, the first side of the spacer includes a first groove and a first support plate disposed in the first groove such that an outward facing surface of the first support plate lies flush with the spacer first side, the second side of the spacer includes a second groove and a second support plate disposed in the second groove such that an outward facing surface of the second support plate lies flush with the spacer second side, and each of the first support plate and the second support plate includes a through opening that is configured to receive and support the radio frequency coil within the interior space.

In some implementations, the first support plate and the second support plate are formed of a sodium-free plastic.

In certain implementations, the radio frequency coil includes a hollow rectangular form and an electrical conductor that is wound about a coil axis, and the radio frequency coil is oriented within the spacer such that the coil axis is generally parallel to the spacer first side and transverse to flux lines associated with the magnetic attraction force of the two magnets.

In some implementations, the spacer is clamped between the magnets due to the magnetic attractive force.

In certain implementations, the first magnet includes a first pole piece, the second magnet includes a second pole piece, the first side of the spacer contacts the first pole piece, and the second side of the spacer contacts the second pole piece.

In some implementations, the spacer includes a spacer body including a spacer body first side and a spacer body second side. The spacer body defines an internal space. The spacer also includes a first support plate that is disposed in a first groove formed in the spacer body first side and includes a first opening, a second support plate that is disposed in a second groove formed in the spacer body second side and includes a second opening that is aligned with the first opening, a radio frequency coil assembly disposed within the first opening and the second opening such that a portion of the internal space is enclosed by the radio frequency coil assembly, a first electrically conductive shield plate disposed on the spacer body first side, and a second electrically conductive shield plate disposed on the spacer body second side.

In certain implementations, the dialysis system further includes a dialysis machine including a compartment, and a module that can be disposed in the compartment. The module includes the device.

In some implementations, the device further includes a spacer disposed between the first magnet and the second magnet. The spacer is configured to maintain first air gap between the first magnet and the second magnet.

In certain implementations, the device further includes a spacer disposed between the first magnet and the second magnet. The spacer is configured to maintain a space between the first magnet and the second magnet. The spacer includes a first side that faces the first magnet and a second side that is opposed to the first side and faces the second magnet. The spacer has a shape that orients the first magnet relative to the second magnet in a manner such that a pole face of the first magnet is maintained substantially parallel to a pole face of the second magnet.

In some implementations, the spacer includes a spacer body including a spacer body first side and a spacer body second side. The spacer body defines an internal space. The spacer further includes a first support plate that is disposed in a first groove formed in the spacer body first side and includes a first opening, a second support plate that is disposed in a second groove formed in the spacer body second side and includes a second opening that is aligned with the first opening, a radio frequency coil assembly disposed within the first opening and the second opening such that a portion of the internal space is enclosed by the radio frequency coil assembly, a first electrically conductive shield plate disposed on the spacer body first side, and a second electrically conductive shield plate disposed on the spacer body second side.

In certain implementations, the device further includes a radio frequency coil disposed in the first air gap between the first magnet and the second magnet. The radio frequency coil is configured to transmit a radio frequency signal to, and receive a radio frequency signal from, the sample when the sample is disposed within the radio frequency coil.

In some implementations, the radio frequency coil has an impedance of at least 10 K ohms.

In certain implementations, the radio frequency coil is a dual tuned radio frequency coil configured to be switchable between operation at a first frequency and operation at a second frequency.

In some implementations, the main air gap has a dimension corresponding to the distance between the first magnet and the second magnet, and the dimension is in a range of 20 mm to 30 mm.

In certain implementations, the second air gap and the third air gap have a dimension corresponding to the distance between the first frame member and the second frame member, and the dimension is in a range of 0.5 mm to 2.0 mm.

In some implementations, the first magnet includes a first magnet assembly including the first magnet and a first pole piece disposed on a pole face of the first magnet, and the second magnet includes a second magnet assembly including the second magnet and a second pole piece disposed on a pole face of the second magnet.

In certain implementations, the dialysis system further includes a dialysis machine including a compartment, and a module that can be disposed in the compartment. The module includes the device for measuring a concentration of a substance in a sample.

In some implementations, the first member and the second member are formed of metal.

In certain implementations, the first member and the second member are formed of copper.

In some implementations, the first member and the second member have a skin depth corresponding to an operating frequency of the radio frequency coil, and the first member and the second member have a thickness that is at least equal to the skin depth, where the thickness corresponds to the dimension of the first member and the second member in a direction parallel to the magnetic field.

In certain implementations, the first member and the second member have a shape that corresponds to the shape of a pole face of the first magnet and the second magnet.

In some implementations, the device further includes a spacer disposed in the space and configured to maintain the space between the first magnet and the second magnet. The spacer includes a spacer first side that contacts the first magnet and a spacer second side that is opposed to the spacer first side and contacts the second magnet. The spacer first side and the spacer second side define therebetween a recess that is configured to receive the sample.

In certain implementations, the first side of the spacer and the second side of the spacer are planar, and a plane defined by the first side of the spacer is substantially parallel to a plane defined by the second side of the spacer.

In some implementations, the radio frequency coil has an impedance of at least 10 K ohms.

In certain implementations, the radio frequency coil is a dual tuned radio frequency coil configured to be switchable between operation at a first frequency and operation at a second frequency.

In some implementations, the device includes a spacer disposed in the space and configured to maintain the space between the first magnet and the second magnet. The spacer includes a first side including a first groove and a first support plate disposed in the first groove such that an outward facing surface of the first support plate lies flush with the spacer first side, and a second side including a second groove and a second support plate disposed in the second groove such that an outward facing surface of the second support plate lies flush with the spacer second side. Each of the first support plate and the second support plate includes a through opening that is configured to receive and support the radio frequency coil within the space.

In certain implementations, the first support plate and the second support plate are formed of a sodium-free plastic.

In some implementations, the radio frequency coil includes a hollow rectangular form and an electrical conductor that is wound about a coil axis, and the radio frequency coil is oriented within the spacer such that the coil axis is generally parallel to the spacer first side and transverse to flux lines associated with the magnetic attraction force of the two magnets.

In certain implementations, the device includes a magnet support structure including a first frame member and a second frame member, where the first magnet is supported on the first frame member, the second magnet is supported on the second frame member, and the magnet support structure supports the first magnet and second magnet in a manner such that the first frame member and second frame member cooperate to substantially surround both the first magnet and the second magnet, the first space exists between the first magnet and the second magnet, a second space exists between the first frame member and the second frame member, and a third space exists between the first frame member and the second frame member at a location spaced apart from the first space and the second air space.

In some implementations, the dialysis system further includes a dialysis machine including a compartment, and a module that can be disposed in the compartment. The module includes the device.

In one aspect of the invention, a medical fluid cartridge includes a body including a first portion defining a first fluid passageway and a second portion defining a second fluid passageway in fluid communication with the first fluid passageway. The body defines a gap between the first portion of the body and the second portion of the body such that the first portion of the body can be disposed in a radio frequency device while the second portion of the body remains outside the radio frequency device.

In another aspect of the invention, a medical fluid system includes a medical fluid pumping machine and a magnet assembly defining a cavity in which a radio frequency device is positioned. The magnet assembly is configured to generate a magnetic field within the cavity.

The medical fluid system also includes a medical fluid cartridge including a body having a first portion defining a first fluid passageway and a second portion defining a second fluid passageway in fluid communication with the first fluid passageway. The first portion of the body is configured to be disposed within the radio frequency device positioned within the cavity of the magnet assembly, and the second portion of the body is configured to be disposed within the cavity defined by the magnet assembly and to remain outside the radio frequency device.

In a further aspect of the invention, a medical fluid cartridge includes a body including a first portion defining a meandering fluid passageway extending between a fluid inlet port and a fluid outlet port and a second portion defining a fluid passageway extending between the fluid inlet port and the fluid outlet port. The meandering fluid passageway and the fluid passageway defined by the second portion are configured so that when fluid flows into the medical fluid cartridge via the fluid inlet port, a flow rate of fluid flowing through the meandering fluid passageway is less than a flow rate of fluid flowing through the fluid passageway defined by the second portion.

In an additional aspect of the invention, a medical fluid system includes a medical fluid pumping machine, a magnet assembly defining a cavity, and a medical fluid cartridge. The magnet assembly is configured to generate a magnetic field within the cavity. The medical fluid cartridge includes a body having a first portion defining a meandering fluid passageway extending between a fluid inlet port and a fluid outlet port and a second portion defining a fluid passageway extending between the fluid inlet port and the fluid outlet port. The first portion of the body is configured to be disposed within the cavity of the magnet assembly, and the meandering fluid passageway and the fluid passageway defined by the second portion are configured so that when fluid flows into the medical fluid cartridge via the fluid inlet port, a flow rate of fluid flowing through the meandering fluid passageway is less than a flow rate of fluid flowing through the fluid passageway defined by the second portion.

In some implementations, the first fluid passageway is a meandering fluid passageway.

In certain implementations, the first fluid passageway is a U-shaped fluid passageway.

In some implementations, the second fluid passageway is a meandering fluid passageway.

In certain implementations, the second fluid passageway is a U-shaped fluid passageway.

In some implementations, the first fluid passageway has a flow area that is greater than a flow area of the second fluid passageway.

In certain implementations, the flow area of the first fluid passageway is 2 to 10 times greater than the flow area of the second fluid passageway.

In some implementations, the medical fluid cartridge includes a fluid inlet port via which medical fluid enters the medical fluid cartridge and a fluid outlet port via which medical fluid exits the medical fluid cartridge.

In certain implementations, the first fluid passageway is configured such that fluid flows through the first fluid passageway at a rate that is lower than a rate at which the medical fluid flows through the fluid inlet port.

In some implementations, a flow area of the first fluid passageway is greater than a flow area of the fluid inlet port.

In certain implementations, the first fluid passageway is a meandering fluid passageway.

In some implementations, the second fluid passageway is configured such that fluid flows through the second fluid passageway at a rate that is lower than a rate at which the medical fluid flows through the fluid inlet port.

In certain implementations, a flow area of the first fluid passageway and a flow area of the second fluid passageway are greater than a flow area of the fluid inlet port.

In some implementations, the first and second fluid passageways are configured such that the rate at which fluid flows through the first fluid passageway is lower than the rate at which the medical fluid flows through the second fluid passageway.

In certain implementations, a flow area of the first fluid passageway is greater than a flow area of the second fluid passageway.

In some implementations, the first fluid passageway is a meandering fluid passageway.

In certain implementations, the second fluid passageway is configured such that fluid flows through the second fluid passageway at a rate that is lower than a rate at which the medical fluid flows through the fluid inlet port.

In some implementations, a flow area of the second fluid passageway is greater than a flow area of the fluid inlet port.

In certain implementations, the second fluid passageway is a meandering fluid passageway.

In some implementations, the second fluid passageway is a meandering fluid passageway.

In certain implementations, the body includes a third portion having a third fluid passageway.

In some implementations, the third passageway is a straight fluid passageway.

In certain implementations, the medical fluid cartridge includes a fluid inlet port via which medical fluid enters the medical fluid cartridge and a fluid outlet port via which medical fluid exits the medical fluid cartridge.

In some implementations, the third fluid passageway is configured such that fluid flows through the third fluid passageway at a rate that is lower than a rate at which the medical fluid flows through the fluid inlet port and that is greater than rates at which the medical fluid flows through the first and second fluid passageways.

In certain implementations, a flow area of the third fluid passageway is greater than a flow area of the second fluid passageway.

In some implementations, the flow area of the third fluid passageway is at least 5 times greater than the flow area of the second fluid passageway.

In certain implementations, the flow area of the third fluid passageway is 5 to 10 times greater than the flow area of the second fluid passageway.

In some implementations, the first, second, and third fluid passageways are configured so that when fluid enters the fluid inlet port, a first portion of the fluid passes through the second fluid passageway to the first fluid passageway and then to the fluid outlet port, and a second portion of the fluid passes through the third fluid passageway to the fluid outlet port.

In certain implementations, at least one of the first and second fluid passageways is a meandering fluid passageway.

In some implementations, the body includes a wall that divides the second fluid passageway from the third fluid passageway near the fluid inlet port and a wall that divides the first fluid passageway from the third fluid passageway near the fluid outlet port.

In certain implementations, the body of the medical fluid cartridge includes a base and a cover attached to the base, the base and the cover cooperating to define the first and second fluid passageways.

In some implementations, the medical fluid cartridge includes indicia that indicates a volume of the first fluid passageway.

In certain implementations, the indicia is machine-readable.

In some implementations, the indicia includes a barcode.

In certain implementations, the medical fluid cartridge is a dialysis fluid cartridge.

In some implementations, the dialysis fluid cartridge is a blood cartridge.

In certain implementations, the dialysis fluid cartridge is a dialysate cartridge.

In some implementations, the gap between the first portion of the body and the second portion of the body allows the first portion of the body to be disposed in a radio frequency coil while the second portion of the body remains outside the radio frequency coil.

In certain implementations, the magnet assembly is part of the medical fluid pumping machine.

In some implementations, the magnet assembly is part of a module that is releasably attached to a housing of the medical fluid pumping machine.

In certain implementations, the magnet assembly includes a pair of magnets attached to a frame.

In some implementations, the frame includes two U-shaped members that cooperate to form the cavity.

In certain implementations, the medical fluid system further includes a medical fluid line connected to the cartridge to carry medical fluid to the cartridge.

In some implementations, the medical fluid pumping machine includes a pump that is operably connected to the medical fluid line to pump medical fluid to the cartridge.

In certain implementations, the medical fluid pumping machine is a dialysis machine.

In some implementations, the dialysis machine is a hemodialysis machine.

In certain implementations, medical fluid cartridge is removable from the cavity of the magnet assembly.

In some implementations, the meandering fluid passageway and the fluid passageway defined by the second portion are configured so that when fluid flows into the medical fluid cartridge via the fluid inlet port, the flow rate of fluid flowing through the meandering fluid passageway is 10 percent to 30 percent of the flow rate of fluid flowing through the fluid passageway defined by the second portion.

In certain implementations, a flow area of the fluid passageway defined by the second portion is 5 to 15 times greater than a flow area of the meandering fluid passageway.

In some implementations, the body is configured such that 10 percent to 30 percent by volume of the medical fluid flowing through the fluid inlet port passes through the meandering fluid passageway.

In certain implementations, the fluid passageway defined by the second portion is a substantially straight fluid passageway.

In some implementations, the body is configured such that substantially all of the medical fluid that flows through the fluid inlet and that does not pass through the meandering fluid passageway passes through the substantially straight fluid passageway.

In certain implementations, the body is configured such that 10 percent to 30 percent by volume of the medical fluid flowing through the fluid inlet port passes through the meandering fluid passageway, and 70 percent to 90 percent by volume of the medical fluid flowing through the fluid inlet port passes through the substantially straight fluid passageway.

In some implementations, the body includes a wall that divides the meandering fluid passageway from the substantially straight fluid passageway near the fluid inlet port and near the fluid outlet port.

In certain implementations, the meandering fluid passageway is a U-shaped fluid passageway.

In some implementations, the meandering fluid passageway has a first region and a second region, a flow area of the first region being greater than a flow area of the second region.

In certain implementations, the second region of the meandering fluid passageway is configured to carry fluid to the first region of the meandering fluid passageway.

In some implementations, the body of the medical fluid cartridge includes a base and a cover attached to the base, the base and the cover cooperating to define the meandering fluid passageway.

In certain implementations, the medical fluid cartridge includes indicia that indicates a volume of a first region of the meandering fluid passageway.

In some implementations, the indicia is machine-readable.

In certain implementations, the indicia includes a barcode.

In some implementations, the medical fluid cartridge is a dialysis fluid cartridge.

In certain implementations, the dialysis fluid cartridge is a blood cartridge.

In some implementations, the dialysis fluid cartridge is a dialysate cartridge.

In certain implementations, the meandering fluid passageway and the fluid passageway defined by the second portion are configured so that when fluid flows into the medical fluid cartridge via the fluid inlet port, the flow rate of fluid flowing through the meandering fluid passageway is 10 percent to 30 percent of the flow rate of fluid flowing through the fluid passageway defined by the second portion.

In some implementations, a flow area of the fluid passageway defined by the second portion is 5 to 15 times greater than a flow area of the meandering fluid passageway.

In certain implementations, the body is configured such that 10 percent to 30 percent by volume of the medical fluid flowing through the fluid inlet port passes through the meandering fluid passageway.

In some implementations, the fluid passageway defined by the second portion is a substantially straight fluid passageway.

In certain implementations, the medical system further includes a radio frequency device disposed in the cavity of the magnet assembly, and the first portion of the body of the medical fluid cartridge is configured to be disposed in the radio frequency device.

In some implementations, a second portion of the body of the medical fluid cartridge is configured to be disposed within the cavity defined by the magnet assembly and to remain outside the radio frequency device when the first portion of the body of the medical fluid cartridge is disposed in the radio frequency device.

In certain implementations, the radio frequency device is a radio frequency coil.

In some implementations, the magnet assembly is part of the medical fluid pumping machine.

In certain implementations, the magnet assembly is part of a module that is releasably attached to a housing of the medical fluid pumping machine.

In some implementations, the magnet assembly includes a pair of magnets attached to a frame.

In certain implementations, the frame includes two U-shaped members that cooperate to form the cavity.

In some implementations, the medical fluid system further includes a medical fluid line connected to the cartridge to carry medical fluid to the cartridge.

In certain implementations, the medical fluid pumping machine includes a pump that is operably connected to the medical fluid line to pump medical fluid to the cartridge.

In some implementations, the medical fluid pumping machine is a dialysis machine.

In certain implementations, the dialysis machine is a hemodialysis machine.

In some implementations, the medical fluid cartridge is removable from the cavity of the magnet assembly.

Implementations can include one or more of the following advantages.

Many of the sensor assemblies described herein are designed to carry out online measurements of the concentration of a substance in medical fluid as the medical fluid is being pumped through a medical fluid circuit during a medical treatment. This online measurement technique allows substance concentrations falling outside a desired concentration range to be detected quickly and to be quickly remedied. In certain implementations, the sensor assembly is used to carry out online measurements of a sodium concentration in a patient's blood during hemodialysis treatment. These measurements can be used to quickly determine when the sodium concentration of the patient's blood falls outside of a desired concentration range and to quickly adjust the patient's blood sodium concentration when such a condition occurs. For example, in response to determining that the sodium concentration of the patient's blood falls outside of a desired concentration range, the sodium content in the dialysate can be adjusted to cause an adjustment of the sodium concentration of the patient's blood. Quickly adjusting the blood sodium concentration in this manner can prevent the patient's blood sodium concentrations from falling outside a desired concentration range for a significant period of time and can thus reduce the likelihood of the patient feeling discomfort resulting from a blood sodium concentration that is too high or too low.

Many of the sensor assemblies described herein can be used to determine the concentration of a substance in a medical fluid with greater accuracy than sensors, such as conductivity sensors, that have traditionally been used to determine the concentration of a substance in a medical fluid. In some implementations, the sensor assemblies can measure the blood sodium to an accuracy of less than +/3 mM with a measurement time of only a few minutes. As a result, systems employing many of the sensor assemblies described herein can monitor and maintain the concentration of the substance in the medical fluid with greater accuracy than many conventional systems. In implementations in which the sensor assemblies are used in hemodialysis systems to measure the sodium concentration in a patient's blood, the increased accuracy of the sensor can ensure that the patient's blood sodium levels are maintained within a desired concentration range with greater accuracy, which reduces the likelihood of the patient feeling discomfort resulting from a blood sodium concentration that is too high or too low.

Advantageously, many of the sensor assemblies described herein can be implemented for a much lower cost than some conventional spectroscopic analysis devices including nuclear magnetic resonance (NMR) technology. This can be achieved in part due to the type of measurement made using the sensor assemblies described herein. In many conventional spectroscopic NMR devices, a very strong and homogeneous magnetic field is required for resolving very tiny frequency differences between atoms, which in turn requires relatively large and expensive magnets. Since the sensor assemblies described herein are typically used to determine an amount of only one or two particular substances in a sample, the magnetic field requirements of the sensor assemblies are less stringent than some conventional spectroscopic NMR devices. Cost reductions can also be obtained because the sensor assemblies described herein typically do not require electronic or mechanical shimming to obtain a sufficiently homogeneous magnetic field.

In some implementations, a relatively simple and lightweight structure permits the sensor assembly to provide a desired level of magnetic field homogeneity by arranging two magnets so that their respective pole faces are spaced apart and parallel. In certain implementations, a spacer is positioned between the magnets to ensure that the respective magnet pole faces are parallel to a sufficient tolerance. Since the spacer, rather than the support structure, is relied upon to ensure that the pole faces of the magnets are parallel, the support structure can be simple and lightweight relative to many conventional NMR magnet support structures, such as many conventional C-core magnet support structures.

In certain implementations, the sensor assembly includes a spacer assembly having shield plates to address eddy currents that tend to form in pole pieces of the magnet assembly during operation of the RF device and can in turn result in acoustic ringing in a gap between magnets of the magnet assembly. The shield plates are formed of a non-magnetic, electrically conductive material (e.g., copper). Since the shield plate material is not magnetic, the shield plates do not become saturated. In addition, since the shield plate material is electrically conductive, the shield plate skin depth tends to be small, which permits the use of thin plates and reduces or minimizes the size of the overall assembly. In addition, the small skin depth can result in lower electrical losses, and can thus increase the sensitivity of the RF device.

In some implementations, the sensor assembly includes an isolation circuit that can be switched between a transmitting mode (when the RF device is transmitting RF energy) and a receiving mode (when the RF device is receiving RF energy). In the transmitting mode, receiving components are isolated from high voltages associated with the transmission of the RF energy. Similarly, in the receiving mode, transmitting components are isolated from low voltage receiving components. This arrangement allows low voltage electronic components to be placed on the circuit without risk of damage.

Some of the medical fluid cartridges described herein are designed to slow the flow of medical fluid through the cartridge and/or to lengthen a flow path of medical fluid through the cartridge. The slower flow rate and/or lengthened flow path can increase or maximize the amount of time that the medical fluid spends flowing through the magnet assembly (i.e., the magnetic field generated by the magnet assembly) and the RF device of the system. Thus, this cartridge design permits the use of a magnet assembly that is smaller and less expensive than magnet assemblies found in many traditional NMR sensors. The reduced size and cost of the magnet assembly makes it cost-feasible to use NMR sensor assemblies of the type described herein in medical fluid pumping machines (e.g., hemodialysis machines).

In certain implementations, the cartridge includes a fluid passageway that directs medical fluid through a magnetic field generated by the system before the medical fluid reaches a portion of the cartridge in which RF energy is applied to and received from the medical fluid. For example, the fluid passageway can be a meandering fluid passageway that is positioned within the magnetic field generated by the system but outside the RF device (e.g., an RF coil) of the system during use. The design of this fluid passageway can help to ensure that the medical fluid travels within the magnetic field for a sufficient period of time to polarize atoms (e.g., sodium atoms) of the medical fluid, which helps to ensure that those atoms can be accurately detected and counted as the medical fluid passes through the portion of the cartridge in which the RF energy is applied to and received from the medical fluid.

In certain implementations, the cartridge includes a fluid passageway that bypasses the fluid passageway through which the medical fluid to be analyzed flows. This bypass fluid passageway can be straight and can have a greater flow area than the fluid passageway carrying the medical fluid to be tested. This arrangement can ensure that a significant volume (e.g., at least 70 percent by volume) of the medical fluid entering the cartridge is allowed to pass through the cartridge at a high flow rate. The straightness of the bypass fluid passageway and the high flow rate of the medical fluid passing through the bypass fluid passageway can help to ensure that the medical fluid passes through the cartridge without damage to the medical fluid. In implementations in which the medical fluid is blood, for example, the design of the bypass fluid passageway can help to ensure that the blood flows through the cartridge without clotting and without damage to the various components of the blood. The high flow rate of the medical fluid passing through the bypass fluid passageway can also allow the medical fluid pump of the system to be operated at a constant speed without placing excessive burden on the medical fluid pump.

In some implementations, rather than detecting the concentration of a substance in a medical fluid while the medical fluid is flowing through the cartridge, the medical fluid is diverted to a chamber of a cartridge where the medical fluid remains static or stagnant while being tested. Testing a static sample of medical fluid in this way can increase the ease with which the concentration of a substance in the medical fluid can be determined. For example, it is unnecessary to account for a flow rate of the medical fluid when determining the concentration of the substance when the sample is static. In certain cases, testing a static sample of medical fluid in this way may result in a more accurate determination of the concentration of the substance in the medical fluid.

In certain implementations, sensor assemblies described herein can be used to indirectly determine the concentration of a substance (e.g., sodium) in the blood of a patient. For example, the sensor assembly can be positioned along a dialysate circuit of a hemodialysis system to measure the concentration of sodium in the dialysate. By comparing the concentration of sodium in the fresh dialysate (i.e., the dialysate that has not yet passed through a dialyzer of the system along with the patient's blood) to the concentration of sodium in the spent dialysate (i.e., the dialysate that has passed through the dialyzer along with the patient's blood), it is possible to determine the concentration of sodium in the patient's blood. This technique permits sodium levels in the patient's blood to be determined without diverting any blood from the extracorporeal blood line set of the hemodialysis system to a blood cartridge. As a result, this technique can make it easier to maintain a desired constant blood flow rate within the extracorporeal blood line set. Further, the samples of fresh and spent dialysate that are analyzed in this manner can be static samples, which can increase the ease, and in some cases the accuracy, with which the concentration of sodium within the fresh and spent dialysate is determined.

In implementations in which samples of fresh and spent dialysate are analyzed to indirectly determine the concentration of a substance (e.g., sodium) in a patient's blood, the medical fluid cartridge into which the fresh and spent dialysate samples are directed for analysis can be reusable from patient to patient since the dialysate delivered to the medical fluid cartridge does not come into contact with a patient's blood. This allows a relatively expensive, precisely machined medical fluid cartridge to be used, which can permit accurate concentrations of substances in the dialysate to be determined without having to account for variations in the volume of one medical fluid cartridge to the next or discrepancies between the actual volume of the medical fluid cartridge and the intended volume of the medical fluid cartridge.

In certain implementations, a volume of the medical fluid cartridge (e.g., a volume of the portion of the fluid passageway of the medical fluid cartridge that holds the medical fluid to which RF energy is applied and from which RF energy is received during analysis) is determined with a high level of accuracy and this volume can be used to accurately determine the concentration of a substance in the medical fluid. This technique permits the medical fluid cassette, which may be a single-use disposable component, to be formed with a lower precision (e.g., a precision typical of injection molding), which allows the medical fluid cassette to be manufactured in a cost feasible manner without significantly impacting the accuracy with which the concentration of the substance in the medical fluid can be determined. For example, the actual volume of the medical fluid cassette may differ slightly from the intended volume and, in the case of mass production of such medical fluid cartridges, the actual volume of one medical fluid cartridge to the next may differ slightly without significantly impacting the concentration detected by the sensor assembly when used with those medical fluid cartridges since the actual volume of each medical fluid cartridge will be determined and used to determine the concentration of the substance in the medical fluid.

In some implementations, the sensor assembly is used to detect a concentration of a substance (e.g., sodium) in a reference fluid (e.g., a reference fluid contained in a reference fluid cartridge) prior to detecting the concentration of that substance in the medical fluid in the medical fluid cartridge. The actual concentration of the substance in the reference fluid is known. Therefore, the concentration of the substance in the reference fluid that is detected by the sensor assembly can be used to calibrate the sensor assembly. This is advantageous since the sensitivity of the sensor assembly may change from treatment to treatment due to changing conditions, such as slight changes in the uniformity of the magnetic field generated by the sensor assembly (i.e., generated by the magnet assembly of the sensor assembly), trace amounts of the substance to be measured (e.g., sodium) in the system, etc.

In some implementations, hydrogen and a second substance (e.g., sodium) are detected in a reference fluid in a reference fluid cartridge. Hydrogen and the second substance are also detected in a saline solution and a medical fluid sample (e.g., a blood sample), respectively, in a medical fluid cartridge. The detected readings of the quantities or concentrations of the hydrogen and the second substance in the reference fluid, saline solution, and medical fluid sample can then be compared to accurately determine the concentration of the second substance in the medical fluid sample. For example, the ratio of the detected reading of the second substance to the detected reading of hydrogen in the reference fluid can be compared to the ratio of the detected reading of the second substance in the medical fluid sample to the detected reading of hydrogen in the saline solution and that information can be used to accurately determine the concentration of the second substance in the medical fluid. Advantageously, such a technique can be used to determine the concentration of the second substance in the medical fluid sample without knowing the volume of the medical fluid cartridge in which the medical fluid sample resides when analyzed because the hydrogen concentrations in the reference fluid and the medical fluid are the same and the ratios of the detected reading of the second substance to the detected reading of hydrogen in the fluids are not dependent on the volumes of the cartridges. In other words, a difference between those determined ratios can be attributed to a difference in the concentrations of the second substance in the reference fluid and the medical fluid sample and can be used to determine the actual concentration of the second substance in the medical fluid sample.

In certain implementations, a reference cartridge containing a reference fluid of the type described above is provided with the sensor assembly. In addition to allowing the sensor assembly to be calibrated in the manner discussed above, the reference fluid cartridge can help to prevent damage to the magnet assembly. For example, the reference fluid cartridge can be stored within the magnet assembly between uses and can thus reduce the risk of unintended objects (e.g., magnetic objects) being inserted into and trapped within the magnet assembly.

Other aspects, features, and advantages will be apparent from the detailed description, the drawings, and the claims.

(with the shield plates of the spacer assembly omitted), illustrating an opening through which a portion of the blood cartridge can be inserted into an internal space of the spacer assembly and the RF coil assembly.

Figure 9:
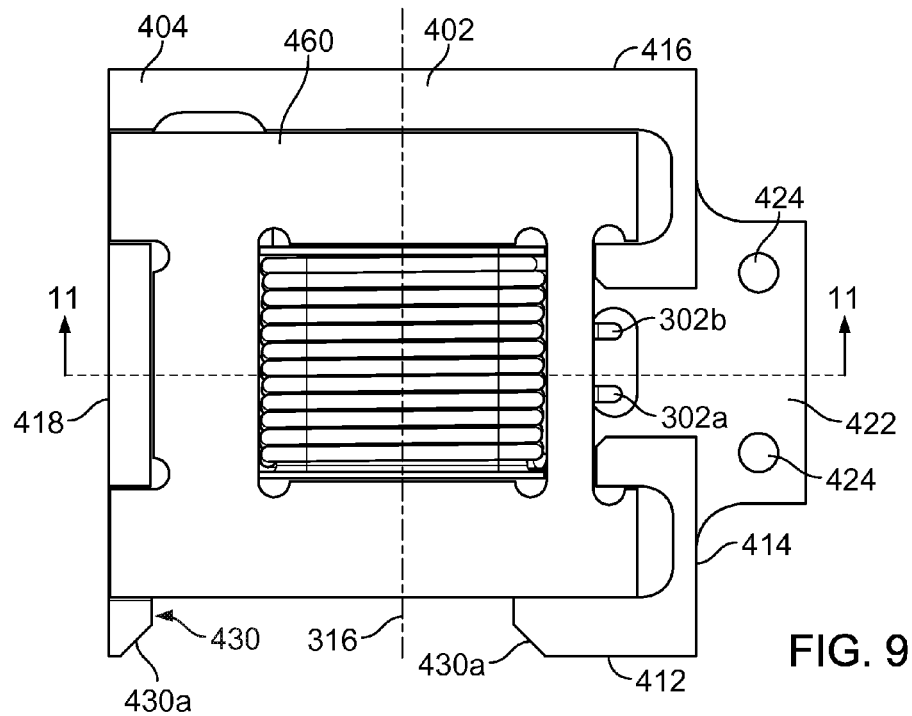
FIG. 9 is a top view of the spacer assembly and RF coil assembly of the NMR sensor assembly of FIG. 3 with shield plates of the spacer assembly omitted to better illustrate interior components of the spacer assembly.
Figure 10:
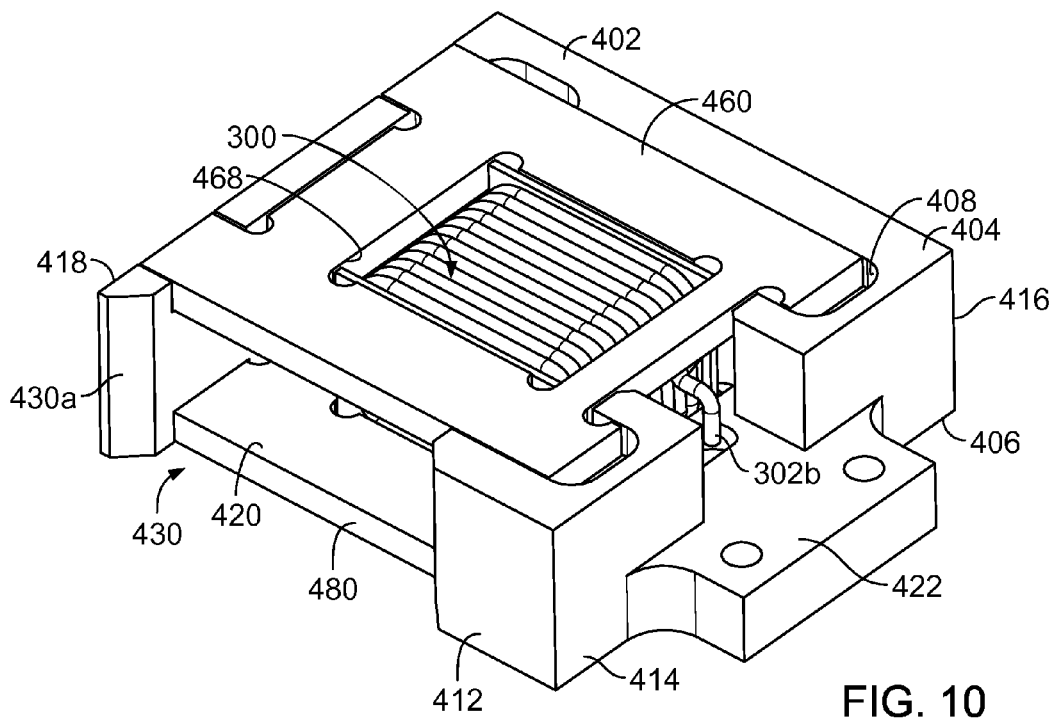
FIG. 10 is a perspective view of the spacer assembly and RF coil assembly of the NMR sensor assembly of FIG. 3
Figure 11:
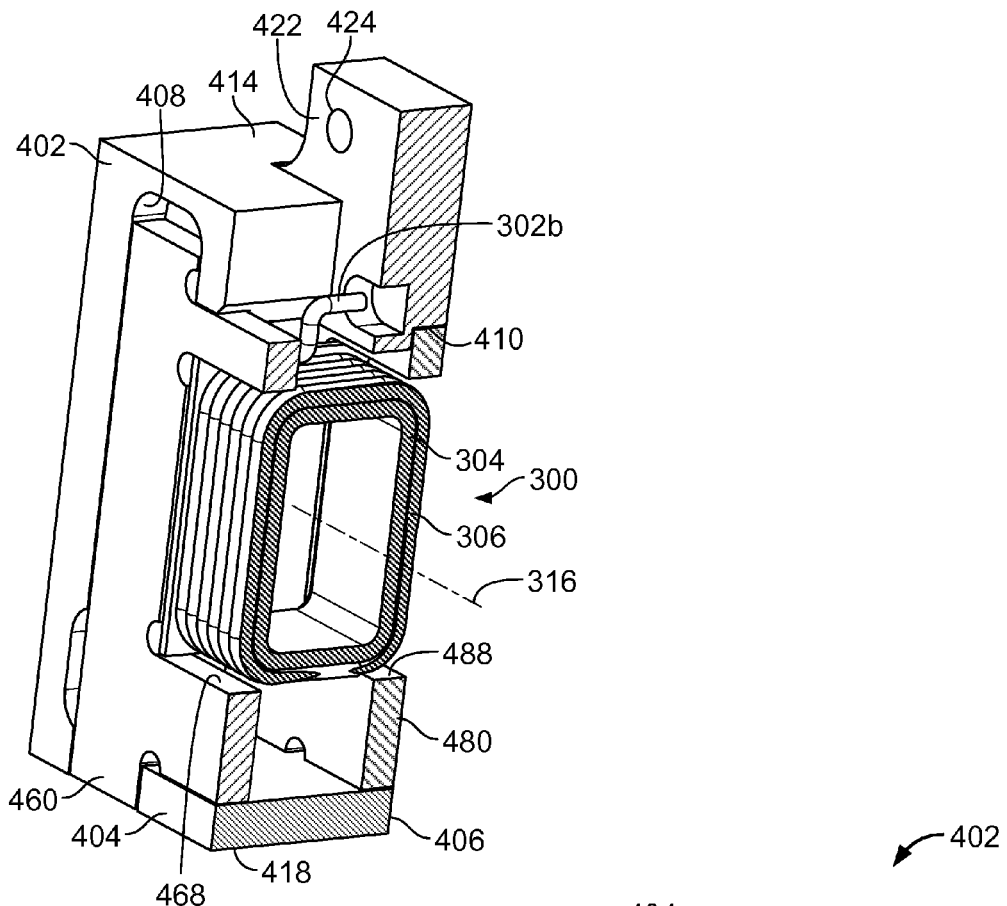

FIG. 11 is a perspective cross-sectional view of the spacer assembly and RF coil assembly along line 11-11 in FIG. 9, illustrating the RF coil assembly supported by support plates so as to surround a portion of the spacer assembly internal space into which a portion of the blood cartridge can be inserted during use.

Figure 6:
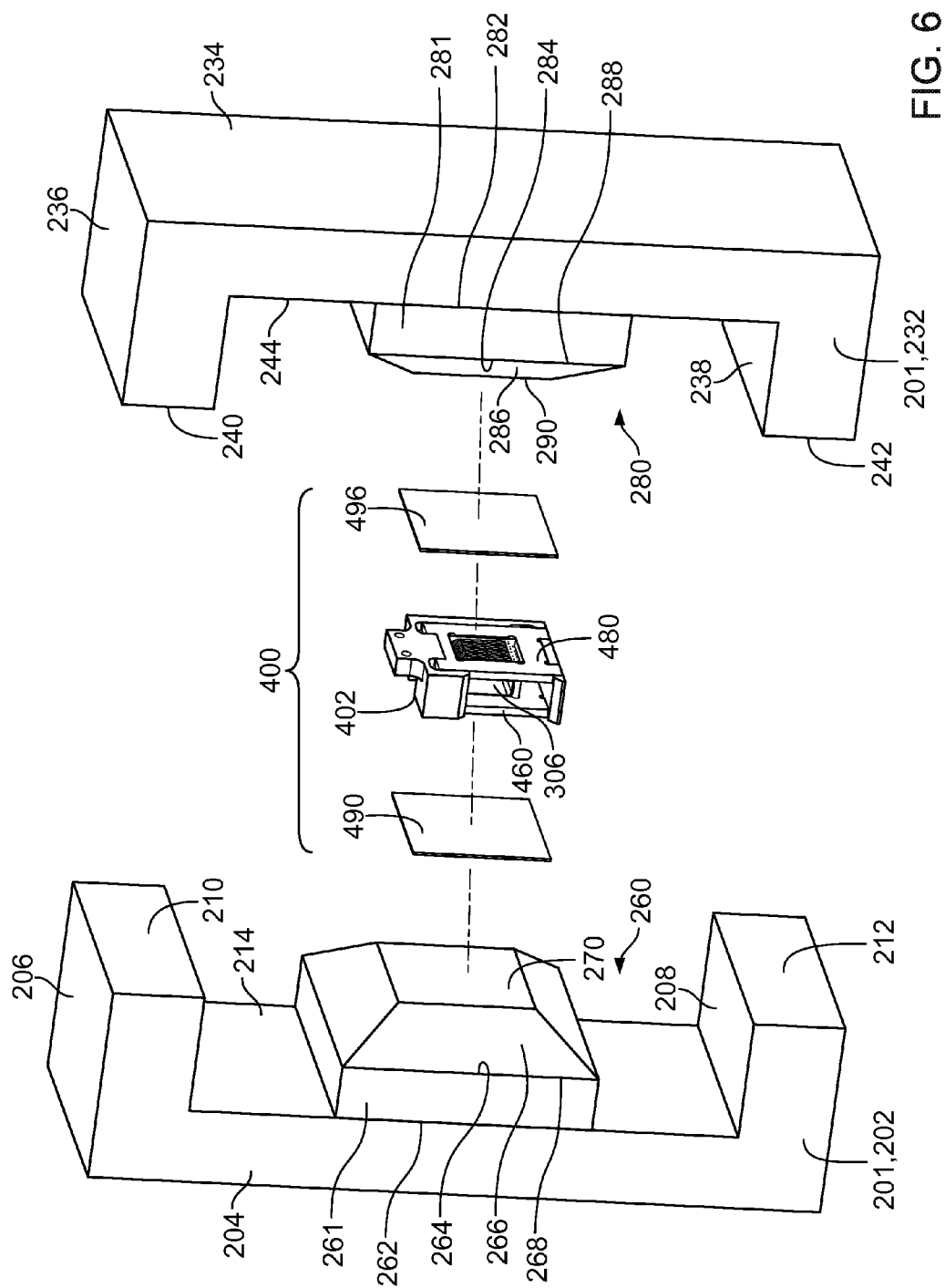
FIG. 6 is an exploded perspective view of the support frame, the magnet units, and a spacer assembly of the NMR sensor assembly of FIG. 3.
Figure 12:
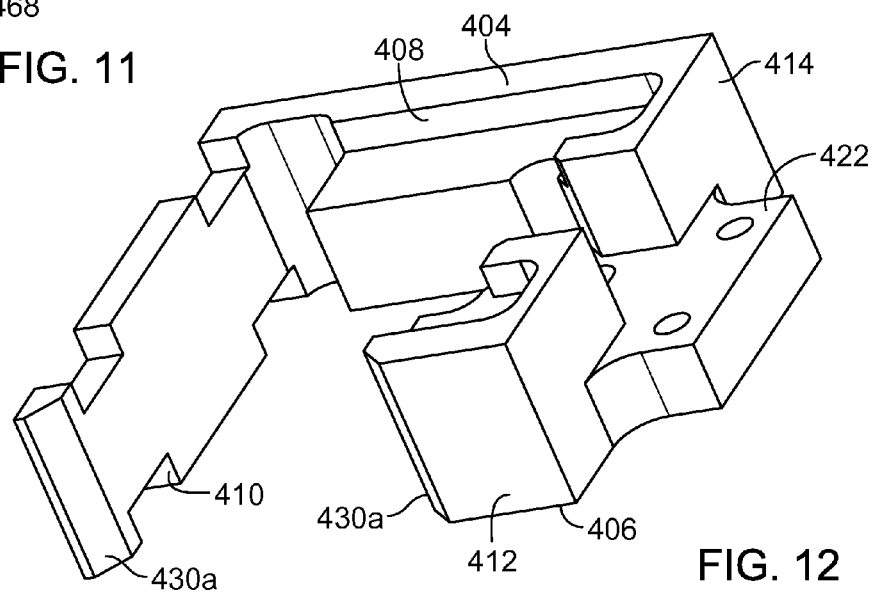

FIG. 12 is a perspective view of a first side of a spacer body of the spacer assembly of FIG. 6.

Figure 13:
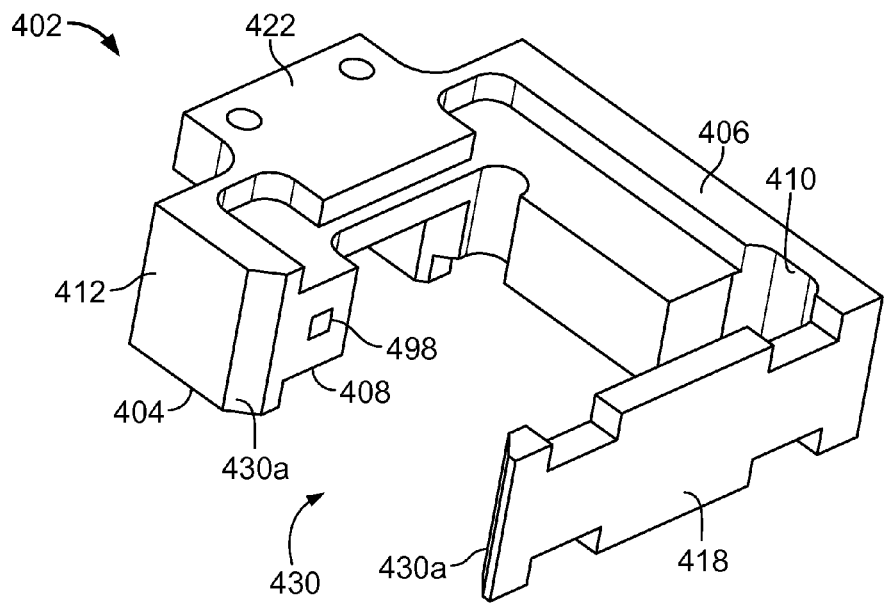

FIG. 13 is a perspective view of a second side of the spacer body of the spacer assembly of FIG. 6.

Figure 14:
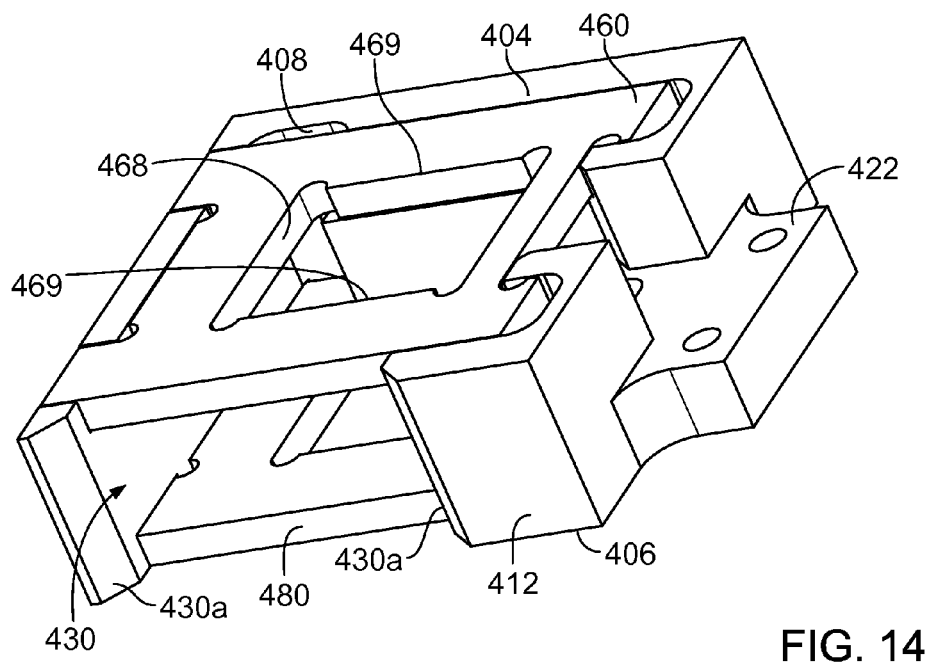

FIG. 14 is a perspective view of the first side of the spacer body of the spacer assembly of FIG. 6, illustrating support plates assembled with the spacer body.

Figure 15:
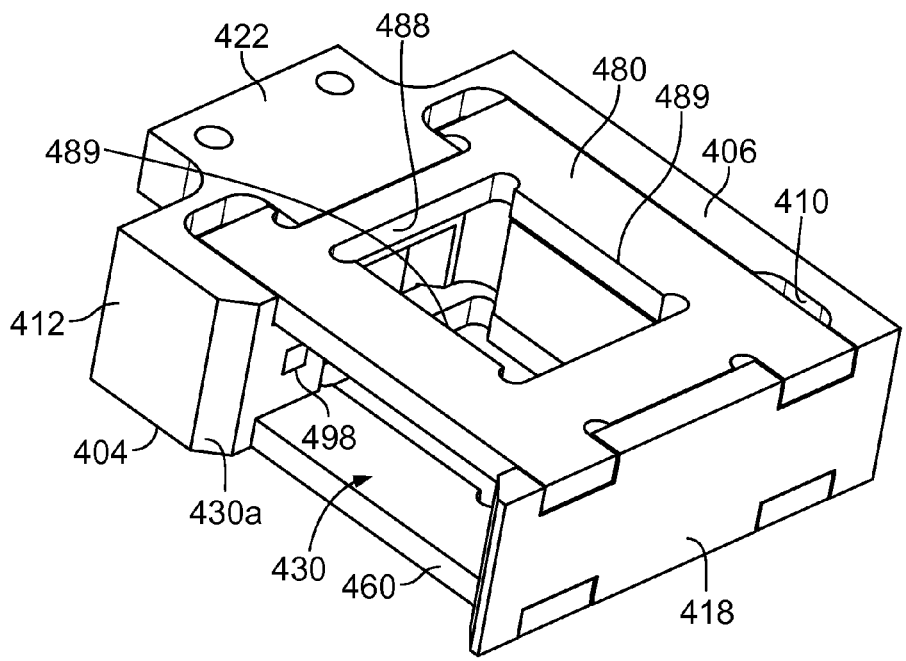

FIG. 15 is a perspective view of the second side of the spacer body of the spacer assembly of FIG. 6, illustrating support plates assembled with the spacer body.

Figure 3:
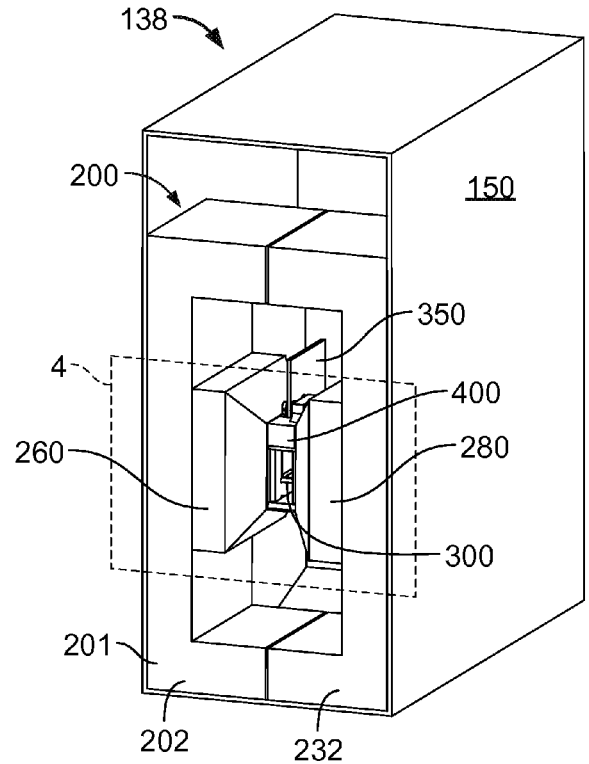
FIG. 3 is a perspective view of the NMR module of FIG. 1 isolated from the dialysis machine. A cover plate of the NMR module has been omitted to better illustrate an internal NMR sensor assembly of the NMR module.
Figure 16:
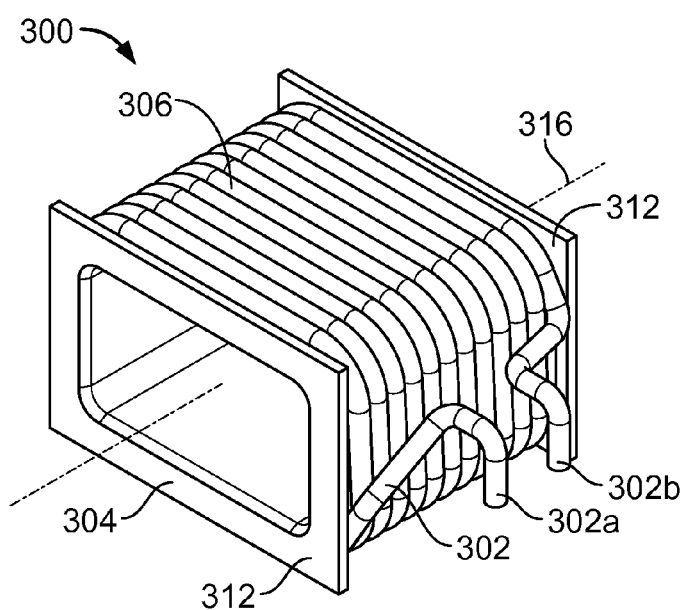

FIG. 16 is a perspective view of the RF coil assembly of the NMR sensor assembly of FIG. 3.

Figure 17:
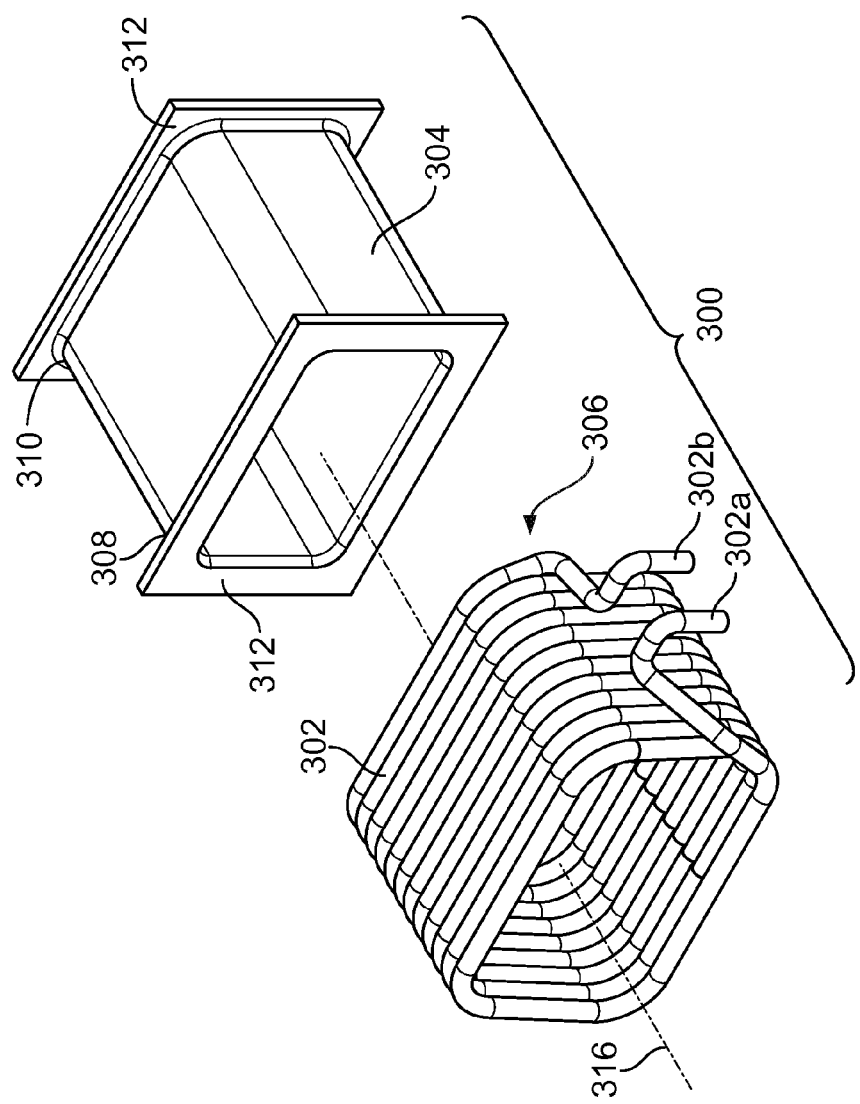

FIG. 17 is an exploded perspective view of the RF coil assembly of FIG. 16.

Figure 18:
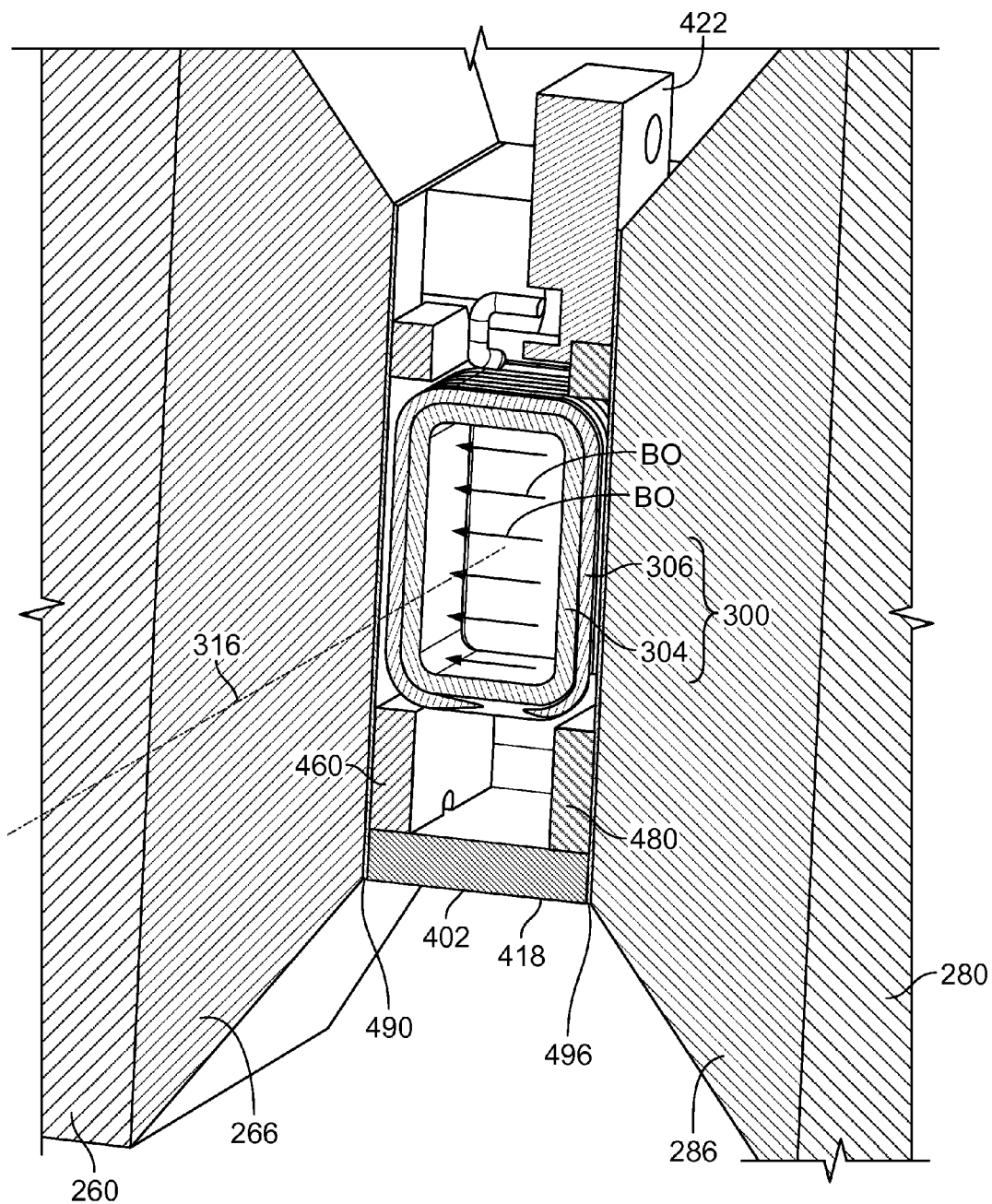

FIG. 18 is a perspective cross-sectional view of the RF coil assembly when assembled within the NMR sensor assembly of FIG. 3, illustrating the transverse orientation of the RF coil axis relative to the magnetic field B0 generated by the magnet units.

Figure 19:
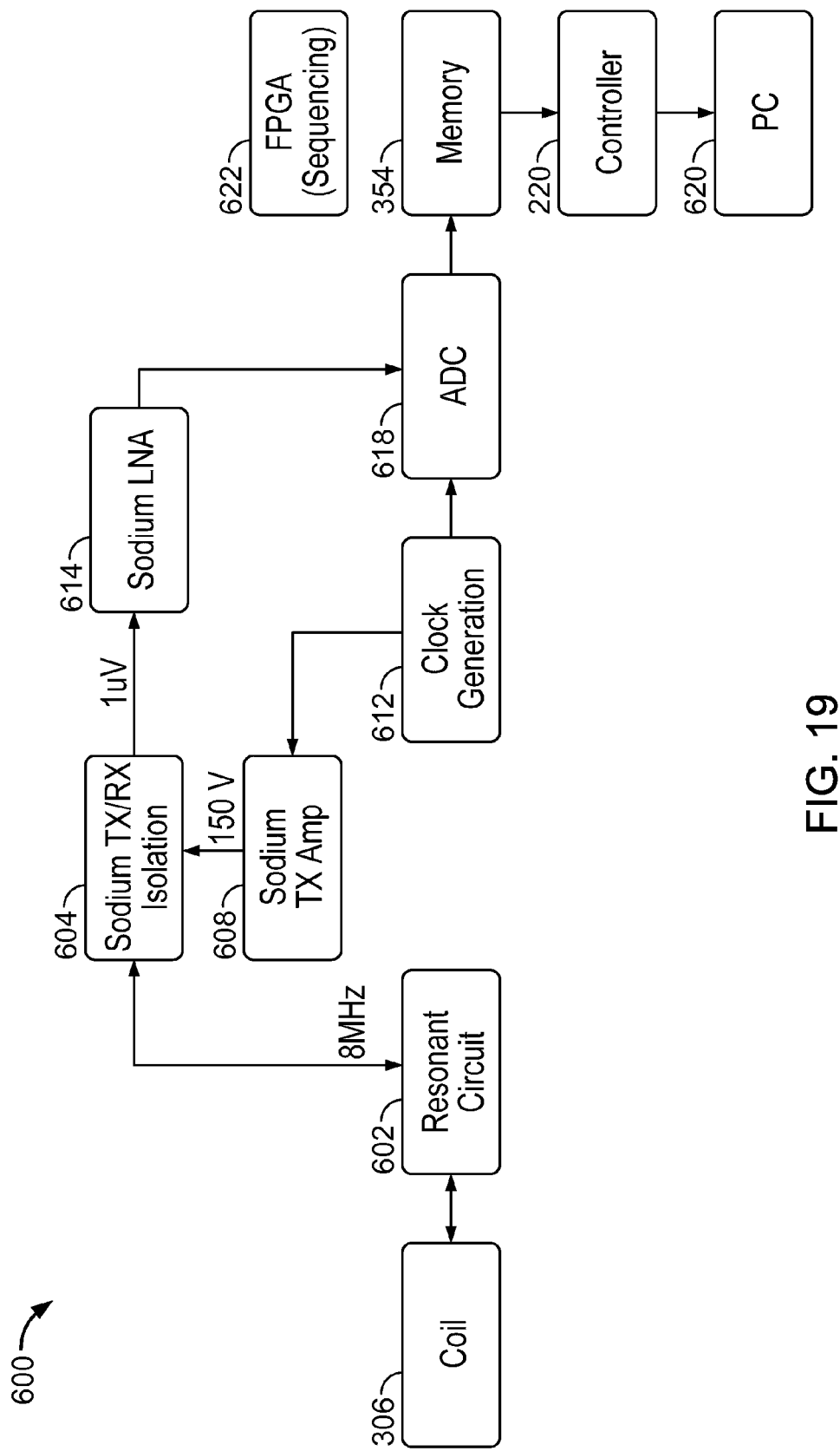

FIG. 19 shows a block diagram of a circuit used to operate the NMR sensor assembly of FIG. 3.

Figure 20:
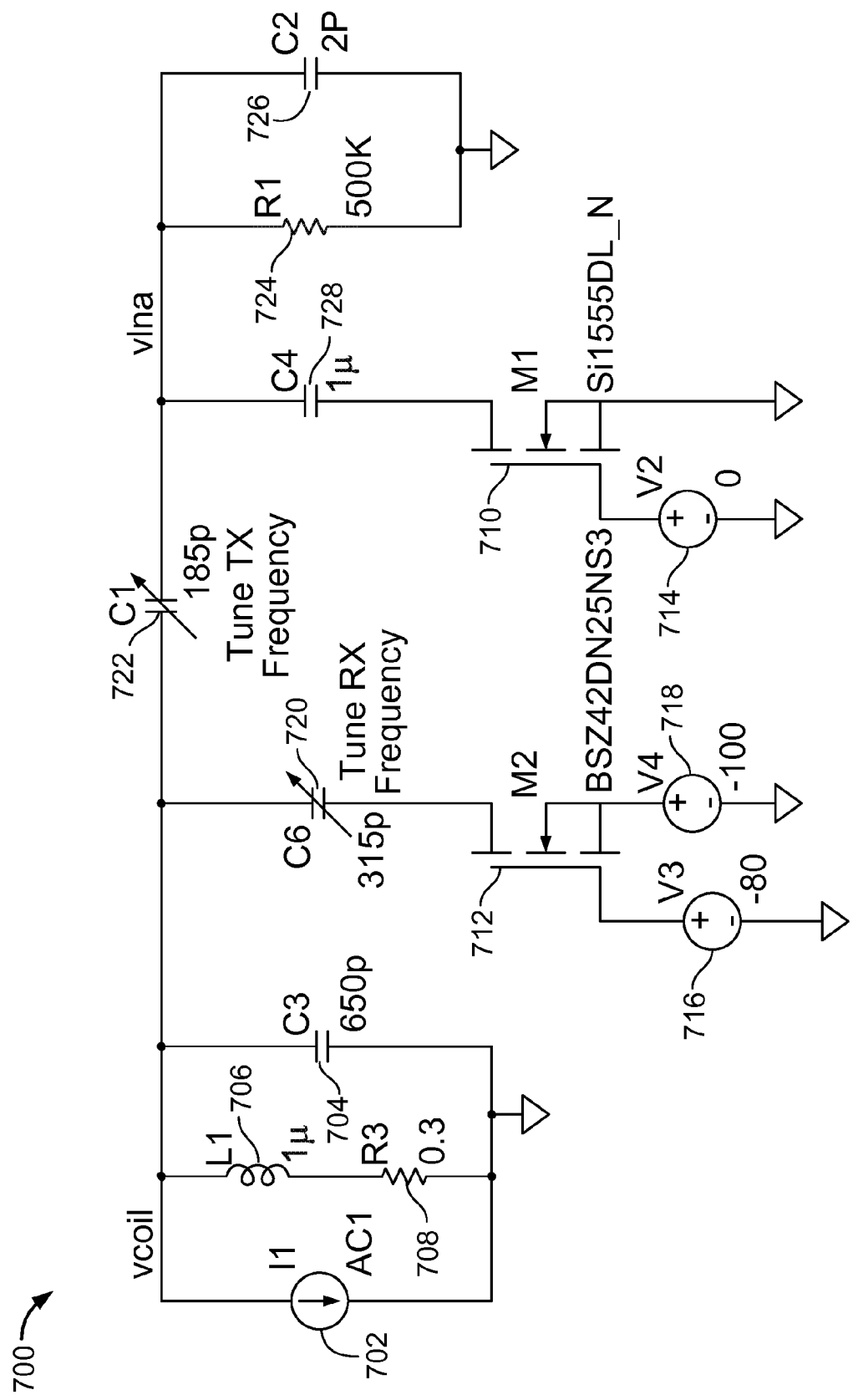
Figure 21:
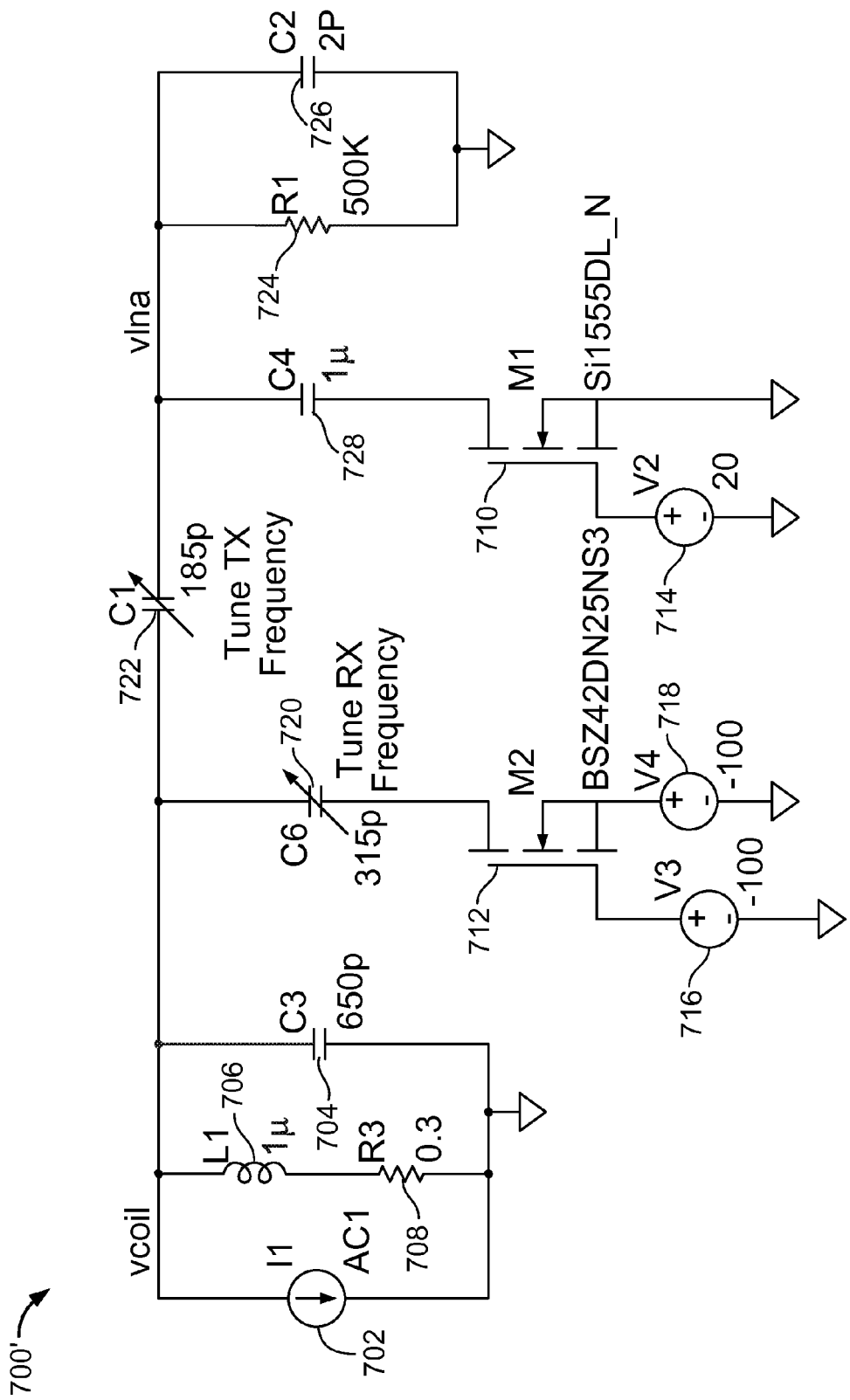

FIGS. 20 and 21 show a circuit implementing a portion of the functionality of the circuit shown in FIG. 19, where FIG. 20 illustrates the circuit in a receiving mode, and FIG. 21 illustrates the circuit in a transmitting mode.

Figure 22:
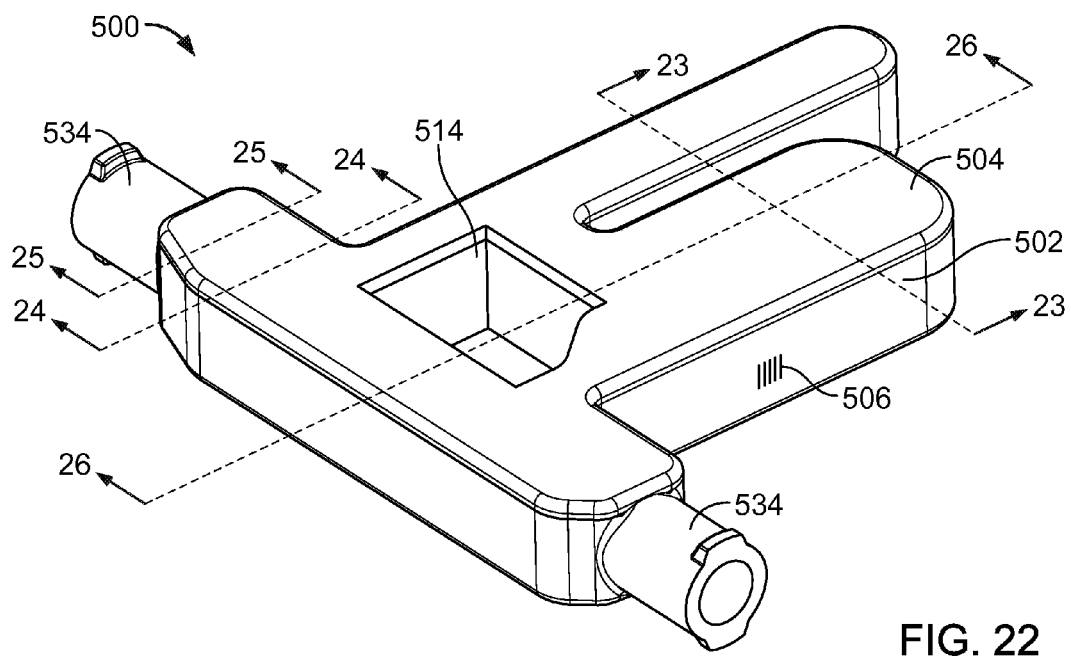

FIG. 22 is a perspective view of the blood cartridge that can be used with the NMR sensor assembly of FIG. 3.

Figure 23:
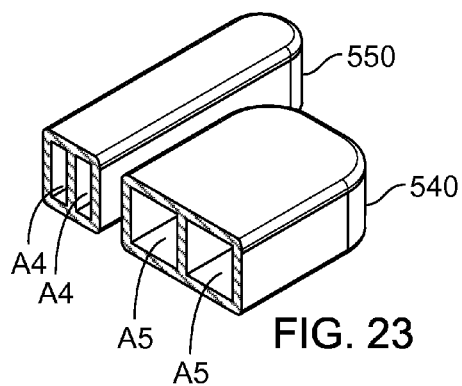

FIG. 23 is a perspective cross-sectional view of the blood cartridge as seen along line 23-23 in FIG. 22.

Figure 24:
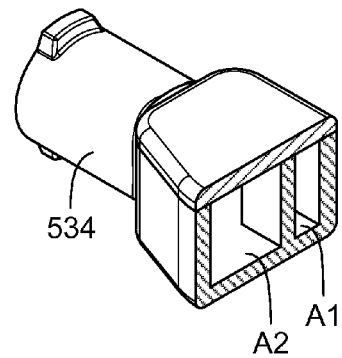

FIG. 24 is a perspective cross-sectional view of the blood cartridge as seen along line 24-24 in FIG. 22.

Figure 25:
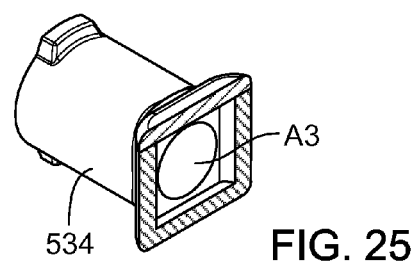

FIG. 25 is a perspective cross-sectional view of the blood cartridge as seen along line 25-25 in FIG. 22.

Figure 26:
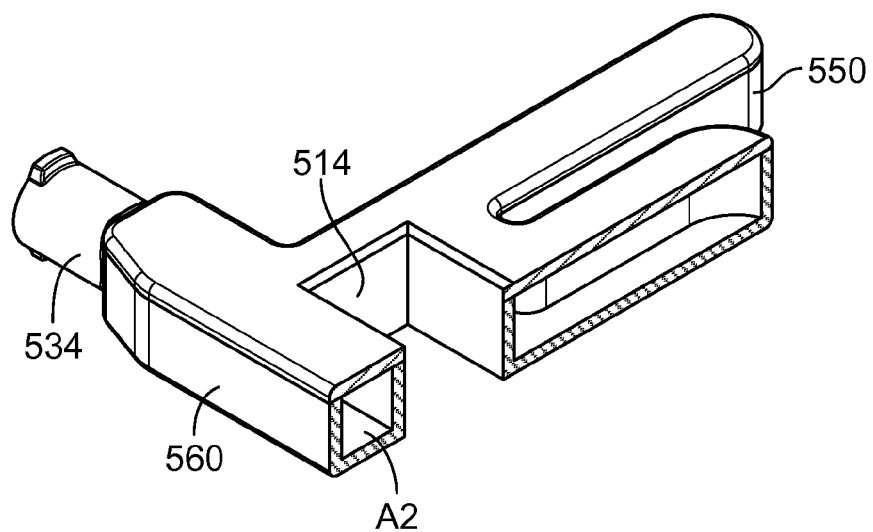

FIG. 26 is a perspective cross-sectional view of the blood cartridge as seen along line 26-26 in FIG. 22.

Figure 27:
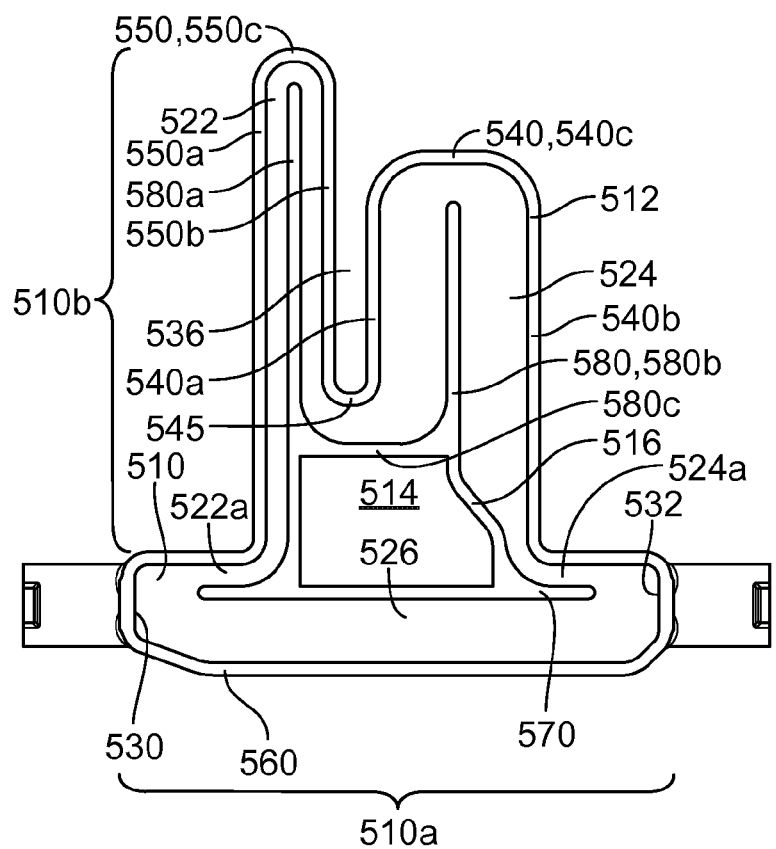

FIG. 27 is a plan view of the base of the blood cartridge of FIG. 22.

Figure 28:
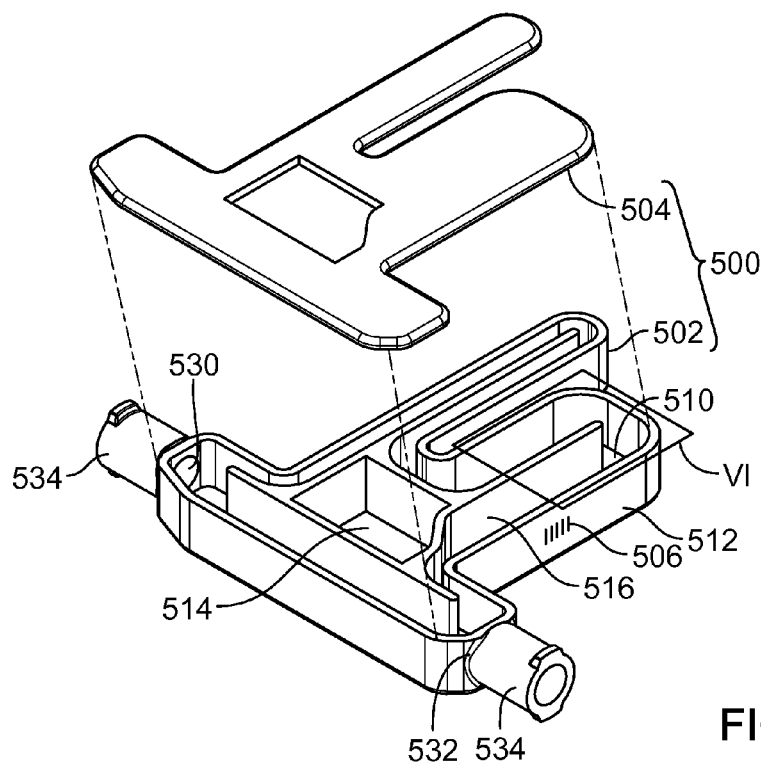

FIG. 28 is an exploded perspective view of the blood cartridge of FIG. 22.

Figure 29:
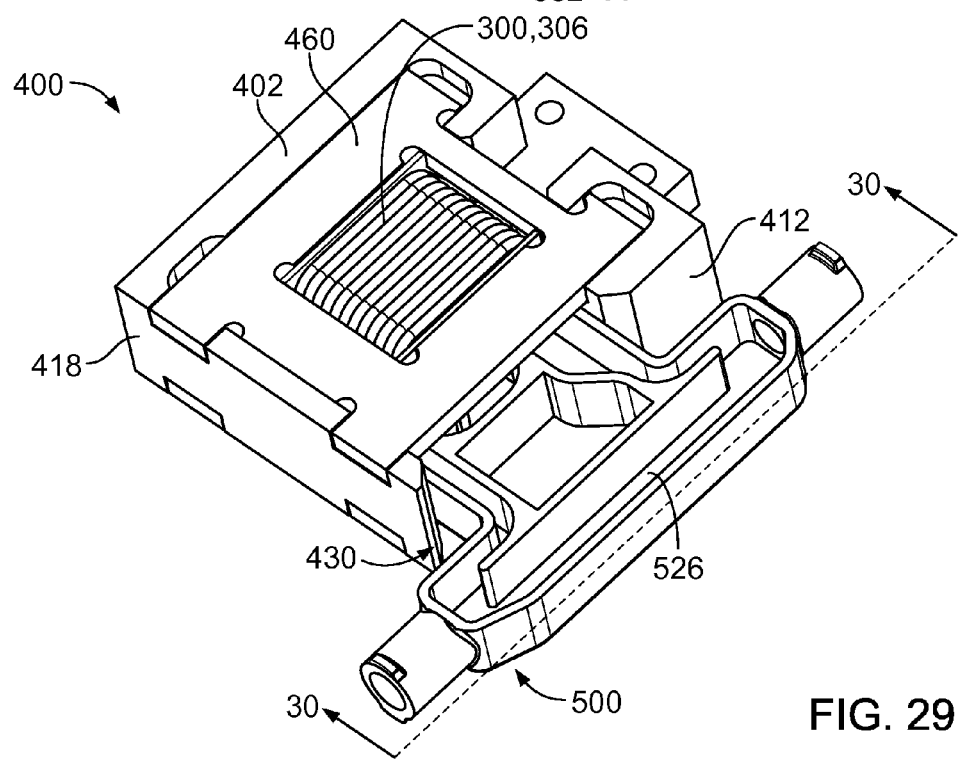

FIG. 29 is a perspective view of the blood cartridge of FIG. 22 disposed in the spacer assembly and RF coil assembly of the NMR sensor assembly of FIG. 3. The shield plates of the spacer assembly have been omitted to expose certain interior components of the spacer assembly.

Figure 30:
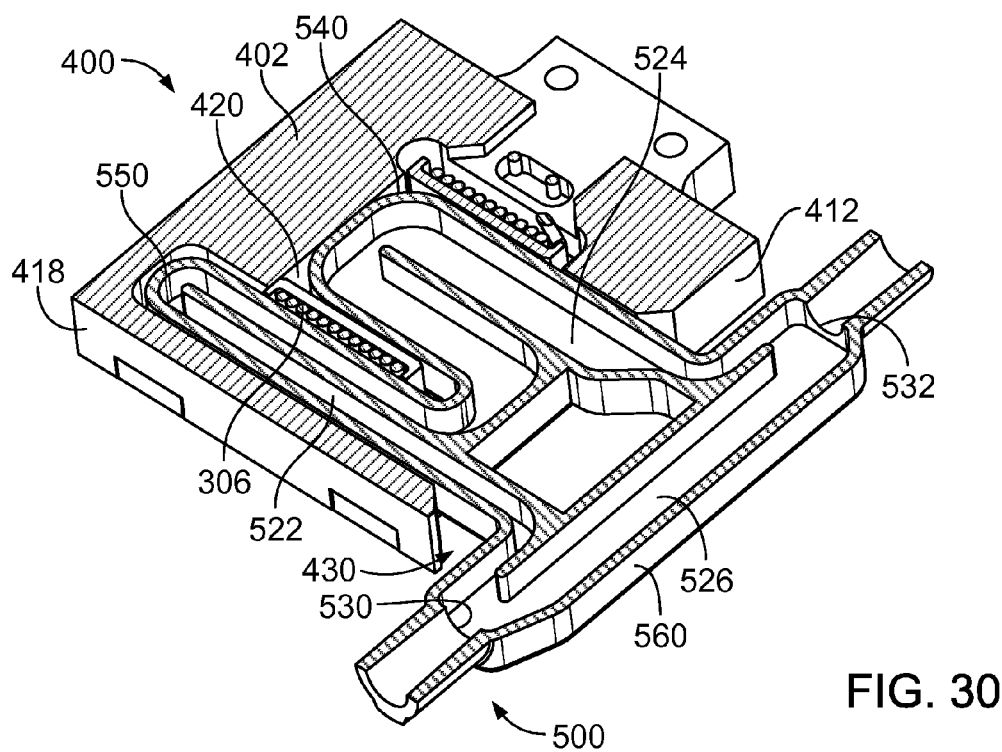

FIG. 30 is a perspective cross-sectional view of the cartridge, the spacer assembly, and the RF coil assembly as seen along line 30-30 in FIG. 29.

Figure 31:
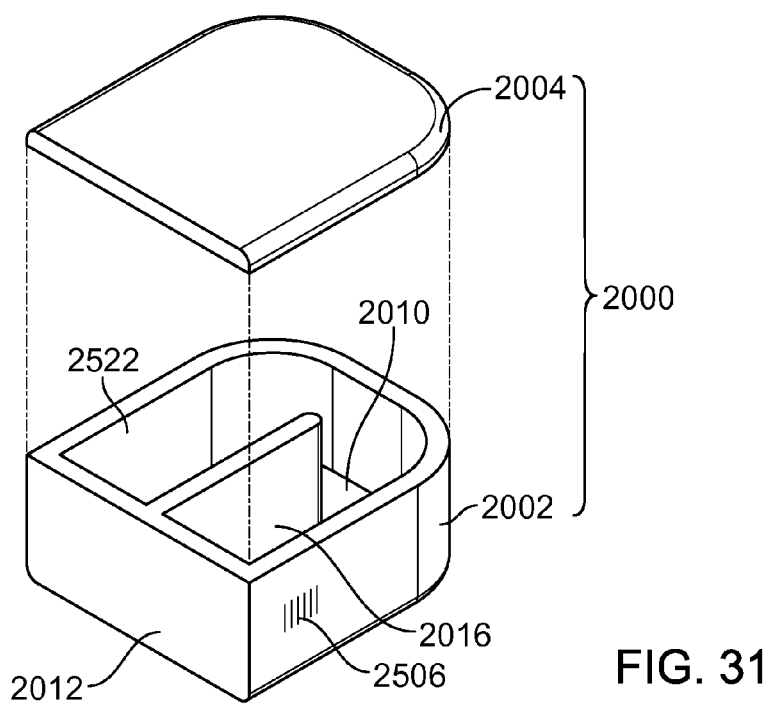

FIG. 31 is an exploded perspective view of a reference fluid cartridge that can be used with the NMR sensor assembly of FIG. 3.

Figure 1:
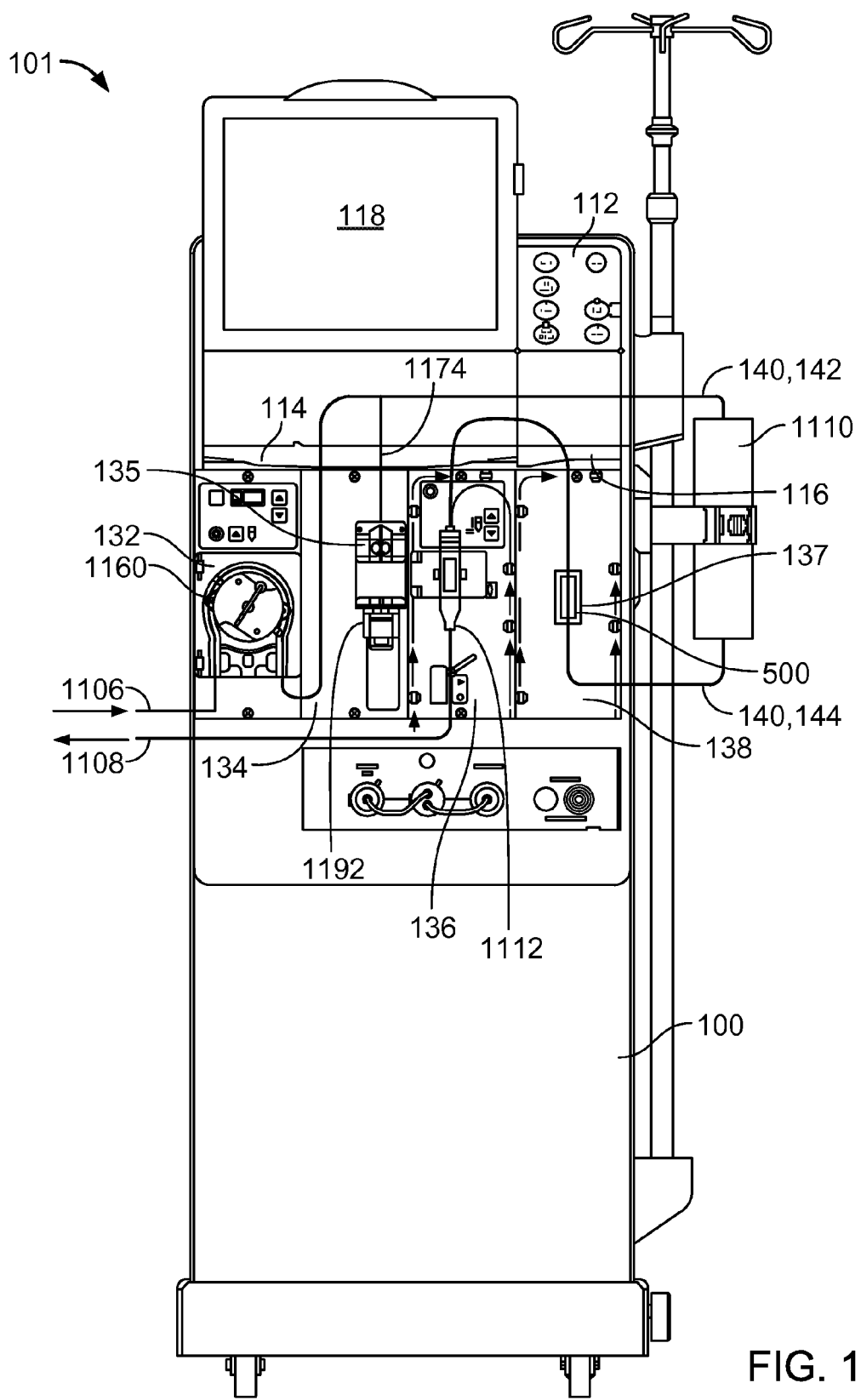
FIG. 1 is a front view of a hemodialysis machine including a nuclear magnetic resonance (NMR) module mounted in a mid-section of the machine.
Figure 32:
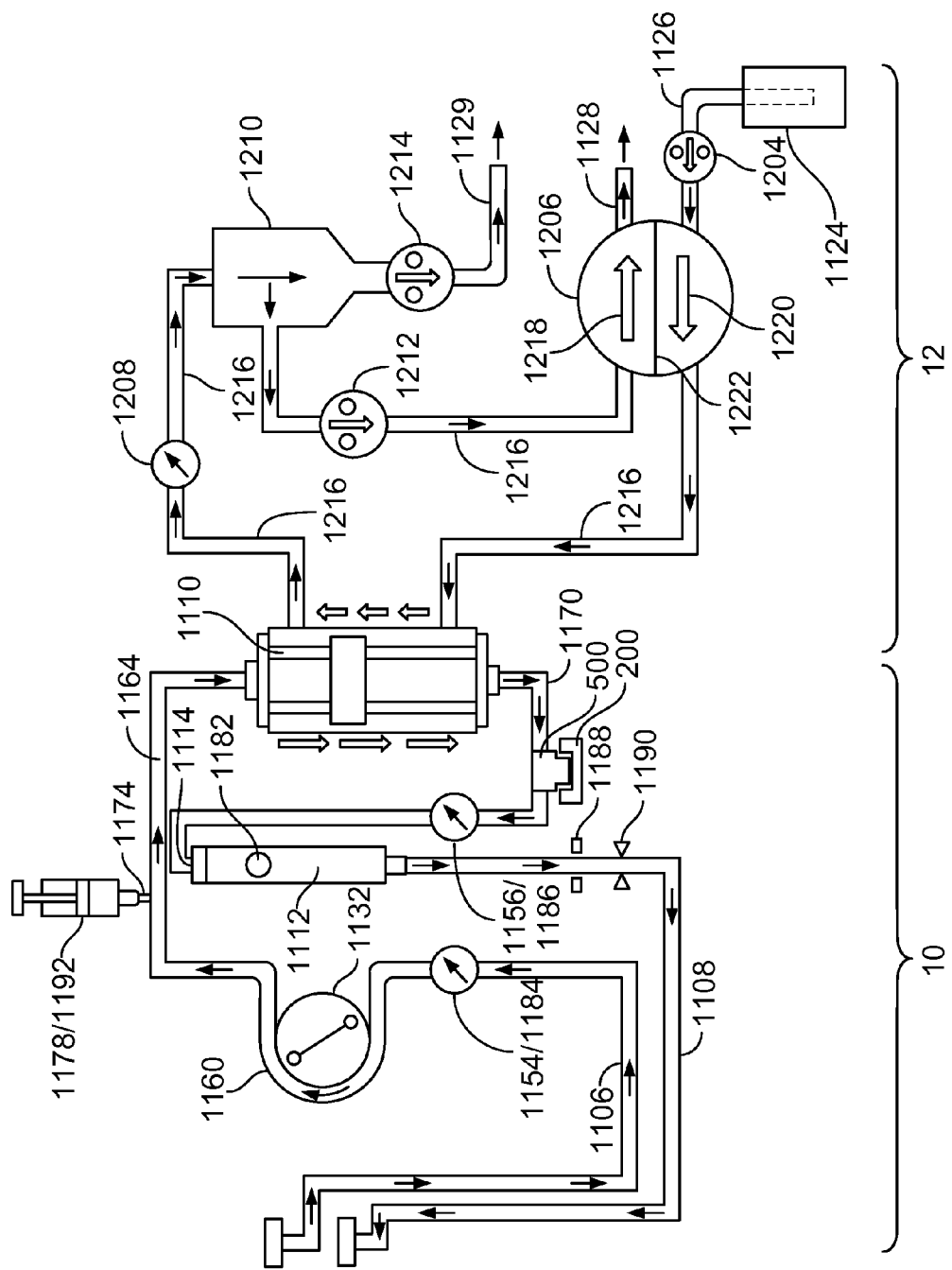

FIG. 32 is a schematic illustration of the blood and dialysate circuits of the hemodialysis system of FIG. 1, showing, among other things, the blood cartridge of FIG. 22 disposed in the NMR sensor assembly of FIG. 3 along the blood circuit.

Figure 33:
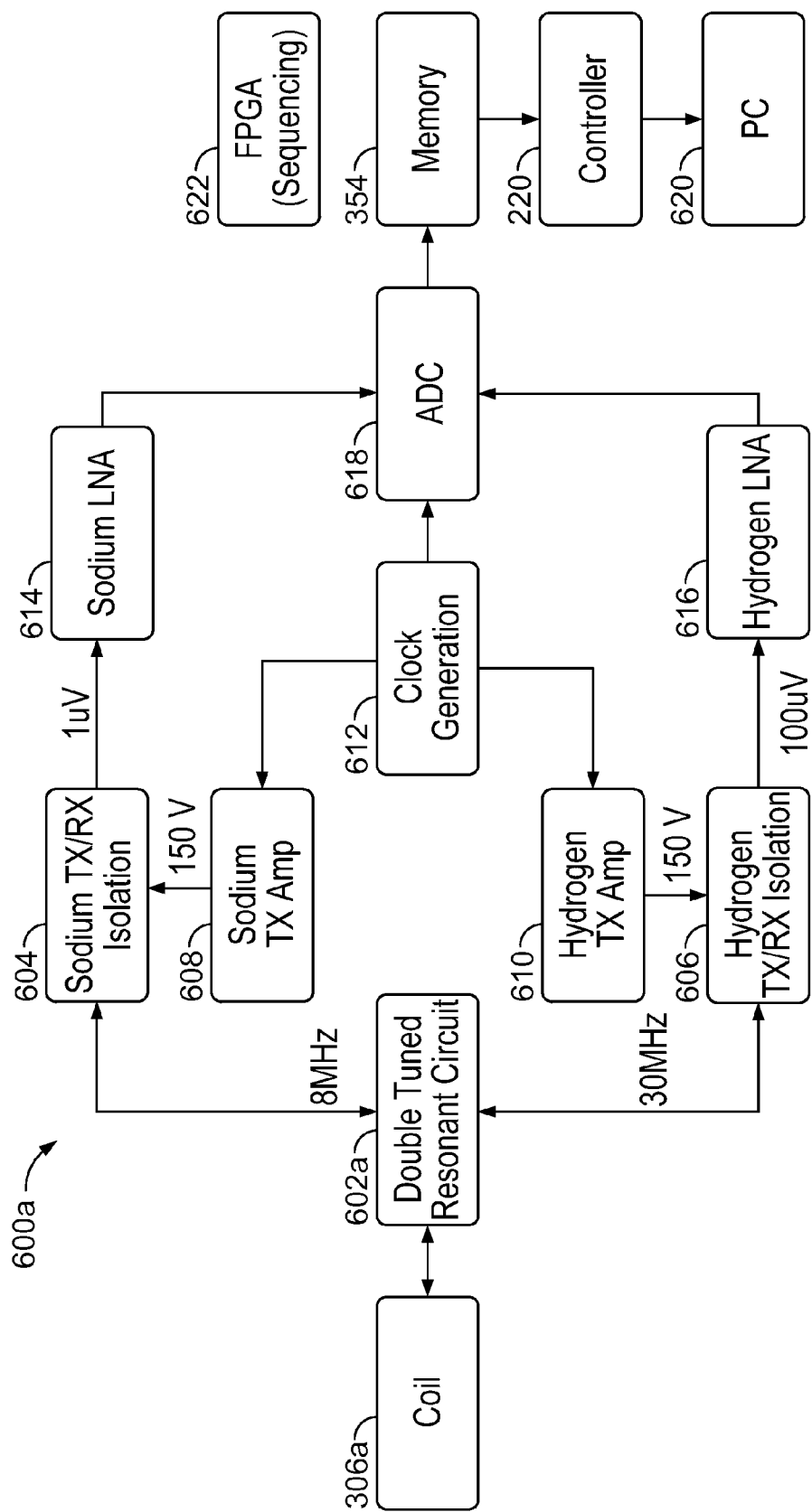

FIG. 33 shows a block diagram of a circuit used to operate an NMR sensor assembly that includes a dual tuned RF coil.

FIG. 34 shows a circuit implementing a portion of the functionality of the circuit shown in FIG. 33.

FIG. 35 shows a graph of the frequency response as measured at a first point of the circuit shown in FIG. 34.

FIG. 36 shows a graph of the frequency response as measured at a second point of the circuit shown in FIG. 34.

FIG. 37 shows a graph of the frequency response as measured at a third point of the circuit shown in FIG. 34.

Figure 38:
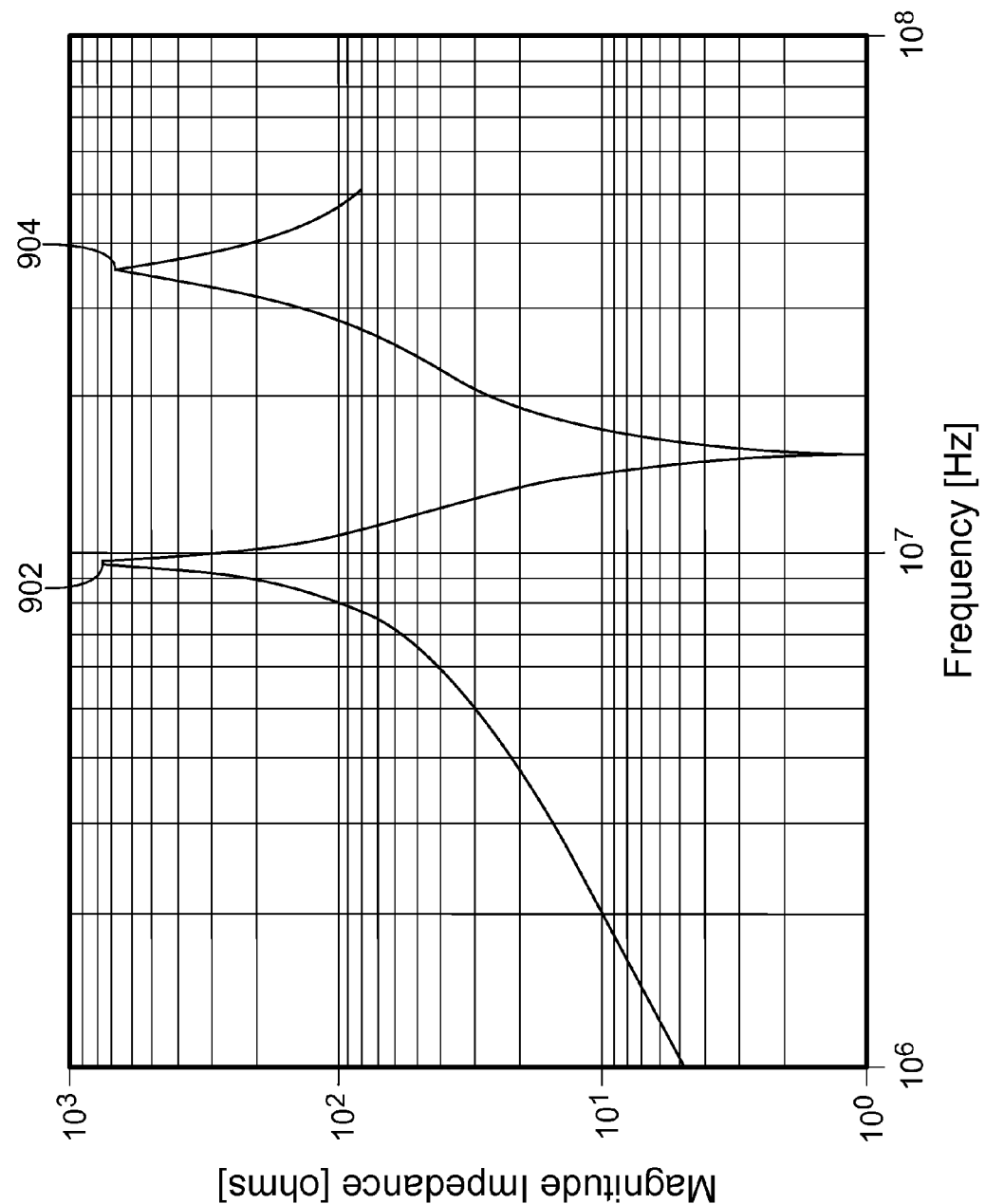

FIG. 38 shows a graph of the frequency response of the dual tuned RF coil of FIG. 33.

Figure 39:
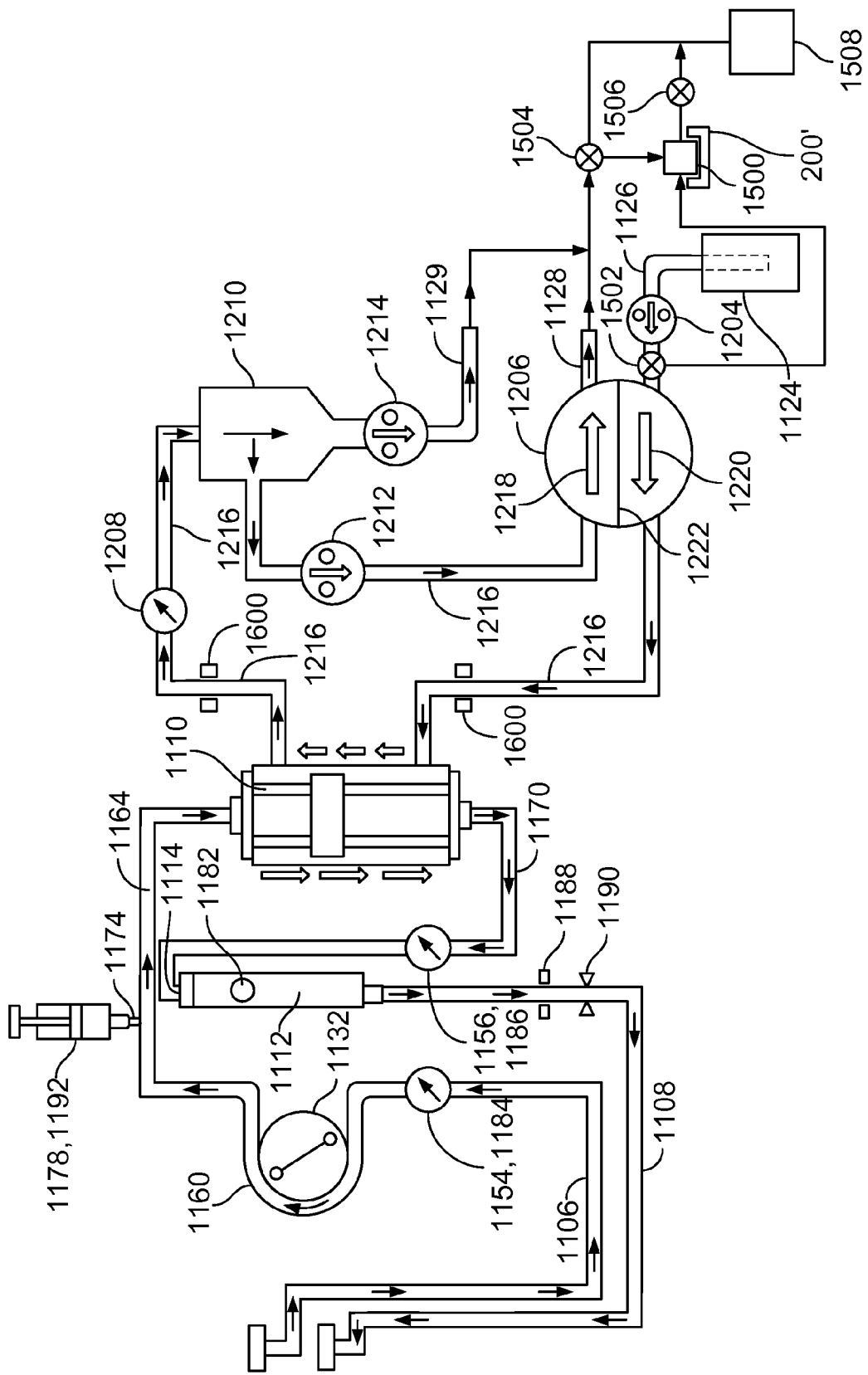

FIG. 39 is a schematic illustration of the blood and dialysate circuits of another hemodialysis system, including a dialysate cartridge disposed in an NMR sensor assembly positioned along the dialysate circuit.

Figure 40:
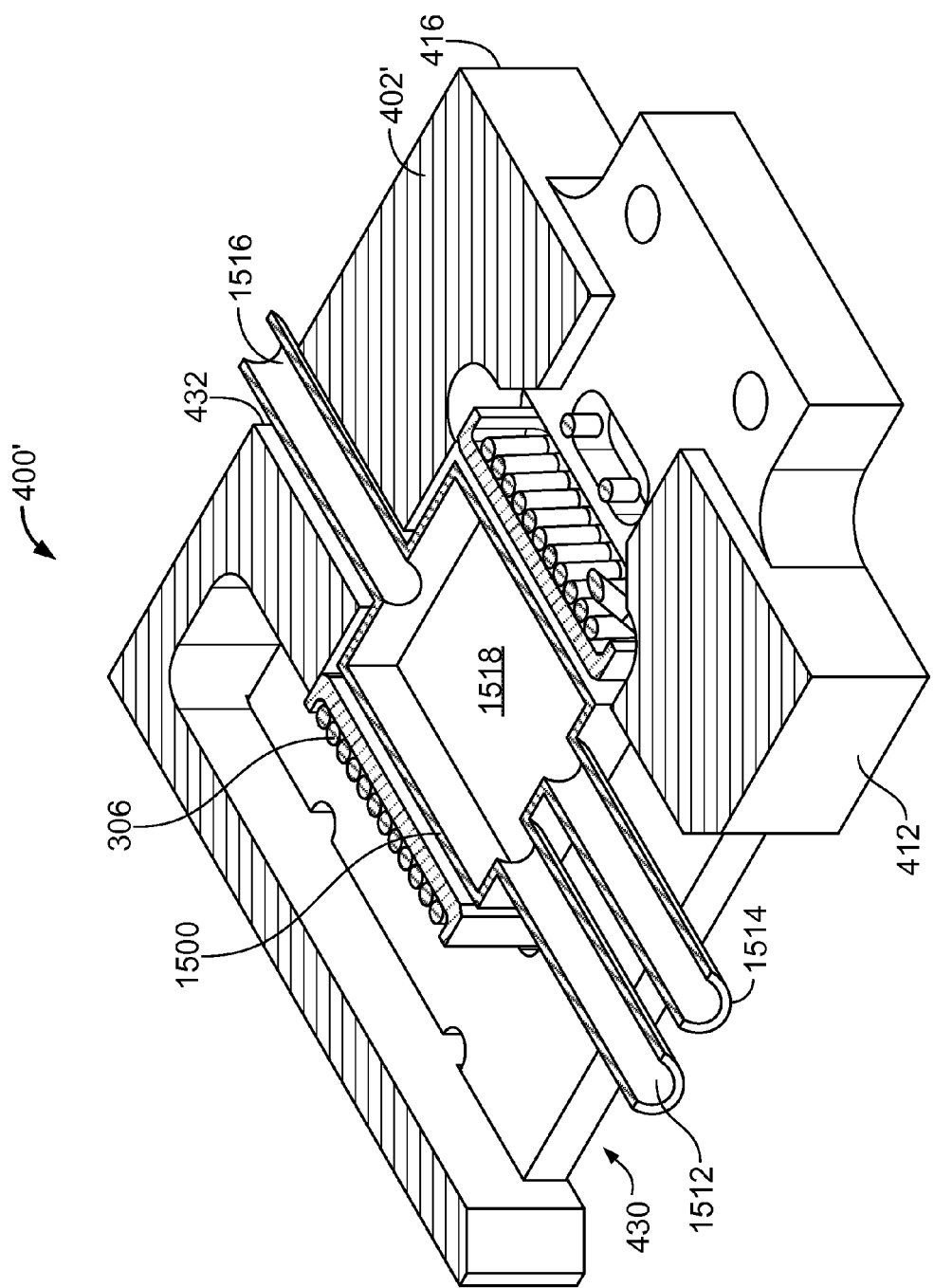

FIG. 40 is a perspective cross-sectional view of the dialysate cartridge of FIG. 39 disposed in a spacer assembly and RF coil of the NMR sensor assembly of FIG. 39.

Figure 41:
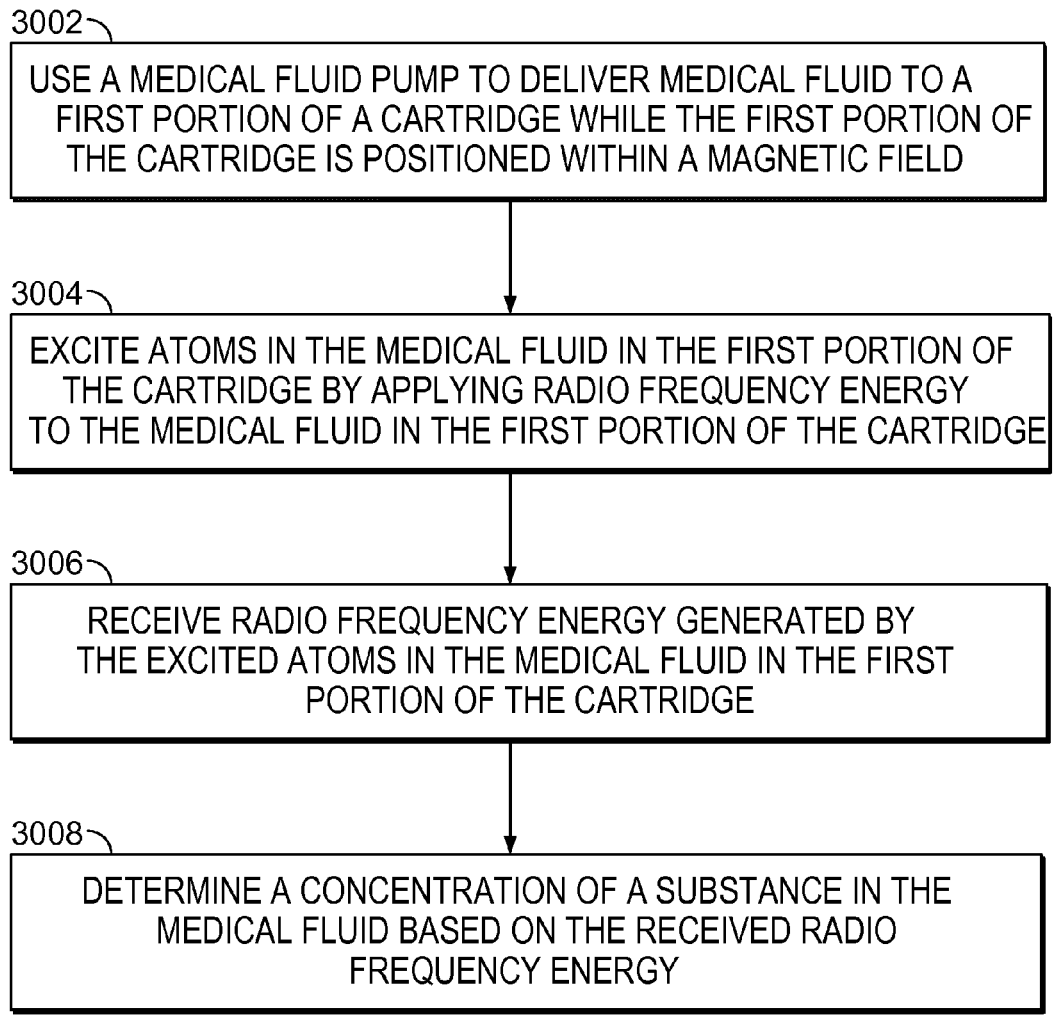

FIG. 41 is a flow chart illustrating a method of determining a concentration of a substance in a medical fluid.

Figure 42:
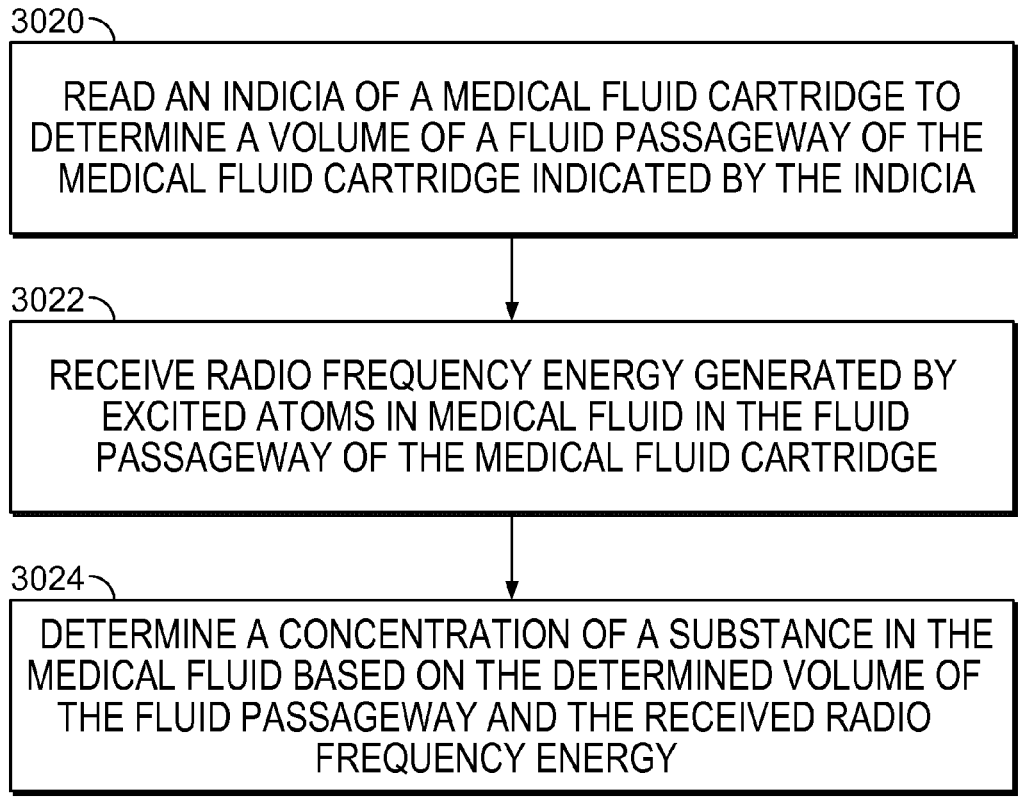

FIG. 42 is a flow chart illustrating another method of determining a concentration of a substance in a medical fluid.

Figure 43:
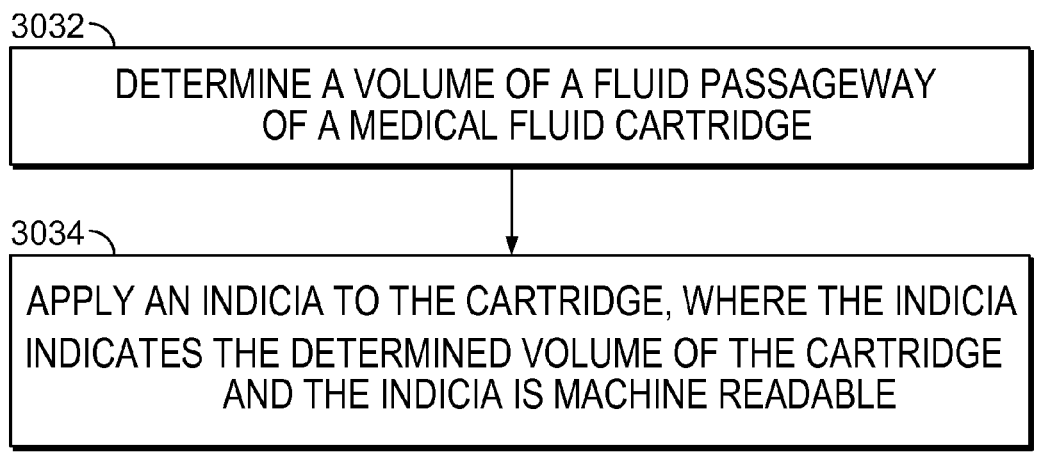

FIG. 43 is a flow chart illustrating an additional method of determining a concentration of a substance in a medical fluid.

Figure 44:
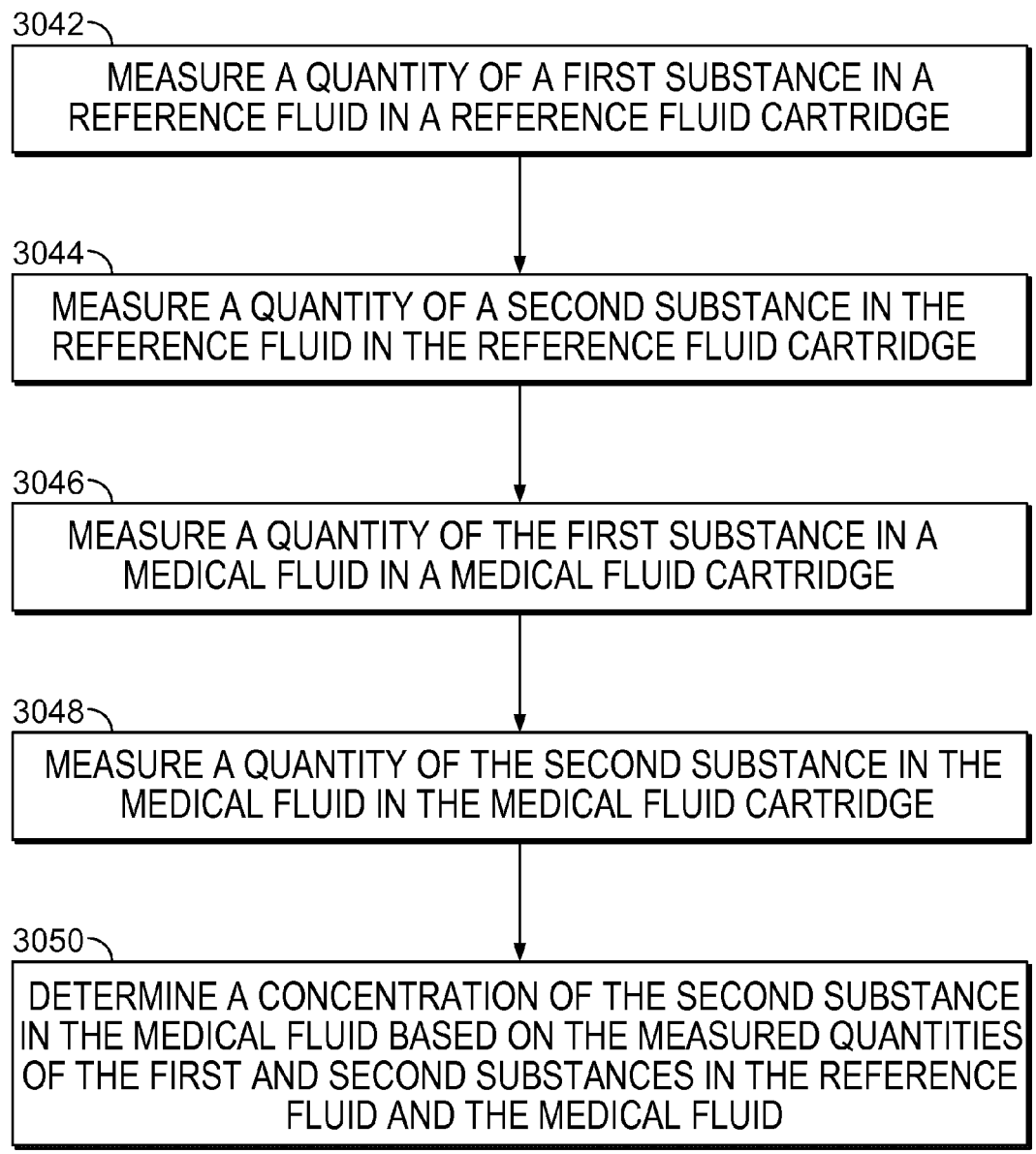

FIG. 44 is a flow chart illustrating a method of marking a medical fluid cartridge with machine readable indicia.

DETAILED DESCRIPTION

In general, this disclosure relates to sensor assemblies (e.g., nuclear magnetic resonance (NMR) sensor assemblies) that can be used to detect the concentration of a substance (e.g., sodium and/or hydrogen) in a medical fluid (e.g., blood and/or dialysate). Examples of such sensor assemblies and related systems and methods are described herein.

Referring to FIG. 1, a hemodialysis system 101 includes a hemodialysis machine 100 having an NMR module 138 that can be used to determine the concentration of sodium in blood of a patient during hemodialysis treatment. The system 101 can be used to match the concentration of sodium in dialysate used to perform the hemodialysis treatment to that of the patient's blood and/or to adjust the concentration of sodium in the blood if the sodium concentration detected by the NMR module 138 falls outside a desired range. The NMR module 138, methods of using the NMR module 138 to detect the concentration of sodium in blood, and various other components of the dialysis system 101 will be described in detail below.

Still referring to FIG. 1, the hemodialysis machine 100 includes a display 118 (which may include a touch screen) and a control panel 112, whereby operator selections and instructions can be input to and stored by a control unit of the hemodialysis machine 100. The hemodialysis machine 100 also includes modules that house components used to perform hemodialysis, including a blood pump module 132, a heparin pump module 134, an air release device and level detector module 136, and the NMR module 138.

In use, a disposable blood line set 140, which forms a blood circuit of the system 101, is connected to the modules 132, 134, 136, 138 on the front side of the hemodialysis machine 100. During treatment, patient lines 1106, 1108 of the blood line set 140 are connected to the patient and a pump tubing 1160 of the blood line set 140 is connected to the blood pump 1132. As the blood pump 1132 is operated, blood is drawn from the patient, pumped through the dialyzer 1110, and then returned to the patient.

Figure 2:
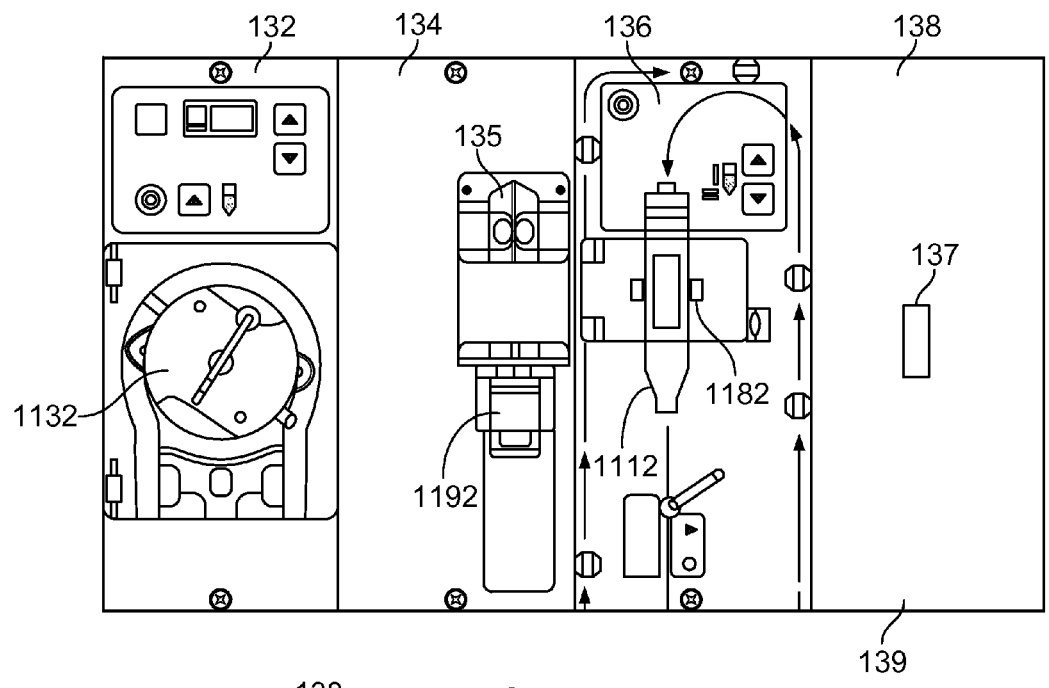
FIG. 2 is an enlarged view of the midsection of the hemodialysis machine of FIG. 1.

Referring also to FIG. 2, which illustrates the mid section of the hemodialysis machine 100 without the blood line set 140 connected to the modules 132, 134, 136, 138, the first portion 142 of the blood line set 140 includes pump tubing 1160 that is connected to the blood pump module 132 in a manner so as to operatively engage a peristaltic blood pump 1132 of the blood pump module 132. Operation of the blood pump 1132 pumps blood through the blood line set 140.

A drug delivery line 1174 of the blood line set 140 intersects the first portion 142 at a location between the blood pump 1132 and the dialyzer 1110, and is connected a syringe 1178. The syringe 1178 is connected to a syringe pump 1192 of the heparin pump module 134. The heparin pump module 134 also includes a bracket 135 to hold the syringe 1178 in the syringe pump 1192. With the syringe 1178 held in the bracket 135 in this manner, the syringe pump 1192 can be operated to move a plunger of the syringe 1178 and thus eject liquid from the syringe 1178 through the drug delivery line 1174. The heparin pump module 134 can thus be used to inject heparin from the syringe 1178 into the blood circuit via the drug delivery line 1174 during a hemodialysis treatment.

The second portion 144 of the blood line set 140 includes a blood cartridge 500 (shown in FIGS. 1 and 3) connected in series with blood lines of the blood line set 140. The blood cartridge 500 is disposed in an NMR sensor assembly 200 (shown in FIG. 3) of the NMR module 138. The blood cartridge 500 can be inserted into the NMR assembly 200 via an opening 137 formed in a cover plate 139 of the NMR module 138. The cover plate 139 can help to prevent the NMR sensor assembly 200 disposed within the housing of the NMR module 138 from becoming damaged during use. As discussed in detail below, the NMR sensor assembly 200 can be used to determine the concentration of sodium in a sample of blood flowing through the blood cartridge 500 during dialysis treatment.

The second portion 144 of the blood line set 140 also includes an air release device (or drip chamber) 1112 at a location downstream from cassette 500. The air release device 1112 permits gas, such as air, in the blood to escape before the filtered blood is returned to the patient. The air release device 1112 can be secured to level detector module 136 so as to align with a level detector 1182 that is adapted to detect the level of blood within the air release device 1112.

Figure 4:
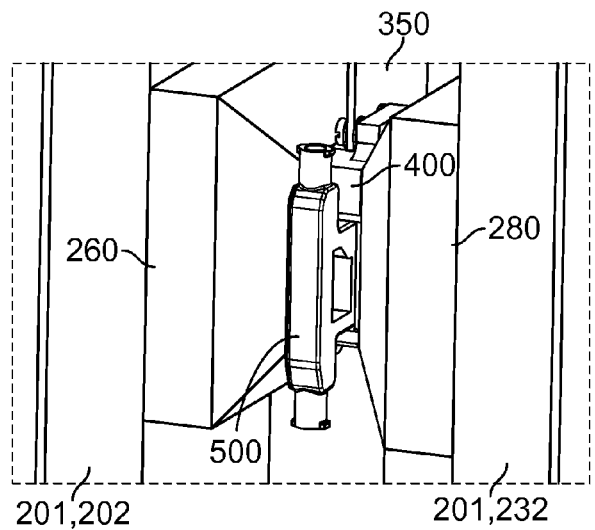
FIG. 4 is an enlarged view of the region 4 in FIG. 3, illustrating a blood cartridge disposed in the NMR sensor assembly.

Referring to FIGS. 3 and 4, the NMR module 138 includes a module housing 150 that is configured to be received within a module compartment of the hemodialysis machine 100. The NMR sensor assembly 200 is mounted within the housing 150. In some implementations, the module housing 150 includes a Faraday cage that is disposed between the housing 150 and the NMR sensor assembly 200.

The NMR sensor assembly 200 includes a pair of magnet units 260, 280 supported by a support frame 201 within the housing 150, a spacer assembly 400 that is disposed between the magnet units 260, 280, and a radio frequency (RF) energy transmitting/receiving coil assembly 300 that is supported by the spacer assembly 400 so as to be located within a magnetic field B0 between the magnet units 260, 280. As shown in FIG. 4, during use, the cartridge 500 of the blood line set 140 is inserted into the NMR module 138 in a manner such that a fluid passageway within the cartridge 500 (i.e., fluid passageway 524 shown in FIG. 27) is disposed in the magnetic field B0 and within the coil assembly 300. The coil assembly 300 transmits RF energy to, and receives RF energy from, blood flowing within the fluid passageway to determine a concentration of a substance of interest (e.g., sodium) in the blood.

Figure 5:
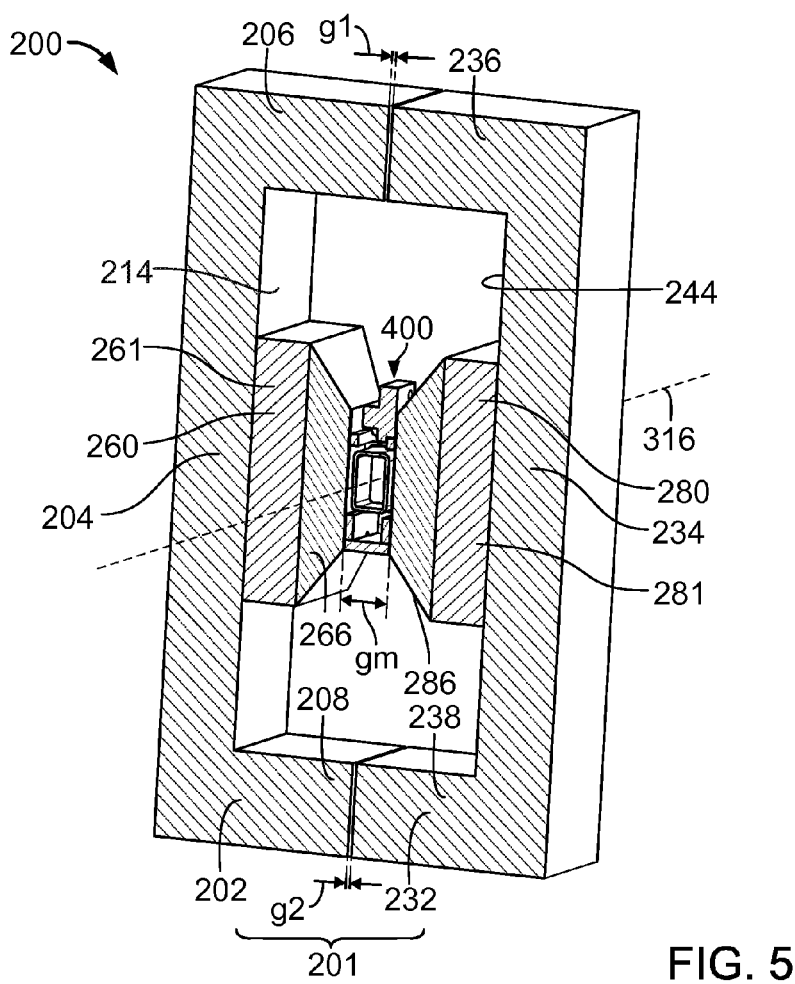
FIG. 5 is a perspective view of a support frame and magnet units of the NMR sensor assembly of FIG. 3.

Referring to FIGS. 5 and 6, the support frame 201 is configured to support the first magnet unit 260 and the second magnet unit 280 within the NMR sensor assembly 200, and is formed by two separate pieces that include a first frame member 202 and a second frame member 232.

The first frame member 202 has a U-shape that includes a first frame base 204, a first frame arm 206 that extends from one end of the first frame base 204 in a direction perpendicular to the first frame base 204, and a second frame arm 208 that extends from the opposed end of the first frame base 204 in a direction perpendicular to the first frame base 204. The first magnet unit 260 is supported by the first frame member 202. In particular, a first pole end 262 of the first magnet 261 is secured to the first frame base 204 at a location midway between the first frame arm 206 and the second frame arm 208. The first magnet unit 260 is disposed on an inside portion 214 of the U-shaped first frame member 202.

The second frame member 232 has a U-shape that includes a second frame base 234, a third frame arm 236 extending from one end of the second frame base 234 in a direction perpendicular to the second frame base 234, and a fourth frame arm 238 extending from the opposed end of the second frame base 234 in a direction perpendicular to the second frame base 234. The second magnet unit 280 is supported by the second frame member 232. In particular, a pole end 282 of the second magnet 281 is secured to the second frame base 234 at a location midway between the third frame arm 236 and the fourth frame arm 238. The second magnet unit 280 is disposed on an inside portion 244 of the U-shaped second frame member 232.

The first frame member 202 and the second frame member 232 are formed of steel (or one or more other ferromagnetic materials), and the first and second magnet units 260, 280 are secured to the support frame 201 via magnetic attraction.

The first magnet unit 260 includes a first rectangular magnet 261 having a first end 262 that is connected to the first frame member 202, and a second end 264 opposed to the first end 262. The first end 262 and second end 264 of the first magnet 261 correspond to the poles of the first magnet 261. The first magnet unit 260 also includes a soft magnetic pole piece 266 disposed on the first magnet second end 264. Similarly, the second magnet unit 280 includes a second rectangular magnet 281 having a first end 282 that is connected to the second frame member 232, and a second end 284 opposed to the first end 282. The first end 282 and second end 284 of the second magnet 281 correspond to the poles of the second magnet 281. The second magnet unit 280 also includes a soft magnetic pole piece 286 disposed on the second magnet second end 284.

The first magnet 261 and the second magnet 281 are permanent magnets. In some implementations, the first magnet 261 and the second magnet 281 are NdFeB magnets (e.g., formed of an alloy of Neodymium, Iron and Boron). Typically, the magnets 261, 281 are each 70 mm×70 mm×15 mm and magnetized to about 1.2 Tesla.

The pole pieces 266, 286 are typically formed of a material having high magnetic permeability, such as soft iron, and serve to direct the magnetic field generated by the magnets 261, 281. The pole pieces 266, 286 have a truncated pyramid shape. Thus, the first pole piece 266 has a first face 268 corresponding to a major base of the truncated pyramid and an opposed, second face 270 corresponding to the minor base of the truncated pyramid. The first face 268 of the first pole piece 266 has the same shape and dimension as, and is aligned with a periphery of, the second end 264 of the first magnet 261. Likewise, the second pole piece 286 has a first face 288 corresponding to a major base of the truncated pyramid and an opposed, second face 290 corresponding to the minor base of the truncated pyramid. The first face 288 of the second pole piece 286 has the same shape and dimension as, and is aligned with a periphery of, the second end 284 of the magnet second magnet 281. The first pole piece 266 and the second pole piece 286 are secured to the respective magnet second ends 264, 284 via magnetic attraction.

Figure 7:
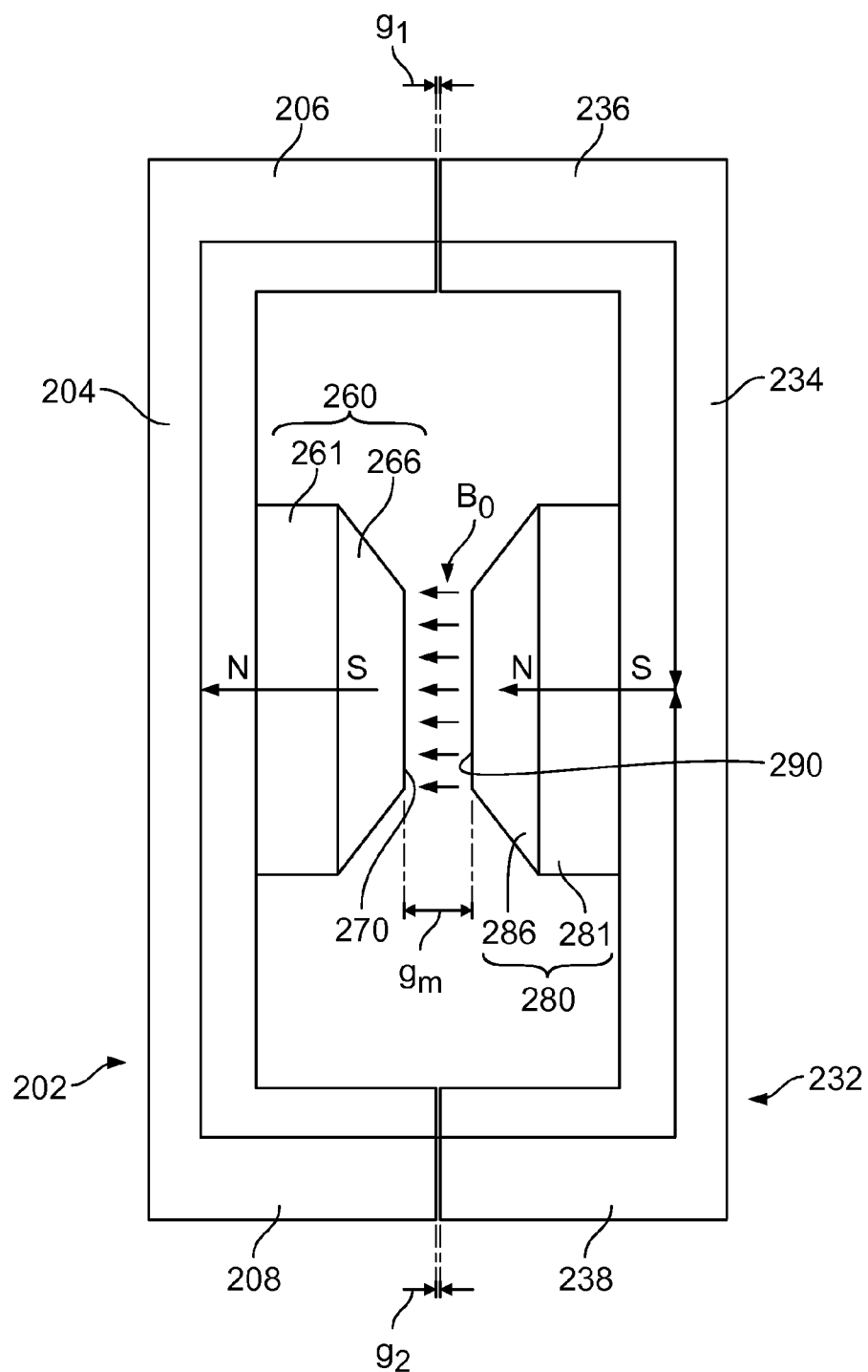
FIG. 7 is a front view of the support frame and the magnet units of the NMR sensor assembly of FIG. 3 (with the spacer assembly omitted), illustrating a magnetic loop formed therein.

Referring to FIGS. 5-7, the first frame member 202 and the second frame member 232 cooperate to provide a structure that substantially surrounds the magnet units 260, 280. More specifically, the magnet units 260, 280 are surrounded except for small secondary air gaps $g_1$, $g_2$ between ends of the frame members 202, 232, as discussed below. The first magnet unit 260 and the second magnet unit 280 are arranged and supported by the support frame 201 in a manner such that a main air gap $g_m$ exists between the first magnet unit 260 and the second magnet unit 280. In addition, the first frame member 202 is arranged relative to the second frame member 232 in a manner such that a free end 210 of the first frame arm 206 faces a free end 240 of the third frame arm 236 and is spaced apart from the third frame arm 236 so that the secondary air gap g1 exists between the first frame arm 206 and the third frame arm 236. Similarly, a free end 212 of the second frame arm 208 faces a free end 242 of the fourth frame arm 238 and is spaced apart from the fourth frame arm 238 so that the other secondary air gap g2 exists between the second frame arm 208 and the fourth frame arm 238. The frame members 202, 232 are maintained in the spaced apart relationship by the spacer assembly 400 (shown in FIGS. 5 and 6, omitted in FIG. 7 for simplicity).

In some examples, the main air gap $g_m$ is significantly larger than the secondary air gaps $g_1$, $g_2$. In particular, the main air gap $g_m$ is dimensioned to correspond to a width of the spacer assembly 400. The secondary air gaps $g_1$ and $g_2$ are substantially equal in length, and are typically in a range of about 0.5 mm to 1.0 mm. The presence of the secondary air gaps $g_1$, $g_2$ ensures that the spacer assembly 400, rather than the support frame 201, controls the orientation of the first magnet unit 260 relative to the second magnet unit 280. For example, the presence of the secondary air gaps $g_1$, $g_2$ reduces the number of mechanical tolerances that must be accounted for when manufacturing and assembling the support frame 201 and its accompanying components.

Still referring to FIG. 7, the first magnet unit 260 and the second magnet unit 280 are arranged and supported by the support frame 201 in a manner such that an attractive uniform magnetic field B0 having flux lines extending normal to the faces 270, 290 of the pole pieces 266, 286 is formed between the respective magnet units 260, 280. In some implementations, the magnetic field B0 has a magnetic field strength in a range of about 0.8 to 1.2 Tesla. It is advantageous for the magnetic field homogeneity to be less than +/−0.1 percent, which can be achieved at least in part by ensuring that the width of the main air gap $g_m$ between the pole pieces 266, 286 varies by less than +/−0.1 percent. In some implementations, the width of the main air gap $g_m$ is 12.5 mm+/−12.5 μm.

A magnetic loop (indicated by the arrows in FIG. 7) is formed that passes through the second magnet unit 280, then passes across the main air gap gm and through the first magnet unit 260 to the first support member 202, where it divides and passes through both secondary air gaps g1 and g2 into the second support member 232, and then returns to the second magnet unit 280. Although a flux direction is illustrated by the use of arrows in FIG. 7, the magnetic loop may also be illustrated using arrows oriented in a direction opposed to the arrows shown in FIG. 7.

Referring briefly again to FIGS. 5 and 6, to maintain the desired spacing between the first magnet unit 260 and the second magnet unit 280 in the presence of the attractive magnetic field B0, and also to ensure that the free pole end 264 of the first magnet 261 is oriented parallel to the free pole end 284 of the second magnet 281, the spacer assembly 400 is positioned between the first magnet unit 260 and the second magnet unit 280.

Referring to FIGS. 8-15, the spacer assembly 400 includes a generally rectangular spacer body 402, a first support plate 460 supported on a first side 404 of the spacer body 402, and a second support plate 480 supported on a second side 406 of the spacer body 402. The spacer body 402, the first support plate 460 and the second support plate 480 cooperate to define an internal space 420 within the spacer body 402. The RF coil assembly 300 is supported by the first and second support plates 460, 480 so as to enclose a portion of the internal space 420. The spacer assembly 400 also includes a pair of electrically conductive, non-magnetic shield plates 490, 496. Each of these components of the spacer assembly 400 is described in detail below.

Referring to FIGS. 8-13, the second side 406 of the spacer body 402 is opposed to the first side 404. The spacer body 402 is precisely formed (e.g., using a precision machining process) so that the first side 404 and the second side 406 are substantially parallel to one another. In some implementations, for example, they are angled by no more than 0.2 degrees (e.g., 0.1 to 0.2 degrees, 0.14 degrees) relative to one another. The spacer body 402 includes a first edge 412, a second edge 414 adjoining the first edge 412, a third edge 416 adjoining the second edge 414 and located on an opposed side of the spacer body 402 relative to the first edge 412, and a fourth edge 418 that adjoins the first and third edges 412, 416 and is located on an opposed side of the spacer body 402 relative to the second edge 414. The first, second, third and fourth edges 412, 414, 416, 418 have a dimension corresponding to the thickness of the spacer body 402 (e.g., the distance between the spacer first side 404 and the spacer second side 406).

The first side 404 of the spacer body 402 includes a first side groove 408 having a shape that generally corresponds to the shape of the first support plate 460 and a depth that corresponds to the thickness of the first support plate. Similarly, the second side 406 of the spacer body 402 includes a second side groove 410 having a shape that generally corresponds to the shape of the second support plate 480 and a depth that corresponds to the thickness of the second support plate 480. Both the first side groove 408 and the second side groove 410 open at the spacer body fourth edge 418.

The spacer body 402 includes an opening 430 in the first edge 414 that communicates with the first side groove 408 and the second side groove 410 to form the internal space 420 within the spacer body 402. The opening 430 is dimensioned to permit a portion of the blood cartridge 500 (shown in FIG. 4) to be inserted into the internal space 420. The edges 430a of the opening 430 are beveled to facilitate insertion of the cartridge 500.

The spacer body 402 includes a flange 422 that protrudes outward from the body second edge 414 in a direction normal to the body second edge 414. The flange 422 includes through holes 424 that are dimensioned to receive fasteners (e.g., bolts), whereby a printed circuit board 350 (shown in FIG. 3) including RF coil driving electronics can be secured to the spacer body 402 via the flange 422 in a location that is near the RF coil assembly 300.

The spacer body 402 is formed of a ceramic material. In some implementations, the spacer body 402 is formed of a machinable glass ceramic, for example, Macor® manufactured by Corning, Inc. of Corning, N.Y. Forming the spacer body 402 of a ceramic material is advantageous since ceramics are well suited for the highly-precise machining required to provide a structure having opposed sides that are parallel to the required extent. In addition, ceramic materials are non-magnetic and non-electrically conductive. These properties are beneficial for the spacer body 402 when assembled in the gap between the magnet units 260, 280, since these properties reduce undesirable acoustic effects associated with placement of metal structures in the gap.

FIGS. 9-11, 14 and 15 show the first support plate 460 and the second support plate 480 mounted to the spacer body 402. The first and second support plates 460, 480 are substantially similar in form and function, so only the first support plate 460 will be described here. The first support plate 460 is formed of a sodium-free plastic, such as Acetal, Delrin, polycarbonate, acrylic, or another sodium-free plastic with high dimensional stability. The first support plate 460 is configured to be press fit within the corresponding groove 408 formed in the spacer body 402 such that outward facing surfaces of the first support plate 460 lie flush with the outer surface of the spacer body 402. More specifically, the first support plate 460 lies flush with the first side 404 and the fourth edge 414 of the spacer body 402. The first support plate 460 includes a through opening 468 that is shaped and dimensioned to receive and support portions of the RF coil assembly 300. For example, the through opening 468 is generally rectangular in shape and includes inwardly protruding tab portions 469 formed on a pair of opposed edges of the through opening 468. The tab portions 469 are dimensioned to abut flanges 312 formed on a tubular form 304 (shown in FIGS. 16 and 17) of the RF coil assembly 300, as discussed further below.

Referring to FIG. 6, the spacer assembly 400 also includes a pair of electrically conductive, non-magnetic shield plates 490, 496, which are typically formed of copper. The shield plates are rectangular in shape to conform to the shapes of the spacer body 402 and the free ends of the magnet units 260, 280 (e.g., the pole face second sides 270, 290), but are not limited to this shape. The shield plates 490, 496 are thin (e.g., the height or thickness is less than the length and width), while the thickness of the shield plates is equal to or greater than the minimum skin depth for the working frequency of the RF coil 306. In some implementations, the skin depth is about 25 μm, and the shield plates 490, 496 have a thickness in a range of 50 μm to 100 μm.

Figure 8:
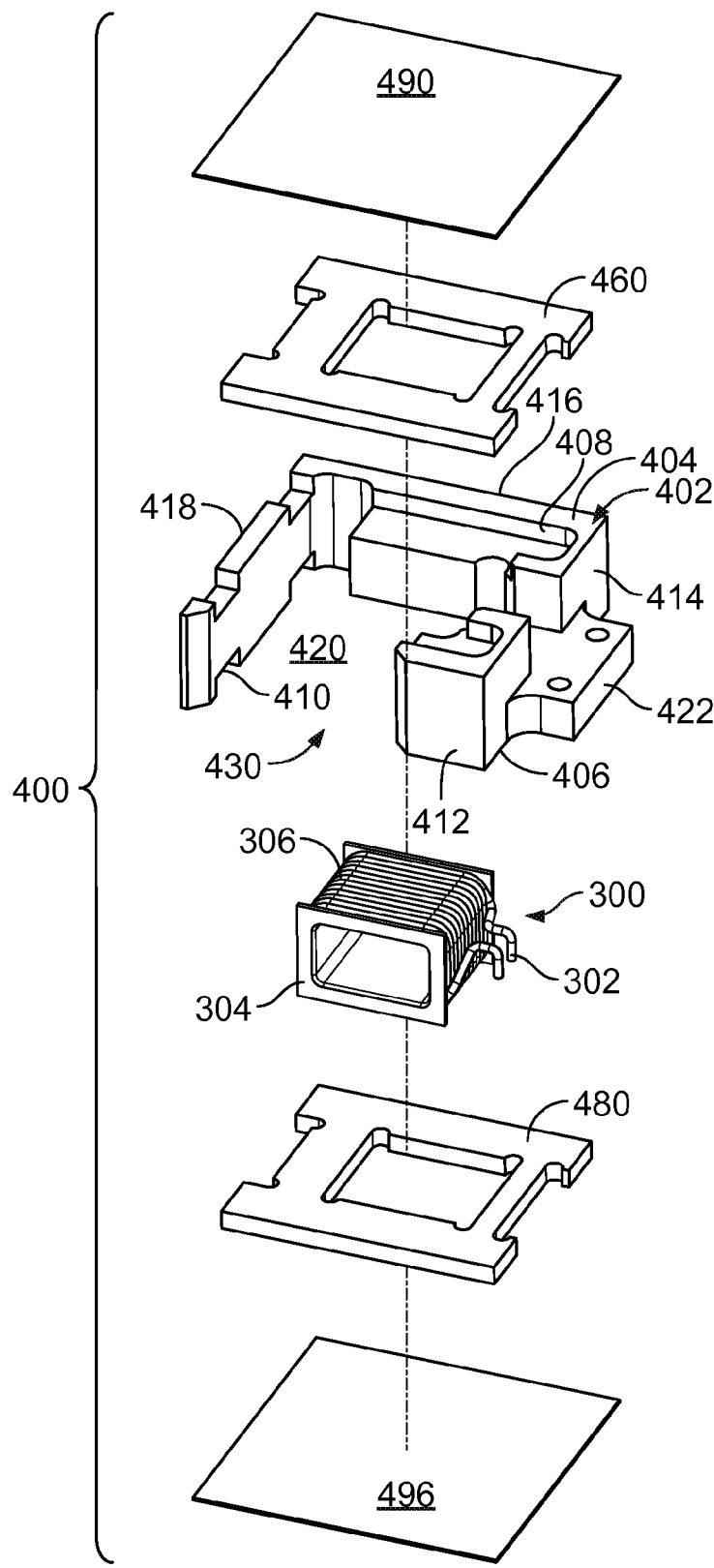
FIG. 8 is an exploded perspective view of the spacer assembly of the NMR sensor assembly of FIG. 3 in combination with a radio frequency (RF) coil assembly of the NMR sensor assembly of FIG. 3.

Referring to FIGS. 6 and 8, when the spacer assembly 400 is assembled, one of the shield plates 490 is disposed between the spacer body first side 404 and the first pole piece second end 270, and another of the shield plates 496 is disposed between the spacer body second side 406 and the second pole piece second end 290. The shield plates 490, 496 are typically not mechanically secured to the spacer assembly 400. Rather, they are clamped between the magnet units 260, 280 in the desired arrangement due to the attractive magnetic force between the magnets 261, 281. In this configuration, the shield plates 490, 496 serve to shield the pole pieces 266, 286 from the RF field generated by the RF coil assembly 300. As a result, acoustic ringing in the pole pieces 266, 286 can be reduced or eliminated. Including the shield plates 490, 496 in the spacer assembly 400 can also improve the Q factor (e.g., coil sensitivity) of the RF coil 306 relative to an assembly without the shield plates 490, 496.

To provide a magnetic field B0 between the first magnet unit 260 and the second magnet unit 280 that is sufficiently homogeneous for measurement of the concentration of a substance disposed in the magnetic field B0, the second face 270 of the first pole piece 266 is oriented substantially parallel to the second face 290 of the second pole piece 286. For example, the faces 270, 290 can be angled by no more than 0.2 degrees (e.g., 0.1 to 0.2 degrees, 0.14 degrees) relative to one another. In use, the spacer assembly 400, including the spacer body 402 having parallel opposed first and second sides 404, 406, is placed between the first magnet unit 260 and the second magnet unit 280. The spacer assembly 400 is retained between the first magnet unit 260 and the second magnet unit 280 via the mechanical force caused by the strong magnetic attraction between the two assemblies 260, 280 (e.g., the spacer assembly 400 is clamped between the first magnet unit 260 and the second magnet unit 280).

In the NMR sensor assembly 200, the support frame 201, the magnet units 260, 280 and the spacer assembly 400 cooperate to provide a balanced magnet design, as illustrated in FIG. 5. A moderate imbalance between the magnetic forces in the two secondary air gaps $g_1$, $g_2$ between the first frame member 202 and the second frame member 232 can be tolerated. For example, the assembly will only pivot about the left edge of the spacer assembly 400 if the following equation is satisfied:

$$F_l\left(\frac{d-w}{2}\right) > F_r\left(\frac{d+w}{2}\right), \text{ i.e. if } F_l > F_r\left(\frac{d+w}{d-w}\right)$$

In this equation, $F_l$ is the magnetic force across one of the air gaps g (e.g., the upper air gap $g_1$), $F_r$ is the is the magnetic force across the other one of the air gaps g (e.g., the lower air gap $g_2$), d is a distance from a coil axis 316 (shown in FIG. 16-18) to the main air gap $g_m$, and w is a width of the spacer assembly 400.

In addition to increased mechanical stability as compared to some other NMR magnet assembly designs, such as certain C-core magnet assembly designs, the balanced magnet design has additional benefits. It can provide a slightly stronger B0 field and less stray field than some other NMR magnet assembly designs such as certain C-core magnet assembly designs. Conversely, it is relatively insensitive to nearby magnets and ferromagnetic parts. For example, bringing another large magnet as close as 50 mm to the support frame 201 may only alter the magnetic field B0 by 0.001T in certain implementations.

As shown in FIGS. 13 and 15, the spacer body 402 is equipped with a barcode reader 498. The barcode reader 498 can be used to automatically read a barcode on the blood cartridge 500 when the blood cartridge 500 is inserted into the NMR sensor assembly 200. The barcode reader 48 is connected to the controller 220 of the NMR sensor assembly 200 such that information read by the barcode reader 498 can be transmitted to the controller 220.

Referring to FIGS. 16-18, the RF coil assembly 300 includes the tubular form 304 having a generally rectangular cross section, and a conductive wire 302 wrapped around the form 304 to form a radio frequency (RF) coil 306 having a coil axis 316. As used herein, the term "RF coil" refers to a coil configured to emit and/or detect radio frequency electromagnetic energy. When the RF coil is configured to emit and/or detect electromagnetic energy at a particular frequency, the RF coil can be said to be tuned to that particular frequency. In some implementations, the conductive wire 302 is an enamel-insulated solid copper wire having a gauge of 0.5 mm that is wound 10 turns about the form 304.

Each of the opposed ends 308, 310 of the form 304 are provided with a flange 312, which has a rectangular profile. When the RF coil assembly 300 is assembled with the first support plate 460 and the second support plate 480, the RF coil assembly 300 is disposed within the through openings 468, 488 of the plates 460, 480 so that the flanges 312 of the coil wire form 304 abut the tab portions 469 of the through opening 468 (shown in FIG. 14) and tab portions 489 of the through opening 488 (shown in FIG. 15) in a press fit relationship. In addition, when the RF coil assembly 300 is assembled with the first and second support plates 460, 480, and the first and second support plates 460, 480 are disposed within the respective grooves 408, 410 of the spacer body 402, the coil 306 surrounds a portion of the spacer body internal space 420 and the coil axis 316 is oriented transverse to an axis aligned with the magnetic field B0. Respective ends 302a, 302b of the conductive wire 302 are electrically connected to the printed circuit board 350 (shown in FIG. 3) mounted on the spacer body flange 422. The printed circuit board 350 includes an NMR sensor assembly control unit 220 and an electronic circuit 600 used to operate the NMR sensor assembly 200, as discussed further below.

A mathematical representation of electromagnetic energy in the radio frequency range is sometimes called an electromagnetic signal (or simply a signal). The RF coil 306 is used in an electronic circuit 600 (shown in FIG. 19) that detects signals caused by the transmission of electromagnetic energy, such as the signals emitted by sodium atoms when the atoms are exposed to electromagnetic energy. The detected signal carries information about how many sodium atoms are in the blood flowing through the cartridge 500. Sodium atoms precess at a frequency of 11.262 MHz/Tesla. In some implementations, a magnetic field of 0.8 Tesla is used. In that magnetic field, sodium atoms precess at a frequency of about 9.0 MHz.

The electronic circuit 600 that includes the RF coil 306 is configured to switch between a transmitter mode and a receiver mode. For example, transistors can be used to switch between voltage sources or sinks that are connected to the circuit. In this way, the same RF coil 306 can both transmit a signal and receive a signal emitted by the sodium atoms caused to precess by the transmitted signal. The transmitted signal is usually generated using a high voltage (e.g., 100 volts) so that the transmitted signal carries enough energy to incite the sodium atoms to precess. In contrast, the signal emitted by the sodium atoms is typically very weak, by which we mean that the signal represents a very small amount of energy. For example, if a signal is transmitted using a voltage of 100 volts, then the received signal may induce a voltage of only several microvolts.

A weak signal is susceptible to noise, which is a by-product of electrical energy flowing through other components of the circuit (e.g., the transistors of the circuit) that includes the RF coil 306. The presence of noise in the signal reduces the ability of an NMR system to use the information carried by the signal to accurately measure the amount of sodium atoms in the blood sample of a patient.

To reduce noise, the circuit 600 includes a low noise amplifier (LNA) 614, which is an electronic component that increases the energy of a signal while minimizing the amount of noise introduced as part of the amplification. In this way, the LNA 614 outputs a signal that is stronger, carries little additional noise, and is less susceptible to noise introduced by other components of the electronic circuit. However, because the LNA 614 cannot withstand high voltages, the LNA 614 is connected to the transistors used to switch between the transmitter mode and the receiver mode of the circuit in a way that isolates the LNA 614 from the high voltages of the transmitter mode. Thus, the complete circuit 600 that incorporates the RF coil 306, the LNA 614, and transistors introduces noise into signals detected by the RF coil 306, because the transistors have electromagnetic characteristics, such as impedance, that affect electromagnetic signals carried by the circuit. Further, the combination of the RF coil 306 together with resonant components, such as a capacitor, has a high impedance so that the coil has high sensitivity at its resonant frequencies. For this reason, the combination of the RF coil 306 and a capacitor is sometimes called a high impedance RF coil or a resonant RF coil. In the circuit 600 including the high impedance RF coil 306 (e.g., an RF coil with an impedance of 10K ohms or more), the ratio of the impedance of the RF coil 306 to the impedance of some of the other components (such as the transistors of switching circuits) will be relatively high at resonant frequencies of the high impedance RF coil 306. Because the LNA 614 is connected in parallel with the high impedance RF coil 306, the impedance of the LNA 614 will be higher still. For example, the ratio of the impedance of the LNA 614 to the high impedance RF coil 306 may be 10:1 (e.g., if the impedance of the RF coil 306 is 10K ohms and the impedance of the LNA 614 is 100K ohms). Thus, relatively little current will flow across the LNA 314 compared to the current that flows across the high impedance RF coil 306, and so relatively little energy will be lost at the LNA 314 when the circuit 300 carries a signal (such as a signal detected by the RF coil 306).

FIG. 19 shows a block diagram of the circuit 600 used in the NMR sensor assembly 200. The circuit 600 includes an RF coil 306 that can be used, in some examples, to both excite sodium atoms and to detect energy emitted by excited sodium atoms. The RF coil 306 is connected to a resonant circuit 602. A resonant circuit is a circuit that includes capacitors and/or inductors and is arranged to oscillate at a particular frequency. In this way, a signal carried across a resonant circuit at the frequency of the resonant circuit is carried across the circuit with a minimal loss of energy. In this example, the components of the resonant circuit 602 are configured to resonate at a resonant frequency of the RF coil 306 (e.g., at the precession frequency of sodium atoms).

The resonant circuit 602 connects to an isolation circuit 604. The circuit 600 cannot both transmit and receive at the same time, so the isolation circuit 604 includes one or more switches that isolate the transmitting portions of the circuit 600 from the receiving portions of the circuit 600.

When the isolation circuit 604 is switched to a transmitting mode, a transmitting amplifier 608 is activated, which amplifies a signal for the sodium frequency (e.g., a signal at a frequency of 11.262 MHz/Tesla of magnetic field). The signal causes the RF coil 306 to generate an electromagnetic field that excites sodium atoms. A clock generation circuit 612 generates signals that pass through the amplifier 608.

When the isolation circuit 604 is switched to a receiving mode, a signal received by the RF coil 306 passes through the resonant circuit 602 to the low-noise amplifier 614, which amplifies a signal for the sodium frequency. The analog output of the low-noise amplifier 614 is provided to an analog-digital converter 618 (ADC), which converts the analog output to one or more digital signals. The digital signals are provided to, and analyzed by, digital components to determine information about the sodium in a patient's blood. The digital components include a microcontroller 610, memory 616, and a computer system 620. In this example, the computer system 620 represents the dialysis machine 100. In some implementations, the digital components also include a field-programmable gate array 622 (FPGA). For example, the FPGA 622 can be used to synchronize the transmitting and receiving modes for each of the two frequencies and implement the timing for the NMR pulse sequence.

The RF coil 306 has a high impedance (e.g., 10K ohms or more, 50K ohms or more). When the isolation circuit 604 is switched to a transmitting mode (e.g., when the RF coil 306 transmits a signal to excite sodium atoms), the receiving components are isolated from the high voltages of the transmitting mode. When the isolation circuit 604 is switched to a receiving mode (e.g., when the coil is waiting to detect electromagnetic fields generated by the precession of the excited atoms), the transmitting components are isolated from the low voltage receiving components. When combined with the RF coil 306, this arrangement allows low voltage electronic components to be placed on the circuit 600 without the risk of damage.

Some transmitter/receiver circuits use a matching circuit to connect a high impedance coil to a low impedance (e.g., 50 ohms) load. However, in the circuit 600, the switching components (e.g., the isolation circuit 604) are directly connected to the RF coil 306 and no impedance matching circuit is used. If the RF coil 306 were operated at a low impedance, the coil would lose sensitivity due to energy lost from the impedance of the components of the isolation circuit 604. The loss of energy would increase the amount of time needed to receive enough energy to analyze the signal in the receiving mode.

Since the RF coil 306 has a high impedance, the RF coil 306 can be connected to a high-impedance low-noise amplifier (e.g., low-noise amplifier 614). A high-impedance low-noise amplifier is used so that a matching circuit is not required to connect the low-noise amplifier 614 and the RF coil 306.

FIG. 20 shows a circuit 700 implementing a portion of the functionality of the circuit 600 shown in FIG. 19. For example, the components of the circuit 700 (depending on their configuration) can be used as the portion of the circuit 600 used to detect sodium atoms. The RF coil 306 of FIG. 19 is shown as a current source 702, an inductor 706, and a resistor 708, which represent the current generated by the coil, the inductance of the coil, and the resistance of the coil, and the inductance of the coil, respectively. The combination of the current source 702, the inductor 706, and the resistor 708 is connected in parallel with a capacitor 704. In some examples, the capacitance of the capacitor 704 can be 650 picofarads, the inductance of the inductor 706 can be 1 microhenry, and the resistance of the resistor 708 can be 0.3 ohms. The RF coil 306 has a high impedance when the capacitor 704 is used.

The circuit 700 switches between a transmitting mode and a receiving mode using transistors 710, 712. The first transistor 710 has a first voltage source 714 connected to a gate input of the first transistor 710, and the second transistor 712 has a second voltage source 716 connected to a gate input of the second transistor 712. The first transistor 710 has a source input connected to ground, and the second transistor 712 has a source input connected to a third voltage source 718.

When the first transistor 710 is switched off and the second transistor 712 is switched on, the circuit 700 is in a receiving mode (FIG. 20). The first voltage source 714 applies 0 volts to the gate input of the first transistor 710 to switch it off, and the second voltage source 716 applies 80 volts to the gate input of the second transistor 712 to switch it on. The third voltage source 718 is set to 100 volts, such that the source input of the second transistor 712 is a path to AC ground across a capacitor 720. This capacitor 720 is a variable capacitor that can be used to adjust the receiving frequency. In some examples, the capacitor 720 has a capacitance of 315 picofarads. Current also flows through another capacitor 722. This capacitor 722 is a variable capacitor that can be used to adjust the transmitting frequency. In some examples, the capacitor 722 has a capacitance of 185 picofarads. Current also flows through a resistor 724 and a capacitor 726 arranged in parallel, which are representations of the input resistance and capacitance of a low noise amplifier. In some examples, the resistor 724 has a resistance of 500K ohms, and the capacitor 726 has a capacitance of 2 picofarads.

When the first transistor 710 is switched on and the second transistor 712 is switched off, the circuit 700 is in a transmitting mode (FIG. 21). The first voltage source 714 connected to the gate of the first transistor 710 applies a voltage of 20 volts. The first transistor 710 provides a path to ground across a capacitor 728. In some examples, the capacitor 728 has a capacitance of 1 microfarad. The second and third voltage sources 716, 718 connected to the second transistor 712 apply a voltage of negative 100 volts across the gate and source inputs of the second transistor 712, respectively. In this way, a high voltage is applied to the circuit 700 when it is operating in the transmitting mode.

The transistors 710, 712 each have a low on-state resistance to avoid the loss of energy in the circuit. The transistors 710, 712 operate at a high voltage to withstand the high voltages used (e.g., the voltages provided by the second and third voltage sources 716, 718). For example, the transistors 710, 712 maintain a switching state (e.g., the on or off state that the transistors are designed to maintain under normal operating conditions) when a voltage of at least 100 volts is applied to any of the inputs (e.g., source, gate, or drain).

In the arrangement represented by the circuit 700, there are no large inductive elements (e.g., coils with ferrites), so the receiver electronics can be mounted close to the dual tuned coil 306 within the magnetic field without affecting the operation of the circuit 700.

In the NMR sensor assembly 200, the RF coil assembly 300 is disposed in the gap $g_m$ between the first magnet unit 260 and the second magnet unit 280 so that the coil axis 316 is transverse to the magnetic field B0.

Referring briefly again to FIG. 4, when the blood cartridge 500 is disposed in the spacer assembly 400 of the NMR sensor assembly 200, a fluid passageway of the cartridge 500 resides within the RF coil 306. The axis 316 of the coil 306 is perpendicular to the magnetic field B0. During use, blood flows through the fluid passageway of the blood cartridge 500 and sodium atoms in the blood within the fluid passageway become aligned with the magnetic field B0. Once the sodium atoms have become aligned with the magnetic field B0, RF energy is transmitted by the RF coil 306 to excite the sodium atoms in the blood causing the affected atoms to align with the transmission field (i.e., along the coil axis 316) rather than the main field B0. Since the coil axis 316 is transverse to the magnetic field B0, the RF energy transmitted by the RF coil 306 temporarily changes alignment of atoms to a direction transverse to the main field B0.

NMR technology exploits the fact that the nuclei of some atoms—such as hydrogen (1H) and sodium (23Na) atoms—have a magnetic moment due to their spin. Although the behavior of such a nucleus is governed by quantum mechanics, it can be understood in classical terms as small, spinning magnet having the following properties:

1) In the presence of a static magnetic field, its spin axis aligns with the field (e.g., the static magnetic field B0 that is generated in the gap gm of the NMR sensor assembly 200);
2) If its axis is tilted away from the magnetic field B0 (e.g., by transmitting an RF pulse from the RF coil 306), the axis precesses at a frequency proportional to the strength of the magnetic field B0; and
3) The precessing nucleus generates a rotating magnetic field that induces an AC voltage in the nearby RF coil 306.

The precession frequency is determined not only by the strength of B0 but also by the type of atom, quantified by its gyromagnetic constant. This is the basis for distinguishing different types of atoms in a sample. For example, in a 1 Tesla field, 1H nuclei precess at a frequency of 42.0 MHz, while 23Na nuclei precess at a frequency of 11.6 MHz. The RF coil 306 is tuned so as to permit transmission and reception of signals at the frequency of sodium. The strength of RF energy received by the RF coil 306 is proportional to the number of sodium atoms in the blood sample analyzed. Provided the sample volume is fixed, the RF signal is similarly proportional to the sodium concentration in the blood sample.

The blood cartridge 500 is designed to hold a blood sample within the spacer assembly 400 in such a way that the blood flowing through the cartridge 500 resides within the magnetic field B0 for a desired length of time, and then is directed through the RF coil 306 where a sodium measurement is performed on the blood.

As shown in FIGS. 22-30, the cartridge 500 includes a rigid base 502, and a rigid cover 504 that is attached to one side of the base 502 in a fluid-tight manner. In some implementations, the cover 504 is welded to the base 502. However, other attachment techniques can alternatively or additionally be used.

The base 502 includes a flat plate 510 having an irregular peripheral shape, and an outer sidewall 512 that extends in a direction normal to the plate 510 along the periphery of the plate 510 so as to surround the plate 510. The base 502 includes a through opening 514 formed at a location spaced apart from the outer sidewall 512. The base 502 also includes an inner sidewall 516 that extends in a direction normal to the plate 502 along the periphery of the through opening 514 so as to surround the through opening 514. When the cover 504 is connected to the base 502, the cover 504, the plate 510, the outer sidewall 512 and the inner sidewall 516 cooperate to form fluid passageways 522, 524, 526 through the cartridge 500, as discussed further below. The outer sidewall 512 includes a first opening 530 corresponding to a fluid inlet of the cartridge 500, and a second opening 532 corresponding to a fluid outlet of the cartridge 500. Fluid line connectors 534 are provided on an outer surface of the outer sidewall 512 at locations corresponding to the fluid inlet 530 and fluid outlet 532. The fluid line connectors 534 permit connection of blood lines of the blood line set 140 to the cartridge 500.

Referring to FIG. 27, when seen in plan view, the plate 510 generally has a T-shape including a horizontal portion 510a that extends generally linearly between the fluid inlet 530 and the fluid outlet 532, and a vertical portion 510b that intersects a mid-region of the horizontal portion 510a. As used herein, the terms vertical and horizontal refer to the orientation illustrated in FIG. 27, and are not intended to be limiting.

When seen in plan view, the outer sidewall 512 has an irregular shape corresponding to the shape of the base 502. In particular, the outer sidewall 512 includes a first portion 540 having a U-shape including a first side 540a, a second side 540b, and a closed end 540c joining the first side 540a and the second side 540b. The outer sidewall 512 includes a second portion 550 having a U-shape including a first side 550a, a second side 550b, and a closed end 550c joining the first side 550a and the second side 550b. The second side 550b of the second portion 550 is parallel and adjacent to the first side 540a of the first portion 540, and is connected to the first side 540a of the first portion 540 by a connecting portion 545. As a result, a gap 536 is formed between the first portion 540 and the second portion 550. The first portion 540 is shorter than the second portion 550. That is, the first portion closed end 540c is closer to the through opening 514 than the second portion closed end 550c. The first portion 540 is wider than the second portion 550. In other words, the first portion sides 540a, 540b are further apart than the second portion sides 550a, 550b. The first portion 540, the second portion 550 and the gap 536 correspond to the vertical portion 510b of the T-shaped plate 510. The outer sidewall 512 also includes a generally linear third portion 560. The third portion 560 extends in a direction transverse to the respective first and second sides 540a, 550a, 540b, 550b of the first and second portions 540, 550. The third portion 560 corresponds to the horizontal portion 510a of the T-shaped plate.

Like the outer sidewall 512, when seen in plan view, the inner sidewall 516 also has an irregular shape. The inner sidewall 516 is surrounded by and spaced apart from the outer sidewall 512. In particular, the inner sidewall 516 includes a directing portion 580 having a U shape including a first side 580a, a second side 580b, and a closed end 580c joining the first side 580a and the second side 580b. The directing portion first side 580a extends into the outer sidewall second portion 550 so as to form the alignment meandering passageway 522 within the second portion 550. The directing portion second side 580b extends into the outer sidewall first portion 550 so as to form the perturbation meandering passageway 524 within the first portion 540. The directing portion closed end 580c is generally parallel to and spaced apart from the outer sidewall connecting portion 545. The direction portion closed end 580c and the outer sidewall connecting portion 545 cooperate to permit fluid communication between the alignment meandering passageway 522 and the perturbation meandering passageway 524.

Still referring to FIG. 27, the inner sidewall 516 also includes a base portion 570 that extends parallel to the outer sidewall third portion 560. The space between the inner sidewall base portion 570 and the outer sidewall third portion 560 defines a bypass fluid passageway 526 that directs fluid in a generally linear path between the cartridge inlet 530 and the cartridge outlet 532. The base portion 570 is longer than a width of the vertical portion 510b. One end of the base portion 570 cooperates with the outer sidewall 512 to define a meander inlet 522a to the alignment meandering passageway 522 that is in fluid communication with, and oriented in parallel to, the bypass passageway 526 at a location adjacent to the cartridge inlet 530. An opposed end of the base portion 570 cooperates with the outer sidewall 512 to define a meander outlet 524a from the perturbation meandering passageway 524 that is in fluid communication with, and oriented in parallel to, the bypass passageway 526 at a location adjacent to the cartridge outlet 532.

The cartridge 500 is connected to the blood line set 140 (shown in FIG. 1), which forms the blood circuit 10 of the hemodialysis system 101. As a result, blood flowing through the blood line set 140 passes through the cartridge 500. Still referring to FIG. 27, a portion (e.g., 15 to 25 percent, 20 percent) of the blood that enters the cartridge inlet 530 is diverted into the inlet 522a of the alignment meandering passageway 522, while the remainder of the blood is directed through the bypass passageway 526, and exits the cartridge 500 via the outlet 532. To this end, the cross sectional area A1 of the meander inlet 522a is smaller than the cross sectional area A2 of the bypass passageway 526. For example, the cross sectional area A1 of the meander inlet 522a can be in a range of 15 to 25 percent (e.g., 20 percent) of the cross sectional area A2 of the bypass passageway 526. In some implementations, the cross sectional area A2 of the bypass passageway 526 is at least 5 times greater (e.g., 5-15 times greater) than the cross sectional area A1 of the meander inlet 522a.

Referring to FIGS. 4, 5, 27, 29 and 30, when the cartridge 500 is inserted into the spacer assembly 400, the cartridge vertical portion 510b is inserted into the spacer body opening 430 so that the cartridge vertical portion 510b resides within the spacer internal space 420, and thus within the main air gap $g_m$ of the NMR sensor assembly 200 (FIG. 5). In particular, the cartridge outer sidewall first portion 540 is disposed inside the RF coil 306 such that the first and second sides 540a, 540b of the cartridge outer sidewall first portion 540 and second side 580b of the inner sidewall first portion 580 are parallel with the coil axis 316. In addition, the cartridge outer sidewall second portion 550 is disposed outside the RF coil 306 such that the first and second sides 550a, 550b of the cartridge outer sidewall second portion 550 and the first side 580a of the inner sidewall first portion 580 are parallel with the coil axis 316, and so that a portion of the RF coil 306 resides within the gap 536 between the outer sidewall first portion 540 and the outer sidewall second portion 550.

The cartridge horizontal portion 510a remains outside the spacer body 402 and extends parallel to the spacer body first edge 412. By this arrangement, the bypass passageway 526 remains outside both the spacer body 402 and the main air gap $g_m$ of the NMR sensor assembly 200.

The alignment and perturbation meandering passageways 522, 524 are configured to slow down the rate of fluid flow therein relative to the rate of flow through the blood lines connected to the cartridge 500 and the rate of flow through the cartridge inlet 530. This is accomplished by providing the alignment meandering passageway 522 with a reduced cross sectional area relative to the cross sectional area A3 of the cartridge inlet 530 and the cross sectional area A2 of the bypass passageway 526, as shown in FIGS. 22-26, and by including multiple changes in direction of the fluid flow. The cross sectional area A4 of the alignment meandering passageway 522 is equal to the cross sectional area A1 of the meander inlet 522a, and the cross sectional area A5 of the perturbation meandering passageway 524 is greater than that of the cross sectional area A4 of the alignment meandering passageway 522 and the cross sectional area A1 of the alignment meandering passageway 522. For example, the cross sectional area A5 of the perturbation meandering passageway 524 can be in a range of 2 to 10 times greater than the cross sectional area A4 of the alignment meandering passageway 522 and the cross sectional area A1 of the alignment meandering passageway 522. As a result, the rate of fluid flow within the alignment meandering passageway 522 is less than that of the bypass passageway 526, and the rate of fluid flow within the perturbation meandering passageway 524 is less than that of the alignment meandering passageway 522. In some implementations, the blood flows through the bypass passageway 526 at a rate of 400 ml/min to 600 ml/min (e.g., 500 ml/min), the blood flows through the alignment meandering passageway 522 at a rate of 50 ml/min to 200 ml/min (e.g., 125 ml/min), and the blood flows through the perturbation meandering passageway 524 at a rate of 50 ml/min to 150 ml/min (e.g., 100 ml/min). Due to the differing lengths and flow areas of the passageways 522, 524, 526, during a hemodialysis treatment, it typically takes 150 msec to 300 msec (e.g., 200 msec) for the blood to flow through each of the alignment meandering passageway 522 and the perturbation meandering passageway 524. It typically takes significantly less time for the blood to flow through the bypass passageway 526.

Sharp corners within the fluid passageways 520 are avoided to prevent blood stagnation that can lead to coagulation. In addition, the cassette 500 may include other features that help to prevent shearing in the flow and thus help to ensure that the blood passing through the cassette 500 is not damaged. For example, the inlet geometry can be configured to avoid the formation of a jet by ensuring a smooth transition between the inlet 534 and the region immediately inside the cassette 510. Similarly, a smooth transition can be provided between region 510 and where the flow subsequently divides between the meander passageways 522a and the bypass passageway 526.

Knowing the precise volume of the blood sample to be analyzed can facilitate accurate determination of the concentration of sodium in the blood flowing through the cartridge 500. Referring to FIGS. 28-30, to this end, during or after manufacture of the cartridge 500, the volume V1 of the portion of the perturbation meandering passageway 524 that resides within the RF coil 306 is measured, and a side of the cartridge 500 is marked to include a barcode 506 to indicate its volume. Any of various techniques that are capable of precisely determining the volume V1 of the portion of the perturbation meandering passageway 524 that resides within the RF coil 306 can be used. In some implementations, a contact probe (e.g., the Equator 300 contact probe manufactured by Renishaw) can be used to measure the volume V1. A single spot laser (e.g., the M7L/50 single spot laser manufactured by MEL) can alternatively or additionally be used to measure the volume V1. As discussed above, the barcode scanner 498 of the spacer assembly 400 can automatically read the barcode 506 of the cartridge 500 when the cartridge 500 is inserted into the spacer body 402, and can transmit that information to the NMR sensor assembly controller 220.

FIG. 31 illustrates a reference fluid cartridge 2000 that can be used to hold a reference fluid sample within the spacer assembly 400 during calibration of the NMR sensor assembly 200. The reference fluid cartridge 2000 includes a rigid base 2002, and a rigid cover 2004 that connects to one side of the base 2002 in a fluid-tight manner. In some implementations, the cover 2004 is welded to the base 2002. However, other attachment techniques can alternatively or additionally be used.

The base 2002 includes a flat plate 2010 having a generally rectangular peripheral shape, and an outer sidewall 2012 that extends in a direction normal to the plate 2010 along the periphery of the plate 510 so as to surround the plate 2010. The base 2002 also includes an inner sidewall 2016 that extends in a direction normal to the plate 2010. When the cover 2004 is connected to the base 2002, the cover 2004, the plate 2010, the outer sidewall 2012 and the inner sidewall 2016 cooperate to form a fluid reservoir 2522 within the cartridge 2000, which has the same size and shape as the portion of the perturbation meandering passageway 524 of the cartridge 500 that resides within the RF coil 306. The reservoir 2522 is filled with a solution including a known concentration of sodium. Like the cartridge 500, the reference fluid cartridge 2000 is marked during or after manufacture with a barcode 2506, in this case indicating the concentration of the sodium within the reservoir 2522. When the reference fluid cartridge 2000 is inserted into the spacer body 402 of the NMR sensor assembly 200, the barcode reader 498 reads the barcode 2506, and transmits the read information to the NMR sensor assembly controller 220. A difference between the actual sodium concentration of the reference fluid indicated by the barcode 2506 and the concentration of the reference fluid determined by the NMR sensor assembly 200 can be used to calibrate the NMR sensor assembly 200 to ensure that accurate readings of blood sodium can be achieved when the NMR sensor assembly 200 is later used to measure the sodium concentration of a blood sample in the blood cartridge 500.

Referring to FIG. 32, the dialysis system 101 includes the blood circuit 10 defined by the blood line set 140 and a dialysate circuit 12. During dialysis treatment, the hemodialysis machine 100 controls and monitors the flow of dialysate and blood through the dialysate circuit 12 and the extracorporeal blood circuit 10, respectively.

Referring particularly to the right side of FIG. 32, the dialysate components of the dialysate circuit 12 that are located inside the housing of the hemodialysis machine 100 include a first dialysate pump 1204, a balancing device 1206, a pressure sensor 1208, an equalizing chamber 1210, a second dialysate pump 1212, and an ultrafiltration pump 1214. These dialysate components are fluidly connected to one another via a series of dialysate lines 1216.

The first dialysate pump 1204 is capable of pumping fresh dialysate to a chamber half 1220 of the balancing chamber 1206 via a dialysate supply line 1126 that is connected to a dialysate source 1124, and the second dialysate pump 1212 can be used to pump spent dialysate to a chamber half 1218 of the balancing chamber 1206 via a dialysate supply line 1126 that is connected to the equalizing chamber 1210. In some implementations, the dialysate pumps 1204, 1212 are peristaltic pumps. However, other types of pumps can alternatively or additionally be used. Examples of other suitable types of pumps include diaphragm pumps and gear pumps.

The balancing device 1206 includes a spherical chamber that is divided into the first chamber half 1218 and the second chamber half 1220 by a flexible membrane 1222. As fluid flows into the first chamber half 1218, fluid is forced out of the second chamber half 1220, and vice versa. This balancing device construction helps to ensure that the volume of fluid entering the balancing device 1206 is equal to the volume of fluid exiting the balancing device 1206. This helps to ensure that the volume of fresh dialysate entering the dialysate circuit is equal to the volume of spent dialysate exiting the dialysate circuit when desired during treatment, as described in greater detail below.

An ultrafiltration line 1129 is connected to an outlet of the equalizing chamber 1210. The ultrafiltration pump 1214 is operatively connected to the ultrafiltration line 1129 such that when the ultrafiltration pump 1214 is operated, spent dialysate can be pulled from the equalizing chamber 1210 and directed to the drain via the ultrafiltration line 1129. Operation of the ultrafiltration pump 1214 while simultaneously operating the dialysate pump 1212 causes increased vacuum pressure within the dialysate line 1216 connecting the equalizing chamber 1210 to the dialyzer 1110, and thus creates increased vacuum pressure within the dialyzer 1110. As a result of this increased vacuum pressure, additional fluid is pulled from the blood circuit 10 into the dialysate circuit 12 across the semi-permeable structure (e.g., semi-permeable membrane or semi-permeable microtubes) of the dialyzer 1110. In certain implementations, the ultrafiltration pump 1214 is a peristaltic pump. However, any various other types of pumps can alternatively or additionally be used. Examples of other suitable types of pumps include diaphragm pumps and gear pumps.

A pressure sensor 1208 is also positioned along the dialysate line 1216 leading from the dialyzer 1110 to the equalizing chamber 1210 for monitoring fluid pressure within the dialysate circuit 12.

FIG. 41 is a flow chart illustrating a method of determining a concentration of a substance in a medical fluid. As shown, the method includes using a medical fluid pump to deliver medical fluid to a first portion of a cartridge while the first portion of the cartridge is positioned within a magnetic field (Step 3002), exciting atoms in the medical fluid in the first portion of the cartridge by applying radio frequency energy to the medical fluid in the first portion of the cartridge (Step 3004), receiving radio frequency energy generated by the excited atoms in the medical fluid in the first portion of the cartridge (Step 3006), and determining a concentration of a substance in the medical fluid based on the received radio frequency energy (Step 3008).

FIG. 42 is a flow chart illustrating another method of determining a concentration of a substance in a medical fluid. The method includes reading an indicia of a medical fluid cartridge to determine a volume of a fluid passageway of the medical fluid cartridge indicated by the indicia (Step 3020), receiving radio frequency energy generated by excited atoms in medical fluid in the fluid passageway of the medical fluid cartridge (Step 3022), and determining a concentration of a substance in the medical fluid based on the determined volume of the fluid passageway and the received radio frequency energy (Step 3024).

FIG. 43 is a flow chart illustrating a method of measuring and marking a medical fluid cassette. The method includes determining a volume of a fluid passageway of a medical fluid cartridge (Step 3032) and applying an indicia to the cartridge where the indicia indicates the determined volume of the cartridge and the indicia is machine readable (Step 3034).

A method of performing hemodialysis, which includes measuring a concentration of a sodium in a blood sample during dialysis treatment using the NMR sensor assembly 200 and the blood cartridge 500, will now be described.

Before beginning the dialysis treatment, the NMR sensor assembly 200 is calibrated. In particular, the reference fluid cartridge 2000 including a sample liquid (e.g., a saline solution) of known sodium concentration is inserted into the NMR sensor assembly 200 so as to reside within the RF coil 306. The barcode reader 498 of the spacer body 402 is used to read the sodium concentration of the sample liquid (i.e., the actual reference sodium concentration) and the volume $V_r$ of the reference cartridge reservoir 2522 from the barcode 2506 on the side of the reference fluid cartridge 2000. The information read by the barcode reader 498 is transmitted to the controller 220 and stored in memory.

The reference fluid cartridge 2000 is allowed to sit within the RF coil 306 for a predetermined waiting period (e.g., 150 msec to 300 msec, 20 msec) before a sodium measurement is performed. The waiting period permits the sodium atoms within the reservoir 2522 to become aligned with the magnetic field B0.

After the waiting period has elapsed, the NMR sensor assembly 200 is used to measure the amount of sodium in the reference fluid contained in the reference fluid cartridge 2000 (i.e. the measured reference sodium quantity). This measurement of the amount of sodium in a known concentration permits the controller 220 to account for variations in the NMR sensor assembly 200 from use to use, which may result, for example, from slight changes in the uniformity of the magnetic field, trace amounts of sodium in the system, etc. The controller 220 uses the difference between the known sodium concentration (or quantity) of the reference fluid within the reference fluid cartridge 2000 and the measured sodium concentration (or quantity) of the reference fluid to calibrate the NMR sensor assembly 200. For example, a machine correction factor CF can be calculated as follows:

$$CF = X_{Na\ actual}/X_{Na\ measured} = C_{Na\ actual}/C_{Na\ measured}$$

where $X_{Na\ actual}$ is the actual reference sodium quantity;
$X_{Na\ measured}$ is the measured reference sodium quantity;
$C_{Na\ actual}$ is the actual reference sodium concentration; and
$C_{Na\ measured}$ is the measured/determined reference sodium concentration.

The machine correction factor CF is used by the controller 220 as a multiplication factor to account for variations in sensor output during calculations of sodium concentration. If, for example, the known actual sodium concentration of the reference fluid within the reference fluid cartridge 2000 is 125 mEq/L and the measured/determined sodium concentration of the reference fluid is 100 mEq/L, then subsequent sodium measurements made by the NMR sensor assembly 200 would be multiplied by a correction factor CF of 1.25 ((125 mEq/L)/(100 mEq/L)) to obtain accurate readings or determinations of those sodium concentrations.

After calibrating the NMR sensor assembly 200 (or the controller 220 of the NMR sensor assembly 200), the reference fluid cartridge 2000 is removed from the NMR sensor assembly 200, and the blood cartridge 500, while connected in series within the blood line 1170 of the blood line set 140 that forms the blood circuit 10 (FIG. 32), is inserted into the NMR sensor assembly 200 (FIGS. 4, 29 and 30). In particular, the perturbing meandering fluid passageway 524 is disposed inside the RF coil 306 such that the first and second sides 540a, 540b of the cartridge outer sidewall first portion 540 and second side 580b of the inner sidewall first portion 580 are parallel with the coil axis 316. The alignment meandering passageway 522 is disposed within the magnetic field B0 and outside the RF coil 306 such that the first and second sides 550a, 550b of the cartridge outer sidewall second portion 550 and the first side 580a of the inner sidewall first portion 580 are parallel with the coil axis 316. The bypass passageway 526 remains outside the spacer body 402 and extends in parallel with the spacer body first edge 412. By this arrangement, the bypass passageway 526 resides outside both the spacer body 402 and the main air gap $g_m$ of the NMR sensor assembly 200.

With the blood cartridge 500 within the NMR sensor assembly 200, the barcode reader 498 of the spacer assembly 400 is used to read the barcode 506, which indicates the volume V1 of the portion of the perturbing meandering fluid passageway 524 that is disposed inside the RF coil 306 (FIG. 28), and the volume V1 is transmitted to the controller 220. The controller 220 is programmed to use the volume V1 in combination with a measurement of the number of sodium atoms in the blood contained in the volume V1 of the cartridge 500 to determine the concentration of sodium in the blood. The controller 220 can, for example, be programmed to determine the concentration of blood samples in the cartridge 500 by dividing the measured quantity of sodium atoms $X_{Na\ measured}$ by the volume V1.

Following calibration of the NMR sensor assembly 200 and determination of the volume of the V1 of the cartridge 500, hemodialysis treatment is performed using the hemodialysis machine 100 with the blood cartridge 500 disposed within the NMR sensor assembly 200. Referring to FIG. 32, to carry out the hemodialysis treatment, the blood pump 1132 is operated to draw the patient's blood into the blood circuit 10 via the patient line 1106. Through continued operation of the blood pump 1132, the blood is delivered through a blood passage of the dialyzer 1110. At the same time, the dialysate pumps 1204, 1212 are operated to draw dialysate into the dialysate circuit 12 from the dialysate source 1124 and to cause the dialysate to flow through a dialysate passage of the dialyzer 1110. As the blood flows through the blood passage of the dialyzer 1110 and the dialysate flows through a dialysate passage of the dialyzer 1110, impurities and toxins are drawn from the blood into the dialysate across a semi-permeable structure (e.g., semi-permeable microtubes) of the dialyzer 1110. The filtered blood then flows through the blood cartridge 500, air release device 1112, and patient line 1108 to be returned to the patient. The spent dialysate (i.e., the dialysate containing the impurities and toxins removed from the blood) is pumped to a drain via the drain line 1128 and, in certain cases, the ultrafiltration line 1129.

During the dialysis treatment, the sodium concentration of the blood in the blood circuit 10 is measured using the NMR sensor assembly 200 and the cartridge 500. The blood sodium concentration measurement or measurements can be used to ensure that the blood sodium concentration is maintained within a desired concentration range during the treatment. In some implementations, the sodium concentration is measured once, for example, at the beginning of dialysis treatment. In other implementations, the sodium concentration is measured several times during the treatment, including, but not limited to, a measurement at the beginning of the dialysis treatment, a measurement midway through the dialysis treatment, and a measurement at the end of the dialysis treatment.

Referring to FIGS. 27 and 32, to measure the sodium concentration of blood in the blood circuit 10, the blood pump 1132 positioned along the blood circuit 10 is used to deliver blood to the cartridge 500 in the manner described above. The blood enters the inlet 530 of the cartridge 500 and a fraction (e.g., 10 percent to 30 percent, 20 percent) of the blood flow entering the blood cartridge 500 enters the alignment meandering passageway 522, while the remainder of the blood enters the bypass passageway 526. The blood cartridge 500 is configured so that the blood remains within the alignment meandering fluid passageway 522 for a desired period of time (e.g., at least 150 msec, 150 msec to 300 msec, 200 msec) by controlling the blood flow rate within the alignment meandering fluid passageway 522 and the overall length of the alignment meandering fluid passageway 522. To that end, while in the alignment meandering passageway 522, the blood flow rate is typically reduced to about 200 ml/min as compared to about 500-550 ml/min in the blood lines 1170 leading to and from the blood cartridge 500. This blood residence time within the alignment meandering fluid passageway 522 ensures that substantially all the sodium atoms within the blood are aligned with the magnetic field B0.

As the blood exits the alignment meandering passageway 522, it enters the perturbation meandering passageway 524. The blood cartridge 500 is configured so that the blood remains within the perturbation meandering fluid passageway 524 for a desired period of time (e.g., at least 150 msec, 150 msec to 300 msec, 200 msec) by controlling the blood flow rate within the perturbation meandering fluid passageway 524 and the overall length of the perturbation meandering fluid passageway 524. To that end, while in the perturbation meandering passageway 524, the blood flow rate is reduced to about 100 ml/min as compared to about 500-550 ml/min in the blood lines 1170 leading to and from the blood cartridge 500. This blood residence time within the perturbation meandering fluid passageway 524 ensures that sufficient RF signal is obtained to perform an accurate sodium measurement using the NMR sensor assembly 200.

The blood flow rates through the alignment meandering fluid passageway 522, the perturbation meandering fluid passageway 524, and the bypass passageway 526 are controlled by the respective flow areas of those passageways 522, 524, 526. Because the flow area of the bypass passageway 526 is greater than the flow area of the alignment meandering fluid passageway 522, the blood flows through the bypass passageway 526 at a greater flow rate than the blood flows through the alignment meandering fluid passageway 522. As the blood exits the alignment meandering fluid passageway 522 and enters the perturbation meandering fluid passageway 524, the increased flow area of the perturbation meandering fluid passageway 524 causes the blood flow rate to decrease, while the volumetric flow rates through those passageways 522, 524 are equal.

While the blood is in the perturbation meandering passageway 524, a sodium measurement is performed on the blood by the NMR sensor assembly 200. During the measurement, the control unit 220 controls the RF coil assembly 300 including the RF coil 306 to transmit RF energy to, and receive RF energy from, the blood disposed within the perturbation meandering passageway 524.

In particular, the RF coil 306 is switched between a transmit mode and a receive mode many times to perform a scan. In the transmit mode, the RF coil 306 transmits an RF signal pulse having a voltage of about 100 V and a duration of about 10 microseconds to excite the sodium atoms to be measured in the volume V1 of the cartridge 500, causing them to precess relative to the magnetic field B0. In the receive mode, the RF coil 306 "listens" to or receives the voltage (e.g., a signal of about 100 nV) generated by the precession of the excited atoms for a duration of about 10 microseconds. For example, the sequence of transmissions and receptions performed during a scan can be a Carr-Purcell-Meiboom-Gill (CPMG) sequence in which 100 to 1500 pulses are applied to the sample, and reception is performed after each pulse. In the illustrated implementation, the scan sequence includes about 200 pulses. Due to the time required for the transmissions, the receptions, and the RF coil to transition between transmission mode and a reception mode and vice versa, about 200 msec is typically required to perform the 200 pulse scan sequence. A voltage signal is received following each transmission pulse, and the voltage signals received during a scan sequence are processed by the controller 220 to obtain a scan voltage representing the quantity of sodium in the sample volume. During the sodium measurement, about 1500 scans are performed over about a five minute measurement period, and the scan voltages obtained are then averaged by the controller 220 to address scan signal noise.

The concentration of the sodium in the blood is determined based on the received radio frequency energy generated by the excited atoms in the blood in the perturbation meandering passageway 524 of the cartridge 500, i.e., the averaged scan voltage. The averaged scan voltage is multiplied by the correction factor CF determined during calibration of the NMR sensor assembly 200 to arrive at a number corresponding to the number of sodium atoms in the sample. With knowledge of the precise volume V1 of the blood cartridge 500, as read from barcode 506 on the side of the blood cartridge 500, the sodium concentration is then calculated.

As discussed in detail above, the blood cartridge 500 is configured to support a blood sample within the RF coil 306 such that RF signals proportional to the amount of sodium in the blood can be obtained from blood that flows at a high flow rate (e.g., 500-550 ml/min) through the blood lines 1170 leading to and from the cartridge 500. This can be accomplished at least in part by providing the cartridge 500 with the bypass passageway 526, which takes the majority of the blood flow without a significant reduction in flow rate, while allowing the remainder of the flow to pass through the meandering passageways 522, 524 within the NMR sensor assembly 200 at a reduced flow rate. In addition to allowing the NMR sensor assembly 200 to determine the quantity of sodium atoms in the blood sample, the lengthened meandering passageways 522, 524 and the slowed rate of the blood through those passageways 522, 524 in combination with the configuration of the NMR sensor assembly 200 to simply determine the quantity of sodium atoms in the blood allows the NMR sensor assembly 200 to be produced relatively inexpensively because relatively small magnets can be used in the NMR sensor assembly 200.

Referring to FIG. 32, once a patient'sسsodium concentration is determined using the NMR sensor assembly 200, that information can be used to control the patient's blood sodium. For example, the amount of sodium in the dialysate can be adjusted during dialysis treatment to match the patient's initial blood sodium level. The amount of sodium in the dialysate can, for example, be adjusted by controlling the amount of water that is mixed with a dialysate concentrate or vice versa. Alternatively, sodium (e.g., sodium chloride solution) or diluent (e.g., purified water) can be added to the dialysate source 1124, as needed.

While certain implementations have been described above, other implementations are possible.

While the blood pump 1132 has been described as a peristaltic pump, other types of pumps can alternatively or additionally be used. Examples of other suitable types of pumps include diaphragm pumps and gear pumps.

While the heparin pump module 134 has been described as being used to inject heparin into the blood circuit of the hemodialysis system 101, it should be understood that any of various other drugs or supplements could alternatively or additionally be injected into the blood circuit using the pump module 134. It should be appreciated that in implementations including an airless blood circuit, heparin may not be necessary.

While the NMR sensor assembly 200 has been described as being positioned along the blood line set 140 between the dialyzer 1110 and the air release device 1112, the NMR sensor assembly 200 could be positioned at other locations along the blood line set 140.

While the NMR module 138 has been described and illustrated as being positioned on the far right side of the hemodialysis machine 101, the NMR module 138 could alternatively be positioned at a different location within the module compartment of the hemodialysis machine 100. For example, to better balance the hemodialysis machine 101, the NMR module 138 could be arranged closer to the center of the hemodialysis machine 100 if the NMR module 138 is heavier than other modules in the hemodialysis machine 101.

While the NMR module 138 has been described as including a cover plate 139 that helps to prevent damage to the NMR sensor assembly 200 disposed within the housing of the NMR module 138, in certain implementations, the NMR module includes no such cover plate.

While the NMR sensor assembly 200 has been described as being part of the removable NMR module 138, the NMR sensor assembly 200 could alternatively be a permanent, fixed component of the hemodialysis machine 101.

While the magnet units 260, 280 have been described as being secured to the support frame 201 via magnetic attraction, the magnet units 260, 280 can alternatively or additionally be secured to the support frame 201 using other techniques, such as mechanical fastening, chemical bonding, or welding.

While the magnets 261, 281 have been described as being formed of an alloy of Neodymium, Iron and Boron, in certain implementations, they are formed of one or more other materials. Examples of other suitable materials from which the magnets 261, 281 could be formed include alloys of Samarian and Cobalt and alloys of Aluminum, Nickel and Cobalt ("Alnico").

In addition, while the magnets 261, 281 have been described as permanent magnets, electromagnets could alternatively or additionally be used.

While the NMR sensor assembly 200 has been described as including rectangular magnets 261, 281, magnets of other shapes can be used. For example, in some implementations, the magnets have a cylindrical shape and are used with pole pieces 266, 286 having the shape of a truncated cone.

While the pole pieces 266, 286 have been described as being formed of soft iron, they can alternatively be formed of one or more other magnetic metals that have high magnetic permeability and/or a high saturation level. Examples of such materials include 430FR stainless steel and wrought iron-cobalt alloys such as Hiperco® 50 (available from Carpenter Products).

While the spacer body 402 of the spacer assembly 400 has been described as being formed of a ceramic material, in certain implementations, other materials are used. In certain implementations, for example, the spacer body 402 is formed of one or more electrically conductive materials, such as aluminum. In such implementations, relatively thick shield plates could be used to reduce acoustic ringing, which results from eddy currents.

While the RF coil has been described as being configured to generate a magnetic field along one axis, other types of RF coils can be used. As an example, a cage coil that generates a rotational magnetic field can be used.

While the barcode reader 498 has been described as being positioned on the spacer body 402 of the spacer assembly 400, the barcode reader 498 can be located at any location that permits it to read a barcode on the cartridge 500. Similarly, while the barcode 506 has been described as being provided on a particular region of the cartridge 500, it should be understood that the barcode 506 could be located on any portion of the cartridge 500 that is visible to the barcode reader. Moreover, while the barcode 506 and the barcode reader 498 have been described as being arranged so that the barcode 506 is automatically read upon inserting the cartridge 500 into the NMR sensor assembly 200, the barcode reader 498 can alternatively be positioned such that the user needs to scan the barcode 506 prior to inserting the cartridge 500 into the NMR sensor assembly 200. The barcode reader 498 could, for example, be located near the display 118 of the hemodialysis machine 101.

While the NMR sensor assembly 200 has been described as including a dedicated control unit 220 that controls the RF coil assembly 300 and corresponding driving electronics and that communicates with the dialysis machine control unit (e.g., via a hard-wired or wireless connection), control of the NMR sensor is not limited to this configuration. For example, in some implementations, the dialysis machine control unit may be configured to directly control the RF coil assembly and corresponding driving electronics.

Although the conductive wire 302 used to form the RF coil 306 has been described as an enamel-insulated solid copper wire, other wire configurations can be used. For example, in some implementations a litz wire (e.g., thin stranded wires that are twisted or woven) could be used to form the RF coil 306, since such wire can reduce the skin effect and proximity effect losses in conductors. While the enamel provides a very thin insulation and is thus beneficial since it minimizes the outer dimension of the RF coil 306, other insulating materials, such as plastic, could alternatively or additionally be used to coat the wire.

While the systems discussed above have been described as including RF coils that apply RF energy to and receive RF energy from medical fluid in the medical fluid cartridge, other types of RF devices can alternatively or additionally be used. For example, a "birdcage coil," which is a coil structure incorporating multiple capacitors so that the assembly has resonant modes that generate rotating fields, could be used. Such a coil may improve the RF coupling to the atomic nuclei, which rotate when excited.

While the first and second fluid passageways of the cartridge have been described as being U-shaped, in some implementations, other types of meandering fluid passageways are used. Examples of other types of meandering fluid passageways include V-shaped passageways, W-shaped passageways, M-shaped passageways, and any other passageways that lengthen a flow path within a confined space.

While the fluid passageways of the cartridge have been described as having meandering shapes, other arrangements are possible. In certain implementations, for example, the cartridge includes a straight fluid passageway that passes through the NMR sensor assembly. The cartridge can, for example, be in the form of a blood line that passes straight through the NMR sensor assembly. In such implementations, the NMR sensor assembly could be equipped with longer magnets and a longer RF coil to ensure that the blood flowing through the straight passageway is within the magnet filed and RF coil for a sufficient time period to align, perturb, and analyze the sodium atoms in the blood.

While the alignment meandering fluid passageway 522, which passes through the magnetic field generated by the NMR sensor assembly 200 but not through the RF coil 306, has been described as having a smaller flow area than the perturbation meandering fluid passageway 524, which extends through the RF coil 306, in certain implementations, the flow areas of these fluid passageways are the same. Alternatively, the flow area of the alignment meandering fluid passageway 522 can be larger than the flow area of the perturbation meandering fluid passageway 524 in certain implementations.

While certain techniques have been described for reducing the flow area of the fluid passageways of the medical fluid cartridges to reduce flow rates through the fluid passageways 522, 524, other techniques for reducing the flow area of the fluid passageways 522, 524 can be used. In some implementations, for example, columns that extend from one side of the fluid passageway to the other are used to reduce the flow area of the fluid passageway and thus reduce the flow rate of fluid therethrough. Other features, such as baffles, can alternatively or additionally be used in certain implementations.

While the cartridges 500, 2000 have been described as including barcodes that provide information regarding the cartridges (e.g., a volume of the cartridge, a quantity or concentration of sodium in a fluid contained in the catridge, etc.), other techniques for providing such information can be used. In certain implementations, for example, the cartridges are equipped with radio frequency identification (RFID) tags, which can be read by an RF reader of the NMR sensor assembly. In some implementations, the cartridges include teeth (e.g., etched or machined teeth) that can be read by an optical reader of the NMR sensor assembly. The cartridges can alternatively include printed values that can be read by an optical reader of the NMR sensor assembly or that can be read by a user and manually entered into the hemodialysis machine 101 using the display 118 and input device, such as a keyboard or touch screen.

While methods discussed above involve precisely determining the volume of the blood cartridge and then marking the blood cartridge with an indicia that includes the volume of the blood cartridge to permit an accurate concentration of sodium in the blood flowing through the blood cartridge to be determined, other techniques can be used. Referring to FIG. 44, in some implementations, the calibration method includes measuring a quantity of a first substance in a reference fluid in a reference fluid cartridge (Step 3042), measuring a quantity of a second substance in the reference fluid in the reference fluid cartridge (Step 3044), measuring a quantity of the first substance in a medical fluid in a medical fluid cartridge (Step 3046), measuring a quantity of the second substance in the medical fluid in the medical fluid cartridge (Step 3048), and determining a concentration of the second substance in the medical fluid based on the measured quantities of the first and second substances in the reference fluid and the medical fluid (Step 3050).

In certain implementations, the NMR sensor assembly is used to measure the concentration or quantity of both hydrogen and sodium in a reference fluid and those measurements are used to accurately determine the concentration or quantity of sodium in blood that is later analyzed by the NMR sensor assembly. In such implementations, the RF coil and circuit are configured to detect signals emitted by both sodium and hydrogen atoms. In particular, the RF coil is configured to be controlled by electronics to transmit and receive at more than one frequency, permitting both sodium and hydrogen atoms to be measured in a given sample. Sodium atoms precess at a frequency of 11.262 MHz/Tesla while hydrogen atoms precess at a frequency of 42.576 MHz/Tesla. In a magnetic field of 0.8 Tesla, sodium atoms precess at a frequency of 9.0 MHz and hydrogen atoms precess at a frequency of 34.06 MHz. Because hydrogen atoms precess at a different frequency than sodium atoms, additional electronics functionality is used to properly measure the voltage generated by each molecule type. In particular, the RF coil used to excite the atoms and then to detect their precession in a "listening" or receiving mode is tuned to the two different resonance frequencies of 1H and 23Na.

FIG. 33 shows a block diagram of a version of a circuit 600a used in such an NMR sensor assembly. The circuit 600a includes a dual tuned coil 306a that can be used to sense both sodium atoms and hydrogen atoms. As used herein the term "dual tuned RF coil" refers to an RF coil that can be used to emit electromagnetic energy and/or detect electromagnetic energy at two different frequencies. The dual tuned coil 306a is connected to a double tuned resonant circuit 602a. In this example, the capacitors and inductors of the resonant circuit 602 are configured to resonate at two frequencies, each of which is a resonant frequency of the dual tuned coil 306a.

The resonant circuit 602a connects to isolation circuits 604, 606. One isolation circuit 604 is for a sodium portion of the circuit 600, and another isolation circuit 606 is for a hydrogen portion of the circuit 600a. The circuit 600a cannot both transmit and receive at the same time, so each of the isolation circuits 604, 606 includes switches that isolate the transmitting portions of the circuit 600a from the receiving portions of the circuit 600a.

When the isolation circuits 604, 606 are switched to a transmitting mode, two transmitting amplifiers 608, 610 are activated, one of which amplifies a signal for the sodium frequency (e.g., a signal at a frequency of 11.262 MHz/Tesla of magnetic field) and one of which amplifies a signal for the hydrogen frequency (e.g., a signal at a frequency of 42.576 MHz/Tesla of magnetic field). The signals cause the dual tuned coil 306a to generate an electromagnetic field that excites sodium and hydrogen atoms. A clock generation circuit 612 generates signals that pass through each amplifier 608, 610.

When the isolation circuits 604, 606 are switched to a receiving mode, a signal received by the dual tuned coil 306a passes through the resonant circuit 602 to two low-noise amplifiers 614, 616, one of which amplifies a signal for the sodium frequency and one of which amplifies a signal for the hydrogen frequency. The outputs of the low-noise amplifiers 614, 616 are provided to an analog-digital converter 618 (ADC). An analog-digital converter takes as input an analog signal and converts it to a digital signal for use with digital components. Here, the analog-digital converter 618 outputs digital versions of the signals received and amplified by the circuit 600a. The signals are output to digital components that analyze the signals to determine information about the sodium and hydrogen in a patient's blood. An FPGA 622 can be used to synchronize the transmitting and receiving modes for each of the two frequencies and implement the timing for the NMR pulse sequence.

The dual tuned coil 306a is selected to have a high impedance (e.g., 10K ohms or more, 50K ohms or more). When the isolation circuits 604, 606 are switched to a transmitting mode (e.g., when the dual tuned coil 306 transmits a signal to excite sodium or hydrogen atoms), the receiving components are isolated from the high voltages of the transmitting mode. When the isolation circuits 604, 606 are switched to a receiving mode (e.g., when the coil is waiting to detect electromagnetic fields generated by the precession of the excited atoms), the transmitting components are isolated from the low voltage receiving components. When combined with the dual tuned coil 306a, this arrangement allows low voltage electronic components to be placed on the circuit 600 without the risk of damage.

Some transmitter/receiver circuits use a matching circuit to connect a high impedance coil to a low impedance (e.g., 50 ohms) load. However, in this circuit 600a, the switching components (e.g., the isolation circuits 604, 606) are directly connected to the dual tuned coil 306a and no impedance matching circuit is used. If the dual tuned coil 306a is operated at a low impedance, the coil would lose sensitivity due to energy lost from the impedance of the components of the isolation circuits 604, 606. The loss of energy would increase the amount of time needed to receive enough energy to analyze the signal in the receiving mode.

Since the dual tuned coil 306a has a high impedance, the RF coil 306a can be connected to a high-impedance low-noise amplifier (e.g., low-noise amplifiers 614, 616). High-impedance low-noise amplifiers are used so that a matching circuit need not be used to connect the low-noise amplifiers and the dual tuned coil 306a.

FIG. 34 shows a circuit 800 implementing a portion of the functionality of the circuit 600a shown in FIG. 33. One point 802 of the circuit 800 is the location at which the low-noise amplifier 614 for the sodium frequency can be connected, and another point 806 of the circuit is the location at which the low-noise amplifier 616 for the hydrogen frequency can be connected. A third point 804 of the circuit is a location at which a signal from the dual tuned coil 306 enters the circuit.

FIG. 35 shows a graph of the frequency response of the circuit 800 as measured at the first point 802. As shown in FIG. 35, the impedance has a peak 808 at approximately 5 MHz and another peak 810 at approximately 80 MHz.

FIG. 36 shows a graph of the frequency response of the circuit 800 as measured at the second point 2302. As shown in FIG. 36, the impedance has peaks 812, 814 and 816 at approximately 4 MHz, 11.5 MHz, and 80 MHz.

FIG. 37 shows a graph of the frequency response of the circuit 800 as measured at the third point 2402. As shown in FIG. 37, the impedance has peaks 818, 820 and 822 at approximately 5 MHz, 11.5 MHz, and 80 MHz.

FIG. 38 shows a graph of the frequency response of the dual tuned coil 306a shown in FIG. 33. As shown in FIG. 38, the magnitude of the impedance of the coil has peaks 902, 904 at 9.5 MHz and 45 MHz, which are approximate the frequencies of precession of sodium and hydrogen atoms in the magnetic fields used in the techniques described herein. The magnitudes of the peaks 902, 904 shown in FIG. 38 are achieved by adjusting variable capacitors in the circuit 800.

A method of using a dialysis system equipped with the dual tuned coil 306a and the electronics of FIG. 35 will now be briefly described. It should be understood that this dialysis system is generally the same as the dialysis system 101 described above, except for the dual tuned coil 306a and the electronics of the NMR sensor assembly of this dialysis system. Prior to beginning the dialysis treatment, the reference cartridge 2000, which contains a reference fluid having a known concentration or quantity of sodium and hydrogen, is inserted into the NMR sensor assembly and the NMR sensor assembly measures the concentration or quantity of sodium and hydrogen in the reference fluid and stores that information in its controller. The quantity or concentration of sodium detected by the NMR sensor assembly is then compared to the known quantity or concentration of sodium in the reference fluid and the NMR sensor assembly is calibrated in the manner described above to account for any discrepancy between the detected quantity or concentration of sodium and the known quantity or concentration of sodium.

After measuring the sodium and hydrogen concentration or quantity in the reference fluid, the reference cartridge 2000 is removed from the NMR sensor assembly and the blood cartridge 500 is inserted into the NMR sensor assembly. Prior to circulating blood through the cartridge 500, a saline solution is introduced to the cartridge for priming. For example, a bag of saline solution can be connected to the blood line set and the blood pump can be operated to pump the saline solution to the blood cartridge 500. The NMR sensor assembly then measures the quantity of hydrogen in the saline solution and stores that value in its controller.

The hemodialysis treatment is then initiated. During the treatment blood flows through the blood cartridge 500 and the quantity of sodium in the blood is measured by the NMR sensor assembly.

The ratio of the sodium and hydrogen signals (i.e., the signals that are received by the NMR sensor assembly and are indicative of the quantities of hydrogen and sodium, respectively, in the fluid being analyzed) depends only on the quantities or concentrations of sodium and hydrogen in the fluid, not on the cartridge volume. Both signals are proportional to the fluid volume within the RF coil 306a.

In addition, it is known (or can be assumed) that the hydrogen concentration is the same in the reference fluid analyzed in the reference cartridge 2000 and the saline solution analyzed in the blood cartridge 500. Specifically, in any dilute aqueous solution, water is the dominant constituent and so the hydrogen concentration is very close to that of water.

An accurate determination of the concentration of sodium in the blood sample can be made by comparing (1) the ratio of the measured sodium signal in the reference fluid to the measured hydrogen signal in the reference fluid (i.e., 23Na:1H signal ratio for the reference fluid) to (2) the ratio of the measured sodium signal in the blood sample fluid to the measured hydrogen signal in the blood sample (i.e., 23Na:1H signal ratio for the blood sample). As noted above, the hydrogen concentration in the reference fluid in the reference cartridge 2000 is equal to the hydrogen concentration in the saline solution in the blood cartridge 500 since the reference fluid and the saline solution are both dilute aqueous solutions. Therefore, to the extent that the hydrogen signals received during analysis of the reference fluid differ from the hydrogen signals received during analysis of the blood sample, it can be assumed that the different readings are the result of a difference between the volumes of the reference cartridge 2000 and the blood cartridge 500. The ratio of the sodium signal to the hydrogen signal, however, is not dependent on the volume of the sample analyzed. Therefore, if the concentrations of sodium and hydrogen in two different samples were the same, then the ratio of the sodium signal to the hydrogen signal would also be the same, regardless of whether the sample volumes differed from one another. In other words, even though the values or intensities of the sodium and hydrogen signals of a first larger volume sample may differ from the values or intensities of the sodium and hydrogen signals of a second smaller volume sample, the sodium signal to hydrogen signal ratio would be the same for each sample so long as the sodium and hydrogen concentrations were the same in those samples.

In view of the foregoing discussion, it will be clear that any difference between the sodium signal to hydrogen signal ratio (23Na:1H) of the reference fluid and the sodium signal to hydrogen signal ratio (23Na:1H) of the blood sample, as measured by the NMR sensor assembly during the method discussed above, could be attributed to a difference between sodium concentrations in the reference fluid and the blood sample. Thus, the concentration of sodium in the blood sample can be determined by comparing the ratio of the sodium signal to hydrogen signal ratio (23Na:1H) of the reference fluid and the sodium signal to hydrogen signal ratio (23Na:1H) of the blood sample.

As an example, suppose the ratio of the sodium signal to the hydrogen signal (23Na:1H) from the reference cartridge 2000 is 0.1 and that the reference cartridge contains a 1M sodium solution. Then, during dialysis, a ratio of the sodium signal to the hydrogen signal (23Na:1H) of the blood sample and saline solution, respectively, in the blood cartridge 500 is determined to be 0.01. It can be determined from this information that the sodium concentration of the blood sample is 0.1 M (i.e., 0.01/0.1*1M).

A detailed explanation of the manner in which the sodium concentration of the blood sample in the blood cartridge 500 can be determined using the sodium and hydrogen signals received from the blood sample and the reference fluid is provided below.

As discussed above, the ratio of hydrogen and sodium signals from a single cartridge is independent of the machine calibration, and only depends on the sodium concentration.

NMR provides a signal, S, that is proportional to species concentration, C, but the gain between these depends on the gain of the machine, g, which is species dependent, and the effective volume of the cartridge, V: $C=(g/V) \cdot S$ The reference cartridge 2000 holds a known volume of a known concentration of sodium $[Na]_{ref}$.

The concentration of hydrogen in both the reference fluid and the saline solution used to prime the blood line set can be assumed to be that of water, i.e. $[H]_{H2O}=55.5M$.

The sodium and hydrogen signals are both measured for the reference cartridge 2000: $S_{Na,ref}$ and $S_{H,ref}$. Let the effective volume of the reference cuvette be $V_{ref}$. This gives two equations, $$[Na]_{ref}=(g_{Na}/V_{ref})S_{Na,ref}$$

$$[H]_{H2O}=(g_H/V_{ref})S_{H,ref}$$

Taking the ratio between these determines the machine calibration:

$$g_{Na}/g_H=[Na]_{ref}S_{H,ref}/[H]_{H2O}S_{Na,ref}$$

Let the effective volume of the blood cartridge 500 be $V_{con}$. This gives another two equations, $$[Na]_{con}=(g_{Na}/V_{con})S_{Na,con}$$

$$[H]_{H2O}=(g_H/V_{con})S_{H,con}$$

Taking the ratio between these gives the following $$[Na]_{con}/[H]_{H2O}(g_{Na}/g_H)(S_{Na,con}/S_{H,con})$$

Using the above, the concentration of sodium in the blood can be determined in terms of known quantities.

While the hydrogen calibration technique described above involves the use of the reference cartridge 2000, which contains a reference fluid having a known concentration or quantity of sodium and hydrogen, other techniques can be used. In certain implementations, for example, the blood cartridge 500 is prefilled with a saline solution and is provided to the consumer in that manner. The cartridge 500 can, for example, be provided with caps that fit over the line connectors 534 of the blood cartridge 500 to contain the saline solution therein. Before connecting the cartridge 500 to the remainder of the blood line set 140 in such implementations, the cartridge 500 would be inserted into the NMR sensor assembly 200 and used to calibrate the NMR sensor assembly 200 in the manner described above. In particular, the NMR sensor assembly 200 would measure the concentration or quantity of the sodium and hydrogen in the saline solution and compare the measured sodium concentration or quantity to the known concentration or quantity of the sodium in the saline solution to determine a correction factor CF to be used to adjust future blood sodium readings carried out by the NMR sensor assembly. After calibrating the NMR sensor assembly 200 in this manner, the blood lines of the blood line set 140 would be connected to the blood cartridge 500 and the hemodialysis treatment would be initiated. The saline solution could either be drained from the cartridge 500 prior to beginning the treatment or simply delivered to the patient. During treatment, the blood sodium concentration could be determined in the manner discussed above.

As an alternative to prefilling the cartridge 500 with saline solution in the manner discussed above, the cartridge 500 can be provided in an empty state and the clinician can fill the cartridge 500 with saline solution having a known sodium concentration and a known hydrogen concentration prior to use. The calibration technique and treatment can then be carried out in the manner described above.

In some implementations, the NMR sensor assembly is not calibrated prior to use. In some such implementations, for example, the cartridges are precision machined to ensure that the volumes of the cartridges do not significantly change from one cartridge to another and to ensure that the actual volume of the cartridge does not significantly differ from the intended volume. In such cases, the cartridges wouldn't need to be marked with their actual volume or otherwise tested to determine (directly or indirectly) their actual volume. Assuming the machine is designed to work with only one type of cassette, then the machine could be programmed (e.g., by the manufacturer) to store the intended volume of the cassette without the need for a barcode reader or a similar device that transmits information regarding the actual volume of the cartridge to the controller of the NMR sensor assembly. The intended volume could then be used in combination with the determined quantity of sodium in a blood sample to determine the sodium concentration in a patient's blood.

In certain implementations, a relatively large cartridge is used. Such a cartridge can, for example, have a volume of 5 mL to 30 mL. Due to the large volume of the cartridge, differences in the actual volume of the cartridge from the intended volume of the cartridge, which can result from relatively imprecise manufacturing techniques, such as injection molding, will have a negligible affect on a sodium concentration that is determined by dividing a sodium quantity reading by the intended volume of the cartridge.

While the methods discussed above involve determining actual sodium concentrations of the blood, in certain implementations, it is only necessary to monitor a change in sodium concentration over time. The sodium concentration of the dialysate could, for example, be adjusted using a feedback loop in response to blood sodium level changes that occur during treatment. As a result, it would be unnecessary to know the actual blood sodium concentration of the patient. Rather, the goal would be to maintain the sodium concentration at a constant level throughout the treatment. In such implementations, calibration of the NMR sensor assembly and determination of the actual volume of the blood cartridge would typically not be carried out.

While the methods discussed above involve pumping the blood through the cartridge while applying and receiving the RF energy to determine the concentration of sodium in the blood, in some implementations, the RF energy is applied to and received from a static sample of blood to determine the concentration of sodium in the blood. The cartridge can, for example, include an inlet fluid passageway that leads from an inlet blood line connected to the cartridge to a chamber and an outlet fluid passageway that leads from the chamber to an outlet blood line connected to the cartridge. The outlet blood line is connected at its opposite end to a disposable container, such as a bag or vial. The inlet and outlet fluid passageways are connected to valve mechanisms that can be operated to open and close the passageways. During use, blood is delivered to the chamber via the inlet fluid passageway with the valve mechanism closing the outlet fluid passageway. After filling the chamber with blood, the valve mechanism along the inlet fluid passageway is likewise closed to contain the blood within the chamber. The NMR sensor assembly can then be used to determine the concentration of the static blood sample within the chamber. Rather than returning the blood to the patient after the analysis, the blood is delivered to the disposable container, which can be properly disposed of after treatment. Since the blood sample in this valved cartridge is static, a much smaller flow passageway would be required in the cartridge, whereby the valved cartridge could be made much smaller than the previously described blood cartridges.

While the systems and methods above have been described as being used to directly determine the concentration of sodium in a patient's blood, in some implementations, the concentration of sodium in the patient's blood is determined indirectly, based on detected levels of sodium in the dialysate. A method of using the NMR sensor assembly 200 to indirectly measure blood sodium concentration using dialysate is similar to the concept described above relating to measuring a patient's blood sodium directly. However, instead of including the disposable blood cartridge 500 in the blood circuit 10, diverting a portion of the patient's blood in the disposable blood cartridge 500 into the RF coil 306, and measuring the flowing blood sample directly, a rigid permanent dialysate cartridge 1500 is provided in the dialysate circuit 12 having access via valves 1502, 1504, 1506 to both the pre-dialyzer dialysate flow (e.g., "clean" dialysate) as well as the post-dialyzer dialysate flow (e.g., "spent" dialysate).

FIG. 39 shows schematic representations of the blood and dialysate circuits of a hemodialysis machine configured to indirectly determine the concentration of sodium in a patient's blood, and FIG. 40 shows a dialysate cartridge 1500 that is provided along the dialysate circuit and is used to hold samples of dialysate to be analyzed by the NMR sensor assembly 200. Referring to FIGS. 39 and 40, the dialysate cartridge 1500 is in fluid communication with the dialysate circuit via a first valve 1502 that connects a first inlet 1512 of the dialysate cartridge 1500 to the dialysate supply line 1126, a second valve 1504 that connects a second inlet 1514 of the dialysate cartridge 1500 to the dialysate drain line 1128, and a third valve 1506 that connects an outlet 1516 of the dialysate cartridge 1500 to the dialysate drain line 1128 at a location between the second valve 1504 and the drain 1508. The dialysate cartridge 1500 includes a reservoir 1518 dimensioned to be received within the RF coil 306 of the NMR sensor assembly 200. The volume of the reservoir 1518 is precisely measured at manufacture, and an outer surface of the cartridge is provided with a barcode indicating the volume of the reservoir 1518. The dialysate cartridge 1500 is permanently disposed in the NMR sensor assembly 200, and is received within a modified spacer body 402' such that the first inlet 152 and the second inlet 1514 extend through the spacer body opening 430, and such that the outlet 1516 extends through another opening 432 formed in the spacer body third edge 416. In addition, the reservoir 1518 is enclosed by the RF coil 306. Because the dialysate cartridge 1500 is typically a permanent component (i.e., not a single use component) of the dialysis system, the dialysate cartridge 1500 and the NMR sensor assembly 200 can be built as a permanent assembly that is housed within the main housing of the dialysis machine.

Conductivity sensors 1600 are positioned along the dialysate line 1216 of the dialysate circuit upstream and downstream of the dialyzer 1110.

A method of using the NMR sensor assembly 200 to indirectly measure blood sodium concentration on the patient's dialysate obtained during dialysis treatment will now be described.

Once hemodialysis treatment is underway such that both blood and dialysate are running through the dialyzer 1110, an on line dialysance clearance is performed using the conductivity sensors 1600, and a clearance value (Kecn) is derived from the following formula:

$$Kecn=(Qd*Qf/60)*(1-((CpoUp-CpoDn)/CpiUp-CpiDn)))$$

where
Kecn is effective Na clearance
Qd is dialysate flow rate
Qf is Ultrafiltration flow rate
CpoUp and CpoDn are the conductivities of the dialysate post dialyzer during the stable Up step and down steps in conductivity
CpiUp and CpiDn are the conductivities of the dialysate pre dialyzer during the stable up and down steps in conductivity.

After completion of the dialysance clearance, the dialysate conductivity is allowed to stabilize. Upon stabilization of the dialysate conductivity, the first valve 1502 and third valves 1506 are opened and the second valve 1504 is closed while running the dialysate pumps 1204 and 1212. This valve configuration permits fresh dialysate to flow from the fresh dialysate source 1124 through the reservoir 1518 of the dialysate cartridge 1500. Specifically, the fresh dialysate enters the cartridge 1500 via the first inlet 1512 of the cartridge 1500, travels through the reservoir 1518, and then exits the cartridge 1500 via an outlet 1516 of the cartridge 1500. The fresh dialysate is allowed to flow through the cartridge 1500 for a sufficient period of time to flush the reservoir 1518 of any air or previously analyzed dialysate that may have been in the reservoir 1518. The first valve 1502 is configured such that fresh dialysate is also allowed to flow through the valve 1502 toward the dialyzer 1110 while fresh dialysate is being delivered to the dialysate cartridge 1500. The closed second valve 1504 prevents fresh dialysate from flowing through the cartridge 1500 and into the drain line 1128 via the second valve 1504 but allows spent dialysate travelling through the drain line 1128 to pass through the second valve 1504 and proceed to the drain 1508.

After the reservoir 1518 has been flushed, the third valve 1506 is closed while the first valve 1502 remains open and the dialysate pumps 1204, 1212 continue to run. This configuration directs fresh dialysate to the first inlet 1512 of the cartridge 1500, and the reservoir 1518 is filled with fresh dialysate. Since the second and third valves 1504, 1506 are closed, the fresh dialysate is not allowed to pass through the cartridge 1500. Once the reservoir 1518 is filled, the fresh dialysate first valve 1502 is closed so that there is no fluid flow to or through the cartridge 1500. However, fresh dialysate continues to pass through the first valve 1502 to the dialyzer 1110 and spent dialysate continues to pass through the second valve 1504 to the drain 1508. In this way, hemodialysis treatment can resume even while the cartridge 1500 is being filled and the dialysate within the cartridge 1500 is being tested.

With the sample of fresh dialysate contained in the reservoir 1518, the NMR sensor assembly 200 is then operated to measure the sodium concentration in the fresh dialysate (CdiNa). The NMR sensor assembly 200 is operated in generally the same manner as described above with respect to measurement of sodium concentration in the blood cartridge 500. Specifically, since the reservoir 1518 of the dialysate cartridge 1500 is disposed within the RF coil 306, the fresh dialysate filling the reservoir resides within the magnetic field B0. With the fresh dialysate disposed within the RF coil 306, a predetermined waiting period is allowed to elapse before a sodium measurement is performed. The waiting period permits the sodium atoms within the reservoir 1518 to become aligned with the magnetic field B0. For example, the waiting period can be in a range of 150 to 300 msec (e.g., 200 msec).

Following the waiting period, and while the fresh dialysate is disposed within the reservoir 1518, a sodium measurement is performed on the fresh dialysate by the NMR sensor assembly 200. During the measurement, the control unit 220 controls the RF coil assembly 300 including the RF coil 306 to transmit RF energy to, and receive RF energy from, the fresh dialysate disposed within reservoir 1518.

In particular, the RF coil 306 is switched between a transmit mode and a receive mode many times to perform a scan. In the transmit mode, the RF coil 306 transmits an RF signal pulse having a voltage of about 100 V and a duration of about 10 microseconds to excite the sodium atoms to be measured in the volume of the cartridge 1500, causing them to precess relative to the magnetic field B0. In the receive mode, the RF coil 306 "listens" to or receives the voltage (e.g., a signal of about 100 nV) generated by the precession of the excited atoms for a duration of about 10 microseconds. For example, the sequence of transmissions and receptions performed during a scan can be a Carr-Purcell-Meiboom-Gill (CPMG) sequence in which 100 to 1500 pulses are applied to the sample, and reception is performed after each pulse. In the illustrated implementation, the scan sequence includes about 200 pulses. Due to the time required for the transmissions, the receptions, and the RF coil to transition between transmission mode and a reception mode and vice versa, about 200 msec is typically required to perform the 200 pulse scan sequence. A voltage signal is received following each transmission pulse, and the voltage signals received during a scan sequence are processed to obtain a scan voltage representing the quantity of sodium in the sample volume. During the sodium measurement, about 1500 scans are performed over about a five minute measurement period, and the scan voltages obtained are then averaged to address scan signal noise.

Next, the concentration of the sodium within the fresh dialysate is determined based on the averaged scan voltage. The average scan voltage is multiplied by the correction factor CF to arrive at a number corresponding to the number of sodium atoms in the fresh dialysate. With knowledge of the precise volume of the cartridge 1500, the sodium concentration of the fresh dialysate (CdiNa) is then calculated.

Following the measurement of the sodium concentration in the fresh dialysate, the first valve 1502 is closed, and the second and third valves 1504, 1506 are opened while the dialysate pumps 1204, 1212 continue to run. As a result of this valve configuration, spent dialysate is directed to the second inlet 1514 of the dialysate cartridge 1500, and the spent dialysate is allowed to flow through the dialysate cartridge 1500 for a time period sufficient to flush any remaining fresh dialysate from the reservoir 1518. When the reservoir 1518 has been flushed, the third valve 1506 is closed, and the reservoir 1518 is filled with spent dialysate. Once the reservoir 1518 has been filled with spent dialysate, the second valve 1504 is also closed to ensure that the spent dialysate sample is contained within the reservoir 1518. The NMR sensor assembly 200 is then operated to measure the sodium concentration in the spent dialysate (CdoNa). To do this, the NMR sensor assembly 200 is operated in the same manner as described with respect to the measurement of the fresh dialysate.

Fresh dialysate traveling through dialysate supply line 1126 is allowed to pass through the first valve 1502 to the dialyzer 1110 and spent dialysate traveling through the drain line 1128 is allowed to pass through the second valve 1504 to the drain 1508 through the process of the spent dialysate being delivered to the cartridge and tested such that the hemodialysis treatment does not have to be stopped or paused while filling the cartridge 1500 or testing the spent dialysate within the cartridge 1500.

Following the measurement of the sodium concentration in the spent dialysate, the controller 220 calculates the blood sodium using the following formula:

$$Na = CdiNa(1 - Qd/Kecn)(1 - CdoNa/CdiNa)$$

where

CdiNa is the sodium concentration of the fresh dialysate

CdoNa is the sodium concentration of the spent dialysate

The underlying principle behind this method is that small molecular solutes will pass the dialyzer's 1110 semipermeable membrane to try to reach equilibration of the solute due to diffusion gradient differences. The clearance value Kecn is used to determine the efficiency of the blood/dialysate interaction. The sodium concentration of the fresh dialysate CdiNa determines the base dialysate sodium concentration, and the sodium concentration of the spent dialysate CdoNa indicates the direction of the equilibration of sodium. If the blood sodium concentration Na is higher than the base dialysate sodium concentration (e.g., higher than CdiNa), then the sodium concentration of the spent dialysate CdoNa concentration will also be higher than the base. The rate of this increase based on the clearance value Kecn allows calculation of the concentration gradient needed in the blood to cause the increase in the sodium concentration of the spent dialysate CdoNa. The same effect occurs in the opposite direction. That is, a sodium concentration Na that is lower than the sodium concentration of the fresh dialysate CdiNa results in the sodium concentration of the spent dialysate CdoNa being lower than the base dialysate sodium concentration (e.g., lower than CdiNa). The rate of this decrease based on the clearance value Kecn allows calculation of the concentration gradient needed in the blood to cause the decrease in the sodium concentration of the spent dialysate CdoNa.

Once the patient's initial blood sodium concentration (i.e., the blood sodium concentration at the beginning of treatment) has been determined, the controller 220 will cause the sodium concentration of the fresh dialysate to be adjusted to match the sodium concentration of the patient's blood. For example, the amounts of water and dialysate concentrate that are delivered to the dialysate source 1124 can be adjusted to adjust the sodium concentration of the fresh dialysate. This will reduce the likelihood that the patient's blood sodium concentration will change during treatment. Further sodium tests can be carried during the treatment and the sodium concentration of the dialysate can be further adjusted, if desired, to ensure that the patient's blood sodium concentration remains at or near the initial blood sodium concentration throughout the treatment.

The method of using the NMR sensor assembly 200 to indirectly measure blood sodium concentration using dialysate may have some advantages over the direct blood measurement method. For example, in contrast to the disposable blood cartridge 500, because spent dialysate is drained to waste, the permanent measurement dialysate cartridge 1500 can be reused among multiple patients without needing to be sterilized or replaced. Furthermore, because only one dialysate cartridge 1500 is needed per dialysis machine 100, the dialysate cartridge 1500 can be machined with a very high precision (to achieve the very precise volume required for accurate NMR measurement), as the cost of precisely machining one permanent cartridge per machine is much more feasible than precisely machining millions of disposable blood cartridges 500. Finally, unlike blood samples which must remain flowing to preserve the "non-contact" status of this technology, spent dialysate can be "pinched off" into the permanent dialysate cartridge 1500 and measured as a static sample. This eliminates any concerns relating to clotting or build-up associated with use of the blood cartridge 500, and also renders moot any effects that a flowing sample might have on NMR measurement in general.

While the NMR sensor assembly 200 of the hemodialysis system of FIGS. 39 and 40 is typically not calibrated prior to use, in certain implementations, a calibration procedure is carried out prior to beginning dialysis treatment. In such implementations, for example, prior to initiation of dialysate flow through the dialysate circuit 12, the reservoir 1518 of the dialysate cartridge 1500 can be filled with a saline solution of known sodium concentration. This can be accomplished by connecting a bag of saline solution having a known sodium concentration to the dialysate supply line 1126 and operating the dialysate pump 1204 and valves 1502, 1504, 1506 to fill the reservoir 1518. After a predetermined waiting period has elapsed and allowed the sodium atoms within the saline solution in the reservoir 1518 to become aligned with the magnetic field B0 generated by the NMR sensor assembly 200, a sodium measurement is performed on the saline solution in the reservoir 1518. During the measurement, the control unit 220 controls the RF coil assembly 300 including the RF coil 306 to transmit RF energy to, and receive RF energy from, the saline solution disposed within reservoir 1518. This measurement provides the measured reference sodium quantity, which is used along with the known sodium concentration of the saline solution and the volume of the cartridge 1500 to calculate the machine correction factor (CF). This correction factor can be applied to future sodium measurements to account for slight variations in the performance of the NMR sensor assembly 200, which may occur from treatment to treatment or over a period of time.

While the hemodialysis system of FIGS. 39 and 40 has been described as including the NMR sensor assembly 200 discussed above, any of the various other types of NMR sensor assemblies described herein can alternatively be used in this system.

While the dialysate cartridge 1500 has been described as including a bar code that contains the volume of the dialysate cartridge 1500, in some implementations, the dialysate cartridge includes no such bar code. For example, because the dialysate cartridge is precisely machined to have a desired volume, the controller of the dialysis machine can be programmed (e.g., by the manufacturer) to store the intended volume of the dialysate cartridge and that intended volume can be used to determine the concentration of sodium in the dialysate samples contained in the dialysate cartridge.

While the systems and methods discussed above relate to determining the concentration of sodium in a patient's blood, similar techniques can be used for determining the concentration of other substances in a patient's blood, such as calcium, phosphorous, magnesium, potassium, and other electrolytes normally found in blood.

While the systems and methods discussed above relate to determining the concentration of a substance in the blood of a patient undergoing hemodialysis treatment, similar techniques can be used for determining the concentration of a substance in a patient's blood during other types of medical treatments. Examples of such treatments include cardiopulmonary bypass procedures and plasmapheresis.

In some implementations, instructions that cause a computer to carry out one or more steps of a process are stored on a computer readable medium. Computer readable media suitable for storing computer program instructions and data include all forms of storage devices, e.g., non-volatile or volatile memory, media and memory devices, including by way of example semiconductor memory devices, e.g., EPROM, EEPROM, and flash memory devices; magnetic disks, e.g., internal hard disks or removable disks or magnetic tapes; magneto optical disks; and CD-ROM and DVD-ROM disks.

Other implementations are within the scope of the following claims.

What is claimed is:

1. A method comprising:
reading an indicia of a medical fluid cartridge to determine a volume of a first fluid passageway of the medical fluid cartridge indicated by the indicia;
removeably positioning the medical fluid cartridge in a first magnetic field, such that the first fluid passageway is positioned within a radio frequency device in the magnetic field, and a second fluid passageway of the medical fluid cartridge is positioned within the magnetic field and outside the radio frequency device;
flowing dialysis fluid in the second fluid passageway, the first magnetic field aligning atoms of a substance of the dialysis fluid in the second fluid passageway;
flowing the dialysis fluid from the second fluid passageway into the first fluid passageway;
transmitting radio frequency energy to the dialysis fluid in the first fluid passageway using the radio frequency device, the radio frequency energy changing the alignment of the atoms of the substance of the dialysis fluid, the atoms of the substance generating a second magnetic field in the first fluid passageway;
receiving radio frequency energy generated by the atoms of the substance in the dialysis fluid in the first fluid passageway of the medical fluid cartridge, the radio frequency device receiving the radio frequency energy; and
determining a concentration of the substance in the dialysis fluid in the first fluid passageway based on the determined volume of the first fluid passageway of the medical dialysis fluid cartridge indicated by the indicia and the received radio frequency energy generated by the atoms of the substance of the dialysis fluid in the first fluid passageway of the medical fluid cartridge.

2. The method of claim 1, further comprising determining an actual volume of the first fluid passageway of the medical fluid cartridge and applying the indicia to the medical fluid cartridge, the indicia being indicative of the determined actual volume of the first fluid passageway of the medical fluid cartridge.

3. The method of claim 2, wherein determining the actual volume of the first fluid passageway of the medical fluid cartridge comprises measuring the actual volume of the first fluid passageway of the medical fluid cartridge.

4. The method of claim 1, wherein the indicia of the medical fluid cartridge is read by a machine.

5. The method of claim 1, wherein the machine is a barcode reader and the indicia is a barcode.

6. The method of claim 1, wherein the radio frequency energy generated by the atoms of the substance of the dialysis fluid in the first fluid passageway of the medical fluid cartridge is received by a sensor assembly comprising the radio frequency device.

7. The method of claim 6, wherein prior to determining the concentration of the substance in the dialysis fluid, the sensor assembly is used to determine a concentration of the substance in a reference fluid in a reference fluid cartridge and the sensor assembly is calibrated based on the determined concentration of the substance in the reference fluid in the reference fluid cartridge.

8. The method of claim 7, wherein calibrating the sensor assembly comprises comparing the concentration of the substance in the reference fluid in the reference fluid cartridge as determined by the sensor assembly to a known concentration of the substance in the reference fluid in the reference fluid cartridge.

9. The method of claim 1, further comprising flowing the dialysis fluid in the first and second passageways, the dialysis fluid flowing (i) through the second fluid passage way, (ii) into the first fluid passageway, and (iii) through the first fluid passageway.

10. The method of claim 1, wherein applying the radio frequency energy to the dialysis fluid in the first fluid passageway of the medical fluid cartridge comprises activating the radio frequency device.

11. The method of claim 10, wherein the radio frequency device is a radio frequency coil.

12. The method of claim 1, further comprising adjusting the concentration of the substance in the dialysis fluid if the determined concentration of the substance in the dialysis fluid falls outside of a desired range.

13. The method of claim 1, wherein the dialysis fluid is blood.

14. The method of claim 1, wherein the dialysis fluid is dialysate.

15. The method of claim 1, wherein the substance is sodium.

* * * * *